(12) United States Patent
Kim et al.

(10) Patent No.: US 8,772,290 B2
(45) Date of Patent: Jul. 8, 2014

(54) ALPHA-ARYLMETHOXYACRYLATE DERIVATIVE, PREPARATION METHOD THEREOF, AND PHARMACEUTICAL COMPOSITION CONTAINING SAME

(75) Inventors: Se-Won Kim, Cheonan-si (KR); Jung Ho Kim, Cheonan-si (KR); Se-Nyum Kim, Cheonan-si (KR); Dae-Pil Kang, Osan-si (KR); Youn Ho Han, Gwangju-si (KR); Guo Fan Jin, Cheonan-si (KR); Dong-Sik Jung, Cheonan-si (KR); Sung-Ho Park, Cheonan-si (KR); Ji Min Kim, Yangpyeong-gun (KR); Jhi Zheng, Cheonan-si (KR)

(73) Assignee: Oscotech Inc., Cheonan-si (KR)

( * ) Notice: Subject to any disclaimer, the term of this patent is extended or adjusted under 35 U.S.C. 154(b) by 0 days.

(21) Appl. No.: 13/392,024

(22) PCT Filed: Apr. 21, 2011

(86) PCT No.: PCT/KR2011/002892
§ 371 (c)(1),
(2), (4) Date: Feb. 23, 2012

(87) PCT Pub. No.: WO2011/132967
PCT Pub. Date: Oct. 27, 2011

(65) Prior Publication Data
US 2012/0149707 A1    Jun. 14, 2012

(30) Foreign Application Priority Data
Apr. 21, 2010 (KR) .................. 10-2010-0037041

(51) Int. Cl.
| | | |
|---|---|---|
| A61K 31/216 | (2006.01) | |
| A61K 31/336 | (2006.01) | |
| A61K 31/40 | (2006.01) | |
| A61K 31/415 | (2006.01) | |
| A61K 31/421 | (2006.01) | |
| A61K 31/4402 | (2006.01) | |
| A61K 31/4409 | (2006.01) | |
| A61K 31/4453 | (2006.01) | |
| A61K 31/5375 | (2006.01) | |

(52) U.S. Cl.
CPC ............ *A61K 31/216* (2013.01); *A61K 31/336* (2013.01); *A61K 31/40* (2013.01); *A61K 31/415* (2013.01); *A61K 31/421* (2013.01); *A61K 31/4402* (2013.01); *A61K 31/4409* (2013.01); *A61K 31/4453* (2013.01); *A61K 31/5375* (2013.01)
USPC ............... 514/238.5; 514/239.5; 514/277; 514/331; 514/374; 514/406; 514/428; 514/475; 514/539; 514/543

(58) Field of Classification Search
None
See application file for complete search history.

(56) References Cited

U.S. PATENT DOCUMENTS

| | | | |
|---|---|---|---|
| 5,166,399 | A | 11/1992 | Schuetz et al. |
| 5,358,968 | A | 10/1994 | Oberdorf et al. |
| 6,444,850 | B1 | 9/2002 | Pak et al. |
| 6,653,258 | B1 | 11/2003 | Clough et al. |
| 2008/0280901 | A1 | 11/2008 | Kim et al. |

FOREIGN PATENT DOCUMENTS

| | | |
|---|---|---|
| CN | 1968687 A | 5/2007 |
| CN | 101205187 A | 6/2008 |
| CN | 101687019 A | 3/2010 |
| EP | 0 335 519 A1 | 10/1989 |
| JP | 63-216848 A | 9/1988 |
| JP | 01-308206 A | 12/1989 |
| JP | 02-273654 A | 11/1990 |
| JP | 05-170648 A | 7/1993 |
| JP | 06-239823 A | 8/1994 |
| JP | 08-291147 A | 11/1996 |
| JP | 10-512868 A | 12/1998 |
| JP | 2002-506060 A | 2/2002 |
| JP | 2002-511881 A | 4/2002 |
| JP | 2005-522500 A | 7/2005 |
| JP | 2008-503567 A | 2/2008 |
| JP | 2008-546815 A | 12/2008 |
| WO | 96/08969 A2 | 9/1995 |
| WO | WO 99/46216 A1 | 9/1999 |
| WO | WO 03/087032 A1 | 10/2003 |
| WO | 2004/084632 A1 | 10/2004 |
| WO | WO 2005/123054 A1 | 12/2005 |
| WO | 2007/104660 A2 | 9/2007 |
| WO | 2008/004798 A1 | 1/2008 |

OTHER PUBLICATIONS

Dequeker, J. Osteoporosis and arthritis. Annals of the Rheumatic Diseases. 49: (1990), 276-280.*
European Patent Office, European Search Report issued in corresponding EP Application No. 11 77 2255.3, dated Jan. 9, 2014.
Chinese Patent Office, Chinese Office Action issued in corresponding CN Application No. 201180003513.2, dated Sep. 2, 2013.
Japanese Patent Office, Japanese Office Action issued in corresponding JP Application No. 2012-525505, dated Sep. 24, 2013.

* cited by examiner

*Primary Examiner* — Alicia L Otton
(74) *Attorney, Agent, or Firm* — Sughrue Mion, PLLC

(57) ABSTRACT

The present invention relates to an alpha-arylmethoxyacrylate derivative, a preparation method thereof and a pharmaceutical composition comprising the same, and the alpha-arylmethoxyacrylate derivative is inhibitory of HIF, which plays an important role in the regulation of genes associated with energy metabolism, vasomotion, angiogenesis and apoptosis and in the response of cells under hypoxic conditions, so that it can be used for preventing or treating of diseases such as cancer, arthritis, psoriasis, diabetic retinopathy and macular degeneration.

8 Claims, 7 Drawing Sheets

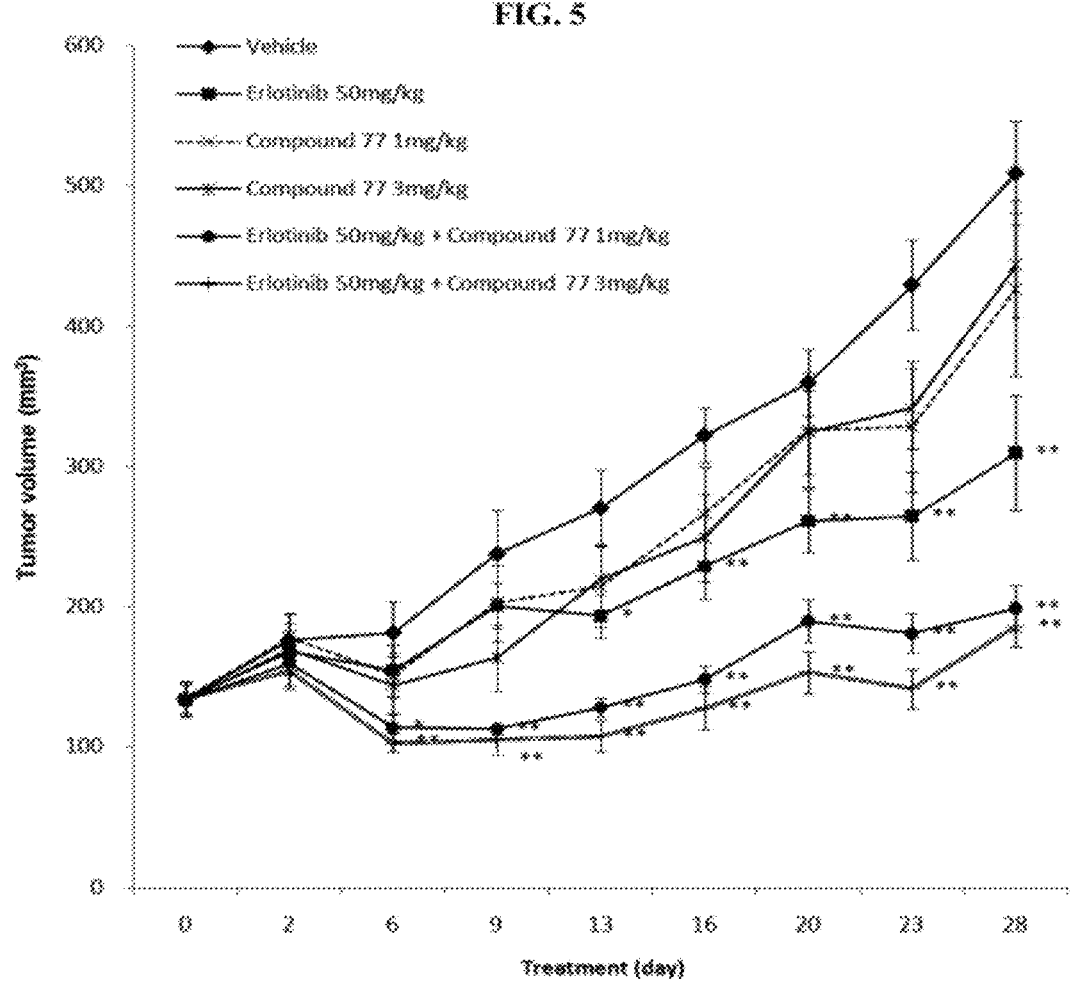

ALPHA-ARYLMETHOXYACRYLATE DERIVATIVE, PREPARATION METHOD THEREOF, AND PHARMACEUTICAL COMPOSITION CONTAINING SAME

FIELD OF THE INVENTION

The present invention relates to an alpha-arylmethoxyacrylate derivative and, more particularly, to a compound with inhibitory activity against hypoxia inducible factors to be used in the effective prophylaxis or therapy of cancer or angiogenesis-associated diseases. The present invention also relates to a method for preparing the compound, and a pharmaceutical composition comprising the compound.

BACKGROUND OF THE INVENTION

Hypoxia inducible factors (HIFs) are transcription factors induced under a hypoxic condition which play an important role in the expression regulation of genes associated with energy metabolism, vasomotion regulation, angiogenesis and apoptosis, and cellular responses to changes in available oxygen in the cellular environment. Among the genes whose expression levels are regulated by HIFs are angiogenesis factors (VEGF, FLT1), glucose transports (Glut-1, Glut-3), and enzymes that take part in glycolysis (*Nat. Rev. Cancer*, 2003, 3: 721-732; *J. Cell. Physiol.*, 2004, 200: 2030). The HIF transcription factor is a heterodimer comprised of two protein subunits, HIF-α and HIF-β. HIF-β is constitutively expressed while the expression of HIF-α is regulated by oxygen levels in the cellular environment. In the presence of normal oxygen tension, HIF-1α is hydroxylated at the two critical conserved proline residues of positions 402 and 564. Hydroxylated-HIF-1α can then bind the von Hippel-Lindau (VHL) tumor suppressor protein, which recruits the E3 ubiquitin-ligase complex to target the HIF-1α protein to promote proteasomal degradation. However, since oxygen is the rate-limiting co-factor for the hydroxylation, the prolyl hydroxylases are unable to hydroxylate HIF-1α at low oxygen tension. As a result, no VHL interaction occurs and the E3 ubiquitin-ligase complex is unable to target HIF-1α to proteasomal degradation, resulting in stabilization of HIF. Stabilized HIF-1α can then form a heterodimer with the HIF-1β, which is constitutively present within cells, and the heterodimer interacts with the hypoxia response element (HRE) on promoter regions of target genes, leading to the activation of hypoxia-responsive genes. In addition, the hydroxylation of an asparagine residue in the C-terminal transactivation domain (TAD) of HIF-1α (at position 803) by the factor inhibiting HIF-1 (FIH-1) negatively regulates the transcriptional activity of HIF by preventing its interaction with p300 and CBP transactivators. There are a large number of genes that have been known to be regulated by HIF, including genes associated with vascularization such as VEGF, Tie-2, Flt-1, Flk-1, PAI-1, EPO, and NOS, genes associated with metabolism under hypoxic conditions, such as GAPDH, Glut1, Glut3, LDH, HK-1, and HK-2, genes associated with apoptosis resistance, such as IGF-II, IGFBP-1, p21, NIP3, ADM, NOS2 and TGFA, and genes associated with the invasion and metastasis of tumor cells, such as SDF-1, CXCR4, β2 integrin, and prolyl-4-hydroxylase-α1.

Cancer refers comprehensively to diseases in which cells do not normally differentiate, but aberrantly grow to invade nearby parts of the body from its original site, thereby inhibiting normal functions of the tissues or organs. Particularly, rapidly propagating solid cancer takes place under hypoxic conditions because it is not supplied with as much oxygen and nutrients as it requires for its growth (*J. Natl. Cancer Inst.*, 1989, 82: 4-6). Because solid cancer cells are adapted to a low oxygen condition after being subjected to various genetic alterations, they become more malignant and resistant to anti-cancer agents. In fact, hypoxia is known to play an important role in malignant cancer in over 70% of all cancer types (*Nature*, 1997, 386: 403-407; *Semin. Oncol.*, 2001, 28: 36-41; *Nat. Med.*, 2000, 6: 1335-1340; *Cancer*, 2003, 97: 1573-1581).

When activated by hypoxia, HIF-1 induces the expression of various genes encoding, for example, hexokinase 2, glucose transporter 1, erythropoietin, IGF-2 (insulin-like growth factor-2), endoglin, VEGF (vascular endothelial growth factor), MMP-2 (matrix metalloprotease 2), uPAR (uPA receptor), MDR1 (p-glycoprotein), etc., leading to an improvement in apoptosis resistance, angiogenesis, cell proliferation, and invasiveness, thereby resulting in the malignant transformation of cancer cells. Particularly, HIF-1α is known to exist at a much higher level in tumor tissues than in normal tissues (*Cancer Res.*, 1999, 59: 5830-5835), and the expression level of HIF-1α is closely correlated with the clinical prognosis of cancer patients (*Drug Disc. Today*, 2007, 12: 853-859). Accordingly, it is well known that HIF inhibitors can be used as anticancer agents.

Based on this fact, active and extensive research has been conducted to develop anticancer agents targeting HIF (*Cancer Res.*, 2002, 62: 4316-4324; *Nat. Rev. Drug Disc.*, 2003, 2: 803-811; *Nat. Rev. Cancer*, 2003, 3: 721-732). Recently, a significant number of preexisting anticancer agents, such as taxol, rafamycin and 17-AAG (17-allylaminogeldanamycin), or small molecular compound YC-1 (guanylyl cyclase activator) are undergoing various clinical demonstrations to be used as HIF-1 inhibitors (*Nat. Rev. Drug Disc*, 2003, 2: 803-811; *Nat. Rev. Cancer*, 2003, 3: 721-732; *J. Natl. Cancer Inst.*, 2003, 95: 516-525; *Cancer Res.*, 62, 4316, 2002).

At the same time, HIF can be used as a target of therapeutics for diseases which are aggravated with angiogenesis as well as by cancer. Angiogenesis factors, such as VEGF, which are induced by HIF activated under hypoxic conditions are associated with the onset and progression of macular degeneration, diabetic retinopathy, arthritis and psoriasis as well as cancer. Hence, compounds inhibitory of HIF, which is activated by the hypoxic condition of the affected tissues, can be used as therapeutics for such diseases as macular degeneration, diabetic retinopathy, arthritis, etc. (*Pathology International*, 2005, 55: 603-610; *Ann. Rheum. Dis.*, 2003, 62: ii60-ii67). Particularly, HIF-1α is reported to be involved in inflammatory responses (*Cell*, 2003, 112: 645-657). Because a joint with inflammation is under a hypoxic condition and HIF promotes inflammation and cartilage destruction and plays an important role in angiogenesis necessary for the onset of arthritis, HIF has been suggested as a target for the development of arthritis drugs (*Ann. Rheum. Dis.*, 2005, 64: 971-980).

Leading to the present invention, intensive and thorough research into HIF inhibitors, conducted by the present inventors, resulted in the finding that specific α-arylmethoxyacrylate derivatives have excellent inhibitory activity against HIF.

SUMMARY OF THE INVENTION

Accordingly, it is an object of the present invention to provide a novel alpha-arylmethoxyacrylate derivative.

It is another object of the present invention to provide a pharmaceutical composition comprising the alpha-arylmethoxyacrylate derivative for preventing or treating cancer or angiogenesis-associated diseases.

It is a further object of the present invention to provide a method for preparing the alpha-arylmethoxyacrylate derivative.

In accordance with one aspect of the present invention, there is provided a compound selected from an alpha-arylmethoxyacrylate derivative of formula 1 and a pharmaceutically acceptable salt, a hydrate and a solvate thereof:

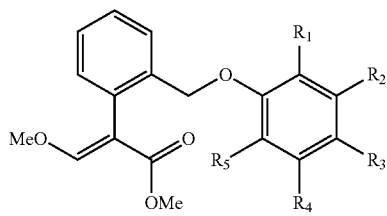

(1)

wherein $R_1$ and $R_5$ are each independently H, hydroxy, halogen, $C_{1-6}$alkyl, or $C_{1-6}$alkoxy;

$R_2$, $R_3$ and $R_4$ are each independently H, hydroxy, halogen, formyl, $C_{1-6}$alkyl, $C_{1-6}$alkoxy, $C_{3-6}$heteroaryl, or any one of formulae A to C

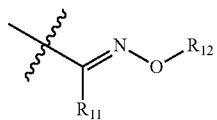

[formula A]

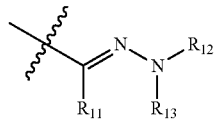

[formula B]

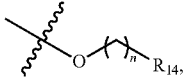

[formula C]

wherein n is an integer of 0 to 4;

$R_{11}$ is H, hydroxy, cyano, $C_{1-4}$alkyl, $C_{2-6}$alkenyl, $C_{1-6}$alkoxy, $C_{1-4}$alkoxyC$_{1-4}$alkyl, $C_{3-8}$cycloalkylC$_{1-4}$alkyl, or $C_{2-7}$heterocycloalkylC$_{1-4}$alkyl, $C_{1-4}$alkylamino, or diC$_{1-4}$alkylamino;

$R_{12}$ and $R_{13}$ are each independently H, halogen, $C_{1-6}$alkyl, $C_{2-6}$alkenyl, $C_{2-6}$alkynyl, $C_{3-8}$cycloalkyl, $C_{3-8}$cycloalkylC$_{1-4}$alkyl, $C_{2-7}$heterocycloalkylC$_{1-4}$alkyl, $C_{6-12}$aryl, $C_{6-12}$arylC$_{1-4}$alkyl, $C_{6-12}$aryloxyC$_{1-4}$alkyl, or $C_{3-6}$heteroarylC$_{1-4}$alkyl, or combine together to form $C_{2-7}$heterocycloalkyl; and $R_{14}$ is H, hydroxy, $C_{3-8}$cycloalkyl, $C_{2-7}$heterocycloalkyl, $C_{6-12}$aryl, $C_{6-12}$arylC$_{1-4}$alkyl, $C_{6-12}$aryloxy, $C_{3-6}$heteroaryl, $C_{1-4}$alkylamino, diC$_{1-4}$alkylamino, or

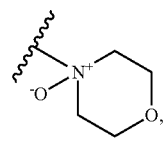

said alkyl, alkenyl and alkoxy each independently being optionally substituted with one or more substituents selected from the group consisting of hydroxy, halogen, nitro and cyano;

said cycloalkyl, heterocycloalkyl, aryl and heteroaryl each independently being optionally substituted with one or more substituents selected from the group consisting of halogen, nitro, cyano, $C_{1-4}$alkyl and $C_{1-4}$alkoxy; and said heterocycloalkyl and heteroaryl each independently comprising at least one atom of N and O.

In accordance with another aspect of the present invention, there is provided a pharmaceutical composition for preventing or treating cancer, arthritis, psoriasis, diabetic retinopathy or macular degeneration, comprising the alpha-arylmethoxyacrylate derivative of formula 1, or a pharmaceutically acceptable salt, a hydrate or a solvate thereof, as an active ingredient.

In accordance with a further aspect of the present invention, there is provided a method for preparing the alpha-arylmethoxyacrylate derivative of formula 1, comprising the step of reacting a compound of formula 2 with a compound of formula 3 in the presence of a base:

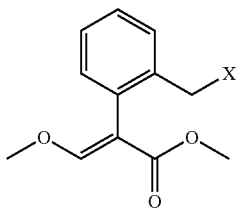

(2)

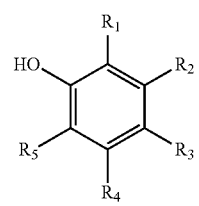

(3)

wherein, X is halogen, and $R_1$ to $R_5$ have the same meaning as defined above.

The alpha-arylmethoxyacrylate derivative and the pharmaceutical composition comprising the same in accordance with the present invention are inhibitory of HIF, which plays an important role in the regulation of genes associated with energy metabolism, vasomotion, angiogenesis and apoptosis and in the response of cells under hypoxic conditions, so that they can be used for preventing or treating of diseases such as cancer, arthritis, psoriasis, diabetic retinopathy and macular degeneration.

BRIEF DESCRIPTION OF THE DRAWINGS

The above and other objects and features of the present invention will become apparent from the following description of the invention, when taken in conjunction with the accompanying drawings, which show:

FIG. 5: a graph showing the inhibitory activity of the compound of the present invention against the growth of human pancreatic cancer cells in nude mice administered with the compound (statistical significance to vehicle-administered group (Student t-test)* p<0.05, ** p<0.01).

DETAILED DESCRIPTION OF THE INVENTION

Figure 1A:
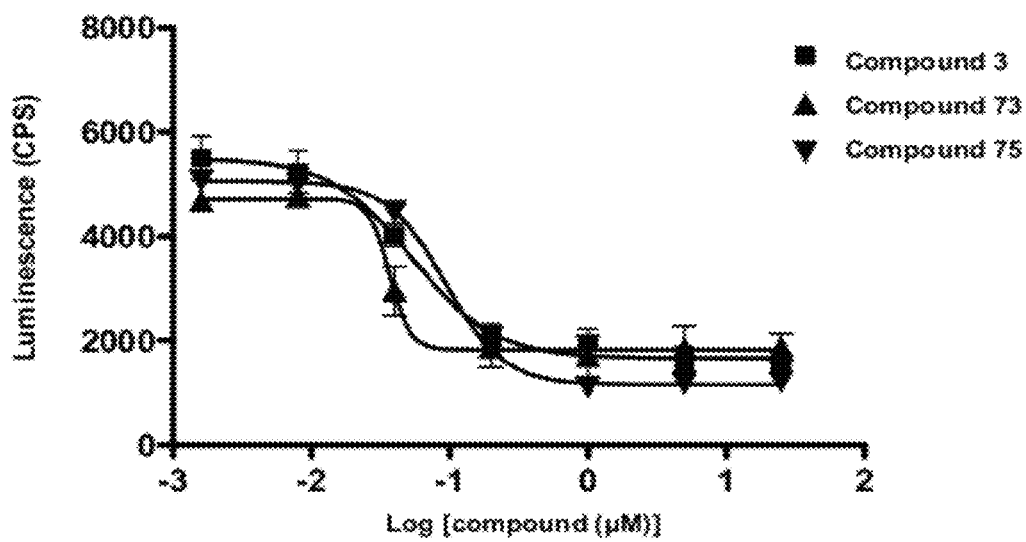
FIGS. 1A to 1C: luciferase reporter activity measured in the HIF reporter cell line which has been incubated with the compounds of the present invention for 6 hours under a 1% oxygen condition.

Hereinafter, the present invention is described in detail

As used herein, the term "halogen" refers to fluorine, chlorine, bromine or iodine.

The term "alkyl" refers to a saturated aliphatic hydrocarbon, whether linear or branched. Examples of alkyl include methyl, ethyl, n-propyl, isopropyl, n-butyl, i-butyl, and tert-butyl.

The term "alkenyl" refers to an unsaturated hydrocarbon with one or more double bonds, whether linear or branched. Examples of alkenyl include ethenyl, n-propenyl, propenyl, n-butenyl, and i-butenyl.

The term "alkynyl" refers to an unsaturated hydrocarbon with one or more triple bonds, whether linear or branched. Examples of alkynyl include ethynyl, propynyl, butynyl, i-pentynyl, and t-pentynyl.

The term "alkoxy" refers to an —OR group (wherein R is "alkyl" as defined above). Examples of alkoxy include methoxy, ethoxy, n-propoxy, isopropoxy, n-butoxy, tert-butoxy, sec-butoxy, n-pentoxy, and 1,2-dimethylbutoxy.

The teem "cycloalkyl" refers to a non-aromatic single or multiple hydrocarbon ring. Examples of cycloalkyl include cyclopropyl, cyclobutyl, cyclopentyl, and cyclohexyl.

The term "heterocycloalkyl" refers to a non-aromatic single or multiple hydrocarbon ring containing at least one heteroatom such as N, O or S. Examples of heterocycloalkyl include aziridinyl, pyrrolidinyl, pyrrolidono, piperidinyl, piperidino, piperazinyl, piperazino, morpholinyl, morpholino, tetrahydrofuranyl, and pyranyl.

The term "alkylamino" refers to a —NHR' group wherein R' is an alkyl group as defined above.

The term "dialkylamino" refers to a —NR'R" group wherein R' and R" are an alkyl group as defined above.

The term "aryl" refers to an aromatic hydrocarbon. Examples of aryl include phenyl, naphthyl, indenyl, azulenyl, fluorenyl, and anthracenyl.

The term "heteroaryl" refers to an aromatic ring containing at least one heteroatom such as N, O or S. Examples of heteroaryl include furanyl, thienyl, pyrolyl, thiazolyl, oxazolyl, imidazolyl, pyrazolyl, isoxazolyl, isothiazolyl, triazolyl, oxadiazolyl, thiadiazolyl, pyranyl, pyridinyl, pyridazinyl, pyrimidinyl, pyrazinyl, triazinyl, tetrazinyl, indolyl, isoindolyl, benzofuranyl, benzothiophenyl, benzoimidazolyl, benzthiazolyl, purinyl, quinazolinyl, quinolinyl, isoquinolinyl, and carbazolyl.

The alkyl, alkenyl, alkynyl, cycloalkyl, heterocycloalkyl, alkylamino, aryl and heteroaryl groups may be substituted with one or more suitable substituents.

The present invention provides a compound selected from an alpha-arylmethoxyacrylate derivative of formula 1 and a pharmaceutically acceptable salt, a hydrate and a solvate thereof.

In formula 1, preferably, $R_1$ and $R_5$ are each independently H, methyl, methoxy, or fluoro.

Further, at least one of $R_2$, $R_3$ and $R_4$ is preferably selected from formulae A to C.

In formulae A to C, preferably, $R_{12}$ and $R_{13}$ are each independently H, methyl, ethyl, propyl, cyclopropylmethyl, cyclopentyl, oxirane-2-ylmethyl, pyrrolidinylethyl, piperidinylethyl, phenyl, benzyl, 4-methylbenzyl, 3-methoxybenzyl, phenoxyethyl, phenethyl, pyridin-2-ylmethyl or pyridin-4-ylmethyl, or combine together to form morpholino.

Preferably, n is 1 or 2; and $R_{14}$ is hydroxy, morpholino, phenyl, phenoxy, pyridin-2-yl, pyridin-4-yl, 4-nitrophenyl,

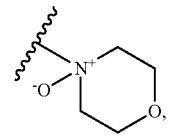

or hydroxyethylamino.

Exemplary alpha-arylmethoxyacrylate derivatives of formula 1 in accordance with the present invention are listed as the following compounds 1 to 82:

1) (E)-methyl 2-(2-((2,5-dimethyl-4-((E)-1-(propoxyimino) propyl)phenoxy)-methyl)phenyl)-3-methoxyacrylate (compound 1);
2) (E)-methyl 2-(2-((2,5-dimethyl-4-((E)-1-(propoxyimino) ethyl)phenoxy)methyl)-phenyl)-3-methoxyacrylate (compound 2);
3) (E)-methyl 2-(2-((3-(benzyloxy)phenoxy)methyl)phenyl)-3-methoxyacrylate (compound 3);
4) (E)-methyl 2-(2-((3-((E)-(ethoxyimino)methyl)phenoxy) methyl)phenyl)-3-methoxyacrylate (compound 4);
5) (E)-methyl 2-(2((5-hydroxyphenoxy)methyl)phenyl)-3-methoxyacrylate (compound 5);
6) (E)-methyl 2-(2-((5-formyl-2-methoxyphenoxy)methyl) phenyl)-3-methoxyacrylate (compound 6);
7) (E)-methyl 2-(2-((3-((E)-1-(propoxyimino)propyl)phenoxy)methyl)phenyl)-3-methoxyacrylate (compound 7);
8) (E)-methyl 2-(2-((4-((E)-1-(propoxyimino)ethyl)phenoxy)methyl)phenyl)-3-methoxyacrylate (compound 8);
9) (E)-methyl 2-(2-((4-((E)-1-(2-(piperidin-1-yl)ethoxyimino)ethyl)phenoxy)-methyl)phenyl)-3-methoxyacrylate (compound 9);
10) (E)-methyl 3-methoxy-2-(2-((3-((E)-(2-(piperidin-1-yl) ethoxyimino)methyl)-phenoxy)methyl)phenyl)acrylate (compound 10);
11) (E)-methyl 2-(2-((3-(2-(2-hydroxyethylamino)ethoxy) phenoxy)methyl)phenyl)-3-methoxyacrylate (compound 11);
12) (E)-methyl 2-(2-((3-(2-hydroxyethoxy)phenoxy)methyl) phenyl)-3-methoxyacrylate (compound 12);

13) (E)-4-(2-(3-(2-(1,3-dimethoxy-3-oxoprop-1-en-2-yl)benzyloxy)phenoxy)ethyl)-morpholine 4-oxide (compound 13)
14) (E)-methyl 3-methoxy-2-(2-((3-((E)-(propoxyimino)methyl)phenoxy)methyl)-phenyl)acrylate (compound 14);
15) (E)-methyl 2-(2-((3-fluoro-5-hydroxyphenoxy)methyl)phenyl)-3-methoxyacrylate (compound 15);
16) (E)-methyl 2-(2-((3-phenethoxyphenoxy)methyl)phenyl)-3-methoxyacrylate (compound 16);
17) (E)-methyl 2-(2-((4-((E)-1-(benzyloxyimino)ethyl)phenoxy)methyl)phenyl)-3-methoxyacrylate (compound 17);
18) (E)-methyl 2-(2-((4-((E)-1-(phenethoxyimino)ethyl)phenoxy)methyl)phenyl)-3-methoxyacrylate (compound 18);
19) (E)-methyl 2-(2((4-fluorophenoxy)methyl)phenyl)-3-methoxyacrylate (compound 19);
20) (E)-methyl 2-(2-((3-hydroxy-5-(2-phenoxyethoxy)phenoxy)methyl)phenyl)-3-methoxyacrylate (compound 20);
21) (E)-methyl 2-(2-((3-(benzyloxy)-5-fluorophenoxy)methyl)phenyl)-3-methoxyacrylate (compound 21);
22) (E)-methyl 2-(2-((3-fluoro-5-(2-phenoxyethoxy)phenoxy)methyl)phenyl)-3-methoxyacrylate (compound 22);
23) (E)-methyl 2-(2-((3-fluoro-5-(pyridin-2-ylmethoxy)phenoxy)methyl)phenyl)-3-methoxyacrylate (compound 23);
24) (E)-methyl 2-(2-((3-fluoro-5-(4-nitrobenzyloxy)phenoxy)methyl)phenyl)-3-methoxyacrylate (compound 24);
25) (E)-methyl 3-methoxy-2-(2-((3-((E)-(morpholinoimino)methyl)phenoxy)-methyl)phenyl)acrylate (compound 25);
26) (E)-methyl 2-(2-((3-(pyridin-2-ylmethoxy)phenoxy)methyl)phenyl)-3-methoxyacrylate (compound 26);
27) (E)-methyl 2-(2-((3-(pyridin-4-ylmethoxy)phenoxy)methyl)phenyl)-3-methoxyacrylate (compound 27);
28) (E)-methyl 2-(2-((3-hydroxy-5-(pyridin-2-ylmethoxy)phenoxy)methyl)phenyl)-3-methoxyacrylate (compound 28);
29) (E)-methyl 2-(2-((3-hydroxy-5-(pyridin-4-ylmethoxy)phenoxy)methyl)phenyl)-3-methoxyacrylate (compound 29);
30) (E)-methyl 2-(2-((2,5-dimethyl-4-((E)-1-(morpholinoimino)propyl)phenoxy)-methyl)phenyl)-3-methoxyacrylate (compound 30);
31) (E)-methyl 2-(2-((4-((E)-(hydroxyimino)methyl)-2-methylphenoxy)methyl)-phenyl)-3-methoxyacrylate (compound 31);
32) (E)-methyl 2-(2-((2-methyl-4-((E)-(propoxyimino)methyl)phenoxy)methyl)-phenyl)-3-methoxyacrylate (compound 32);
33) (E)-methyl 2-(2-((4-((E)-(benzyloxyimino)methyl)-2-methylphenoxy)methyl)-phenyl)-3-methoxyacrylate (compound 33);
34) (E)-methyl 2-(2-((4-((E)-1-(hydroxyimino)ethyl)-2-methoxyphenoxy)methyl)-phenyl)-3-methoxyacrylate (compound 34);
35) (E)-methyl 2-(2-((4-((E)-1-(propoxyimino)ethyl)-2-methoxyphenoxy)methyl)-phenyl)-3-methoxyacrylate (compound 35);
36) (E)-methyl 2-(2-((4-((E)-1-(benzyloxyimino)ethyl)-2-methoxyphenoxy)-methyl)phenyl)-3-methoxyacrylate (compound 36);
37) (E)-methyl 2-(2-((5-((E)-1-(hydroxyimino)ethyl)-2-methoxyphenoxy)methyl)-phenyl)-3-methoxyacrylate (compound 37);
38) (E)-methyl 2-(2-((5-((E)-1-(benzyloxyimino)ethyl)-2-methoxyphenoxy)methyl)-phenyl)-3-methoxyacrylate (compound 38);
39) (E)-methyl 2-(2-((5-((E)-(benzyloxyimino)methyl)-2-methoxyphenoxy)-methyl)phenyl)-3-methoxyacrylate (compound 39);
40) (E)-methyl 2-(2-((2,5-dimethyl-3-propoxyphenoxy)methyl)phenyl)-3-methoxyacrylate (compound 40);
41) (E)-methyl 2-(2-((3-(benzyloxy)-2,5-dimethylphenoxy)methyl)phenyl)-3-methoxyacrylate (compound 41);
42) (E)-methyl 2-(2-((2-methoxy-5-((E)-1-(propoxyimino)ethyl)phenoxy)methyl)-phenyl)-3-methoxyacrylate (compound 42);
43) (E)-methyl 2-(2-((2-methoxy-5-((E)-(propoxyimino)methyl)phenoxy)methyl)-phenyl)-3-methoxyacrylate (compound 43);
44) (E)-methyl 2-(2-((2-methoxy-5-((E)-1-(phenylethoxyimino)ethyl)phenoxy)-methyl)phenyl)-3-methoxyacrylate (compound 44);
45) (E)-methyl 2-(2-((2-methoxy-5-((E)-1-(phenylethoxyimino)methyl)phenoxy)-methyl)phenyl)-3-methoxyacrylate (compound 45);
46) (E)-methyl 2-(2-((2-methoxy-5-((E)-1-(phenoxyimino)methyl)phenoxy)-methyl)phenyl)-3-methoxyacrylate (compound 46);
47) (E)-methyl 2-(2-((3-((E)-1-(phenoxyimino)methyl)phenoxy)methyl)phenyl)-3-methoxyacrylate (compound 47);
48) (E)-methyl 2-(2-((2-methoxy-5-((E)-1-(phenylhydrazono)ethyl)phenoxy)-methyl)phenyl)-3-methoxyacrylate (compound 48);
49) (E)-methyl 2-(2-((2,5-dimethyl-4-((E)-(propoxyimino)methyl)phenoxy)-methyl)phenyl)-3-methoxyacrylate (compound 49);
50) (E)-methyl 2-(2-((4-((E)-(benzyloxyimino)methyl)-2,5-dimethylphenoxy)-methyl)phenyl)-3-methoxyacrylate (compound 50);
51) (E)-methyl 2-(2-((2,5-dimethyl-4-((E)-(2-phenoxyethoxyimino)methyl)-phenoxy)methyl)phenyl)-3-methoxyacrylate (compound 51);
52) (E)-methyl 2-(2-((2,5-dimethyl-4-((E)-(oxirane-2-ylmethoxyimino)methyl)-phenoxy)methyl)phenyl)-3-methoxyacrylate (compound 52);
53) (E)-methyl 2-(2-((2,5-dimethyl-4-((E)-(2-(pyrrolidin-1-yl)ethoxyimino)-methyl)phenoxy)methyl)phenyl)-3-methoxyacrylate (compound 53);
54) (E)-methyl 2-(2-((2,5-dimethyl-4-((E)-(2-(piperidin-1-yl)ethoxyimino)methyl)-phenoxy)methyl)phenyl)-3-methoxyacrylate (compound 54);
55) (E)-methyl 2-(2-((3-hydroxy-2,5-dimethylphenoxy)methyl)phenyl)-3-methoxyacrylate (compound 55);
56) (E)-methyl 2-(2-((2,5-dimethyl-3-(2-phenoxyethoxy)phenoxy)methyl)phenyl)-3-methoxyacrylate (compound 56);
57) (E)-methyl 2-(2-((2-methoxy-5-((E)-1-(4-methylbenzyloxyimino)ethyl)-phenoxy)methyl)phenyl)-3-methoxyacrylate (compound 57);
58) (E)-methyl 2-(2-((2-methoxy-5-((E)-1-(4-methylbenzyloxyimino)methyl)-phenoxy)methyl)phenyl)-3-methoxyacrylate (compound 58);
59) (E)-methyl 2-(2-((2-methyl-4-((E)-(phenylethoxyimino)methyl)phenoxy)-methyl)phenyl)-3-methoxyacrylate (compound 59);
60) (E)-methyl 2-(2-((2-methyl-4-((E)-(4-methylbenzyloxyimino)methyl)phenoxy)-methyl)phenyl)-3-methoxyacrylate (compound 60);
61) (E)-methyl 2-(2-((4-((E)-(benzyloxyimino)methyl)-2-fluoro-6-methoxyphenoxy)methyl)phenyl)-3-methoxyacrylate (compound 61);
62) (E)-methyl 2-(2-((3-(benzyloxy)-2,4-difluorophenoxy)methyl)phenyl)-3-methoxyacrylate (compound 62);

63) (E)-methyl 2-(2-((2,5-dimethyl-4-((E)-(phenoxyimino)methyl)phenoxy)-methyl)phenyl)-3-methoxyacrylate (compound 63);
64) (E)-methyl 2-(2-((2-fluoro-6-methoxy-4-((E)-(propoxyimino)methyl)phenoxy)-methyl)phenyl)-3-methoxyacrylate (compound 64);
65) (E)-methyl 2-(2-((2,4-difluoro-3-propoxyphenoxy)methyl)phenyl)-3-methoxyacrylate (compound 65);
66) (E)-methyl 2-(2-((2-fluoro-6-methoxy-4-((E)-(phenethoxyimino)methyl)-phenoxy)methyl)phenyl)-3-methoxyacrylate (compound 66);
67) (E)-methyl 2-(2-((4-((E)-(cyclopropylmethoxyimino)methyl)-2-methylphenoxy)methyl)phenyl)-3-methoxyacrylate (compound 67);
68) (E)-methyl 2-(2-((4-((E)-(cyclopropylmethoxyimino)methyl)-2,5-dimethylphenoxy)methyl)phenyl)-3-methoxyacrylate (compound 68);
69) (E)-methyl 2-(2-((4-((E)-(cyclopentyloxyimino)methyl)-2,5-dimethylphenoxy)-methyl)phenyl)-3-methoxyacrylate (compound 69);
70) (E)-methyl 2-(2-((4-((E)-(cyclopentyloxyimino)methyl)-2-methylphenoxy)-methyl)phenyl)-3-methoxyacrylate (compound 70);
71) (E)-methyl 2-(2-((2,5-dimethyl-4-((E)-(3-phenoxypropyloxyimino)methyl)-phenoxy)methyl)phenyl)-3-methoxyacrylate (compound 71);
72) (E)-methyl 2-(2-((4-((E)-(3-methoxybenzyloxyimino)methyl)-2,5-dimethylphenoxy)methyl)phenyl)-3-methoxyacrylate (compound 72);
73) (E)-methyl 2-(2-((4-((E)-(pyridin-2-ylmethoxyimino)methyl)-2,5-dimethylphenoxy)methyl)phenyl)-3-methoxyacrylate (compound 73);
74) (E)-methyl 2-(2-((4-((E)-(pyridin-4-ylmethoxyimino)methyl)-2,5-dimethylphenoxy)methyl)phenyl)-3-methoxyacrylate (compound 74);
75) (E)-methyl 2-(2-((3-((E)-(2-phenoxyethoxyimino)methyl)phenoxy)methyl)-phenyl)-3-methoxyacrylate (compound 75);
76) (E)-methyl 2-(2-((3-(2-morpholinoethoxy)phenoxy)methyl)phenyl)-3-methoxyacrylate (compound 76);
77) (E)-methyl 2-(2-((2,5-dimethyl-4-((E)-1-(methoxyimino)ethyl)phenoxy)-methyl)phenyl)-3-methoxyacrylate (compound 77);
78) (E)-methyl 2-(2-((2,5-dimethyl-4-((E)-1-(ethoxyimino)ethyl)phenoxy)methyl)-phenyl)-3-methoxyacrylate (compound 78);
79) (E)-methyl 2-(2-((2,5-dimethyl-4-((E)-1-(pyridin-2-ylmethoxyimino)ethyl)-phenoxy)methyl)phenyl)-3-methoxyacrylate (compound 79);
80) (E)-methyl 3-methoxy-2-(2-((4-((Z)-2-methoxy-1-(methoxyimino)ethyl)2,5-dimethylphenoxy)methyl)phenyl)acrylate (compound 80);
81) (E)-methyl 3-methoxy-2-(2-((2,5-dimethyl-4-(oxazol-5-yl)phenoxy)methyl)-phenyl)acrylate (compound 81); and
82) (E)-methyl 3-methoxy-2-(2-((2,5-dimethyl-4-(1-methyl-1H-pyrazol-3-yl)-phenoxy)methyl)phenyl)acrylate (compound 82).

Among compounds 1 to 82, most exemplary compounds are listed as below:

1) (E)-methyl 2-(2-((2,5-dimethyl-4-((E)-1-(propoxyimino)propyl)phenoxy)-methyl)phenyl)-3-methoxyacrylate (compound 1);
2) (E)-methyl 2-(2-((2,5-dimethyl-4-((E)-1-(propoxyimino)ethyl)phenoxy)methyl)-phenyl)-3-methoxyacrylate (compound 2);
3) (E)-methyl 2-(2-((3-(benzyloxy)phenoxy)methyl)phenyl)-3-methoxyacrylate (compound 3);
4) (E)-methyl 2-(2-((4-((E)-(cyclopropylmethoxyimino)methyl)-2,5-dimethylphenoxy)methyl)phenyl)-3-methoxyacrylate (compound 68);
5) (E)-methyl 2-(2-((4-((E)-(cyclopentyloxyimino)methyl)-2,5-dimethylphenoxy)-methyl)phenyl)-3-methoxyacrylate (compound 69);
6) (E)-methyl 2-(2-((4-((E)-(pyridin-2-ylmethoxyimino)methyl)-2,5-dimethylphenoxy)methyl)phenyl)-3-methoxyacrylate (compound 73);
7) (E)-methyl 2-(2-((3-((E)-(2-phenoxyethoxyimino)methyl)phenoxy)methyl)-phenyl)-3-methoxyacrylate (compound 75);
8) (E)-methyl 2-(2-((3-(2-morpholinoethoxy)phenoxy)methyl)phenyl)-3-methoxyacrylate (compound 76);
9) (E)-methyl 2-(2-((2,5-dimethyl-4-((E)-1-(methoxyimino)ethyl)phenoxy)methyl)-phenyl)-3-methoxyacrylate (compound 77);
10) (E)-methyl 2-(2-((2,5-dimethyl-4-((E)-1-(ethoxyimino)ethyl)phenoxy)methyl)-phenyl)-3-methoxyacrylate (compound 78);
11) (E)-methyl 2-(2-((2,5-dimethyl-4-((E)-1-(pyridin-2-ylmethoxyimino)ethyl)-phenoxy)methyl)phenyl)-3-methoxyacrylate (compound 79);
12) (E)-methyl 3-methoxy-2-(2-((4-((Z)-2-methoxy-1-(methoxyimino)ethyl)2,5-dimethylphenoxy)methyl)phenyl)acrylate (compound 80);
13) (E)-methyl 3-methoxy-2-(2-((2,5-dimethyl-4-(oxazol-5-yl)phenoxy)methyl)-phenyl)acrylate (compound 81); and
14) (E)-methyl 3-methoxy-2-(2-((2,5-dimethyl-4-(1-methyl-1H-pyrazol-3-yl)-phenoxy)methyl)phenyl)acrylate (compound 82).

Pharmaceutically acceptable salts of the α-arylmethoxyacrylate derivatives of formula 1 fall within the scope of the present invention. The term "pharmaceutically acceptable salts", as used herein, means alkali metal salts, alkaline earth metal salts, ammonium salts, amine salts, acid addition salts, and hydrate salts. Preferred are non-toxic and soluble salts. Examples of preferable salts include alkali metal salts such as potassium salts and sodium salts; alkaline earth metal salts such as calcium salts and magnesium salts; ammonium salts; amine salts such as tetramethyl ammonium salts, triethylamine salts, methylamine salts, dimethylamine salts, cyclopentylamine salts, benzyl amine salts, phenethylamine salts, piperidine salts, monoethanolamine salts, diethanolamine salts, tris(hydroxymethyl)aminomethane salts, lysine salts, arginine salts, and N-methyl-D-glucamine salts; inorganic acid salts such as hydrogen chloride salts, hydrogen bromide salts, hydrogen iodide salts, sulfuric acid salts, phosphoric acid salts, and nitric acid salts; and organic acid salts such as acetic acid salts, lactic acid salts, tartaric acid salts, tannic acid salts, malic acid salts, succinic acid salts, fumaric acid salts, benzoic acid salts, citric acid salts, methane sulfonic acid salts, ethane sulfonic acid salts, benzene sulfonic acid salts, toluene sulfonic acid salts, isethionic acid salts, glucuronic acid salts, gluconic acid salts, and fatty acid salts.

In addition, hydrate or solvate forms of alpha-arylmethoxyacrylate derivatives of formula 1 also fall within the scope of the invention. These hydrates or solvates may be prepared using well-known methods and are preferably non-toxic and water soluble. Preferred are hydrates or solvates bound with 1 to 5 water or alcoholic solvent (particularly, ethanol) molecules.

Moreover, the present invention provides a pharmaceutical composition for preventing or treating cancer, arthritis, psoriasis, diabetic retinopathy or macular degeneration, comprising the alpha-arylmethoxyacrylate derivative of formula 1, or a pharmaceutically acceptable salt, a hydrate or a solvate thereof, as an active ingredient.

Examples of the cancer treatable with the pharmaceutical composition include bladder cancer, breast cancer, colorectal cancer, uterine cancer, head and neck cancer, leukemia, lung cancer, lymphoma, melanoma, non-small cell lung cancer, ovary cancer, prostate cancer, testis cancer, thyroid cancer, stomach cancer, brain cancer, Ewing's sarcoma, Hodgkin's lymphoma, liver cancer, medulloblastoma, neuroblastoma, non-Hodgkin's lymphoma, osteosarcoma, retinoblastoma, glioma, Wilm's tumor, esophageal cancer, oral cancer, kidney cancer, multiple myeloma, pancreatic cancer, skin cancer and small cell lung cancer. The arthritis may be rheumatoid arthritis or degenerative arthritis.

The pharmaceutical composition comprising the compound of the present invention may further comprise a pharmaceutically acceptable carrier. The pharmaceutical acceptable carrier useful in the present invention may include conventional excipients, disintegrants, sweeteners, lubricants, and flavorants. Meanwhile, the pharmaceutical composition may be formulated into various dosage forms such as tablets, capsules, powders, granules, suspensions, emulsions, syrups, injections, etc., or single or multiple dosage forms such as non-oral formulations.

Depending on the purpose of administration, the pharmaceutical composition may take various oral or non-oral routes. For non-oral administration, the daily dose of the active ingredient, whether in a single dose or in multiple doses, may be on the order of from 0.01 to 40 mg/kg body weight, preferably on the order of from 0.5 to 5 mg/kg body weight, and more preferably on the order of from 1 to 4 mg/kg body weight. Orally, the active ingredient may be administered in a single dose or in multiple doses at a daily dose of from 0.1 to 400 mg/kg body weight, preferably at a daily dose of from 5 to 50 mg/kg body weight and more preferably at a daily dose of from 10 to 40 mg/kg body weight. The administration dosage of the active ingredient may vary depending on various factors including the patient's weight, age, gender, state of health, diet, the time of administration, the route of administration, excretion rate, severity of the disease, etc.

Further, the present invention provides a use of the alpha-arylmethoxyacrylate derivative of formula 1, or a pharmaceutical acceptable salt, a hydrate or a solvate thereof for the preparation of a medicament for preventing or treating cancer, arthritis, psoriasis, diabetic retinopathy or macular degeneration.

In addition, the present invention provides a method for preventing or treating arthritis, psoriasis, diabetic retinopathy or macular degeneration in a subject in need thereof, comprising administering to the subject an alpha-arylmethoxyacrylate derivative of formula 1 or a pharmaceutically acceptable salt, a hydrate or a solvate thereof.

Moreover, the present invention provides a method for preparing the alpha-arylmethoxyacrylate derivative of formula 1, comprising reacting a compound of formula 2 with a compound of formula 3 in the presence of a base.

For the preparation of the compound of formula 2, used as one starting material in the preparation method, the method of Korean Patent No. 0624238 or European Patent No. 278,595 may be employed while the other starting material of the compound of formula 3 may be prepared using a conventional method, for example, the method disclosed in [*The national academy of science of the united states of America*, (2008), 105(1), 174-179, Abbott laboratories].

Particularly, the compound of formula 3 wherein $R_2$ is hydrogen and $R_3$ is represented by formula A (compound 3a) or vice versa may be prepared as Reaction Scheme 1.

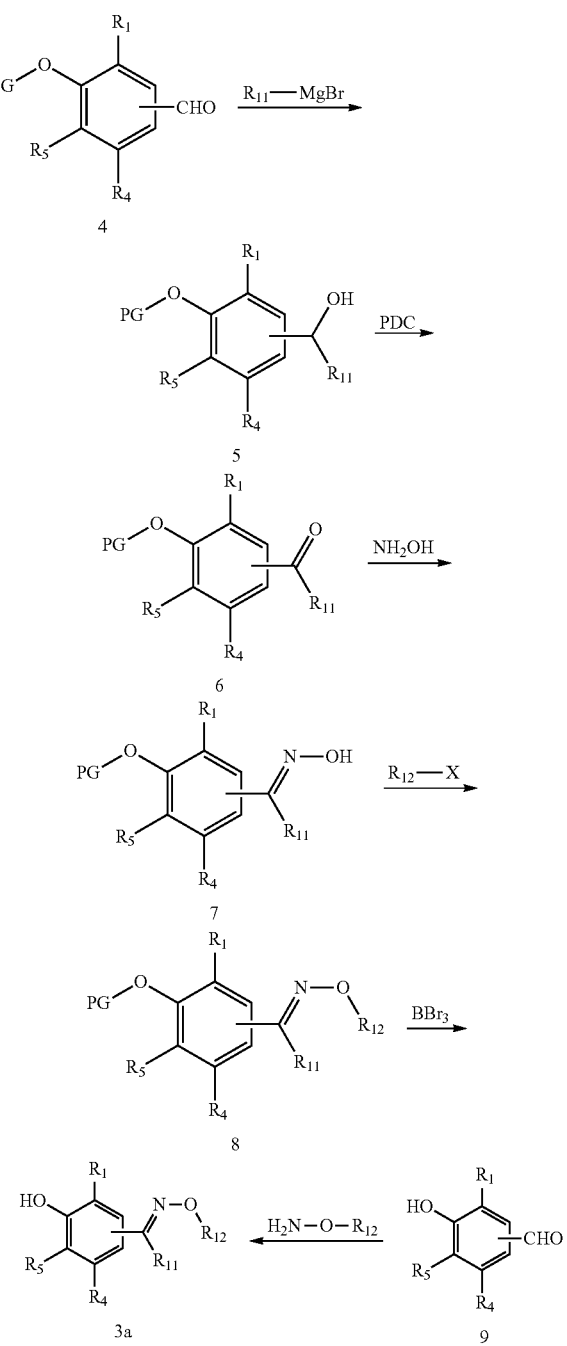

wherein $R_1$, $R_4$, $R_5$, $R_{11}$ and $R_{12}$ have the same meaning as defined above; PG is methyl, benzyl or trialkylsilyl (for example, trimethylsilyl, triethylsilyl, triisopropylsilyl or t-butyldimethylsilyl).

First, the compound of formula 4 is allowed to undergo a Grignard reaction (*Tetrahedron Lett.*, (1975), 1465) with alkylmagnesium bromide according to the conventional chemical coupling method disclosed in [*The national academy of science of the united states of America*, (2008), 105(1), 174-179, Abbott laboratories] to give the compound of formula 5, followed by reduction with PDC (pyridinium dichromate, *Tetrahedron Lett.*, (1984), 1061) to afford the compound of formula 6. This compound is typically reacted with hydroxylamine to produce the compound of formula 7, an oxime compound (U.S. Pat. No. 5,358,968). Alkylation of the oxime compound with alkyl halide is performed using a conventional method to obtain the compound of formula 8 which is then converted into the compound of formula 3a, a phenol derivative (*Tetrahedron Letters,* 40(1999) 4327-4330), in the presence of boron tribromide (U.S. Pat. No. 5,358,968).

Alternatively, the aldehyde compound of formula 9 may be reacted with O-alkylamine to produce the compound of formula 3a.

The compound of formula 3 wherein one of $R_2$ and $R_3$ is hydrogen with the proviso that the other is represented by formula A (compound 3b) may be prepared as Reaction Scheme 2.

[Reaction Scheme 2]

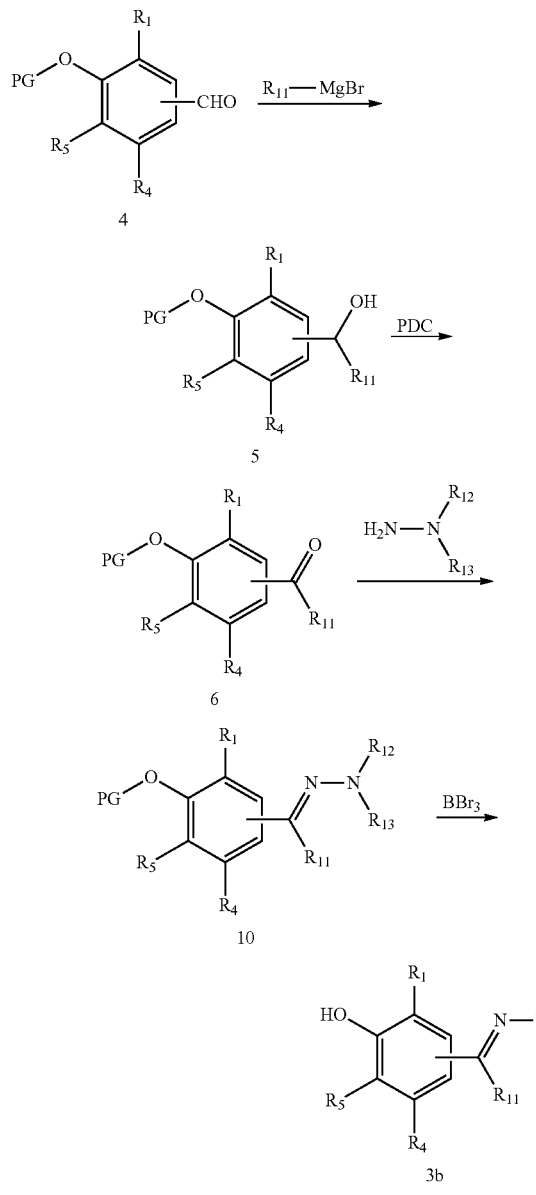

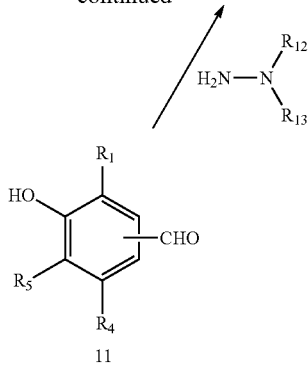

wherein $R_1$, $R_4$, $R_5$, $R_{11}$, $R_{12}$ and $R_{13}$ have the same meaning as defined above; PG is methyl, benzyl or trialkylsilyl (for example, trimethylsilyl, triethylsilyl, triisopropylsilyl or t-butyldimethylsilyl).

First, the compound of formula 4 is allowed to undergo a Grignard reaction (*Tetrahedron Lett.*, (1975), 1465) with alkylmagnesium bromide according to the conventional chemical coupling method disclosed in [*The national academy of science of the united states of America* (2008), 105(1), 174-179, Abbott laboratories] to give the compound of formula 5, followed by reduction into the compound of formula 6 in the presence of PDC (pyridinium dichromate, *Tetrahedron Lett.*, (1984), 1061). This compound is typically reacted with hydrazine to form the compound of formula 10, a hydrazone (*Chem, Int.* bEd. Engl. 1968, 7, pp. 120-128). In the presence of boron tribromide, the hydrazone is converted into the compound of formula 3a (U.S. Pat. No. 5,358,968), a phenol derivative (*Tetrahedron Letters,* 40 (1999) pp. 4327-4330).

Alternatively, the compound of formula 3b may be prepared by reacting the aldehyde or ketone compound of formula 11 with a hydrazine derivative The following Examples are intended to further illustrate the present invention without limiting its scope.

Example 1

(E)-methyl 2-(2-((2,5-dimethyl-4-((E)-1-(propoxyimino)propyl)phenoxy)-methyl)phenyl)-3-methoxyacrylate (compound 1)

<Step 1>

To a solution of (E)-methyl 2-(2-(bromomethyl)phenyl)-3-methoxyacrylate (1.0 g, 3.5 mmol) and 4-hydroxy-2,5-dimethylbenzaldehyde (0.6 g, 4.2 mmol) in 20 mL of acetonitrile ($CH_3CN$) was added cesium carbonate (1.7 g, 5.2 mmol), and the reaction mixture was incubated at room temperature for 3 hours with stirring, followed by concentration in a vacuum to remove the reaction solvent. The concentrate was stirred in water (20 mL) and the aqueous layer was extracted twice with 20 mL of dichloromethane. The organic layers thus obtained were pooled, dried over anhydrous magnesium sulfate, filtrated and concentrated in a vacuum. The residue thus obtained was separated using silica gel chromatography to afford (E)-methyl 2-((2-((4-formyl-2,5-dimethylphenoxy)methyl)phenyl)-3-methoxyacrylate as a white solid (0.88 g, yield 71%).

m/s [M+1]=355.20

¹H NMR (300 MHz, CDCl₃): δ 7.64 (s, 1H), 7.63-7.59 (m, 1H), 7.40-7.30 (m, 2H), 7.22-7.18 (m, 2H), 6.54 (s, 1H), 4.96 (s, 2H), 4.81-4.76 (m, 1H), 3.85 (s, 3H), 3.72 (s, 3H), 2.28 (s, 3H), 2.27 (s, 3H), 1.82-1.68 (m, 2H), 0.99-0.94 (t, 3H)

<Step 2>

A solution of 0.2 g (0.56 mmol) of (E)-methyl 2-(2-((4-formyl-2,5-dimethylphenoxy)methyl)phenyl)-3-methoxy-acrylate obtained in Step 1 in 15 mL of tetrahydrofuran (THF) was refrigerated at −78° C. and reacted at that temperature for 2 hours with ethyl magnesium bromide (0.22 mL, 1.2 eq) while stirring. After completion of the reaction, the reaction mixture was adjusted to pH 7 at 0° C. with 1N-HCl and concentrated in a vacuum. The residue thus obtained was stirred in water (10 mL) and extracted twice with 10 mL of dichloromethane. The organic layer was dried over anhydrous magnesium sulfate, filtrated and concentrated in a vacuum to remove the solvent. The concentrate was purified by silica gel chromatography to yield (E)-methyl 2-(2-((4-(1-hydroxypropyl)-2,5-dimethylphenoxy)methyl)phenyl)-3-methoxyacrylate as a white oil (0.17 g, yield 79%).

m/s [M+1]=385.10

¹H NMR (300 MHz, CDCl₃): δ 7.64 (s, 1H), 7.63-7.59 (m, 1H), 7.40-7.30 (m, 2H), 7.22-7.17 (m, 2H), 6.54 (s, 1H), 4.96 (s, 2H), 4.81-4.76 (m, 1H), 3.85 (s, 3H), 3.72 (s, 3H), 2.28 (s, 3H), 2.27 (s, 3H), 1.82-1.68 (m, 2H), 0.99-0.94 (t, 3H)

<Step 3>

A solution of 0.15 g (0.39 mmol) of (E)-methyl 2-(2-((4-(1-hydroxypropyl)-2,5-dimethylphenoxy)methyl)phenyl)-3-methoxyacrylate obtained in Step 2 in 10 mL of dichloromethane was reacted with 0.29 g (0.78 mmol) of pyridinium dichromate at room temperature for 2 hours with stirring, followed by filtration through celite. The organic layer was dried over anhydrous magnesium sulfate, filtered and concentrated in a vacuum to afford (E)-methyl 2-(2-((2,5-dimethyl-4-propionylphenoxy)methyl)phenyl)-3-methoxyacrylate as a brown oil (0.11 g, yield: 71%).

m/s [M+1]=383.10

¹H NMR (300 MHz, CDCl₃): δ 7.64 (s, 1H), 7.56-7.54 (m, 2H), 7.40-7.31 (m, 2H), 7.22-7.19 (m, 1H), 6.59 (s, 1H), 5.03 (s, 2H), 3.86 (s, 3H), 3.72 (s, 3H), 2.95-2.88 (q, 2H), 2.49 (s, 3H), 2.28 (s, 3H), 1.21-1.16 (t, 3H)

<Step 4>

To a solution of 0.17 g (0.44 mmol) of (E)-methyl 2-(2-((2,5-dimethyl-4-propionylphenoxy)methyl)phenyl)-3-methoxyacrylate obtained in Step 3 and 0.06 g (0.88 mmol) of hydroxylamine chloride in 10 mL of methanol was added 0.8 g of a molecular sieve for dehydration. The reaction mixture was stirred at room temperature for 3 hours and filtered through celite and the filtrate was concentrated in a vacuum. The concentrate was stirred in water (10 mL) and extracted twice with 10 mL of dichloromethane. The organic layer was dried over anhydrous magnesium sulfate, followed by vacuum concentration. The residue was purified through silica gel chromatography to produce (E)-methyl 2-(2-((4-((E)-1-(hydroxyimino)propyl)-2,5-dimethylphenoxy)methyl)phenyl)-3-methoxyacrylate as a white solid (0.11 g, yield: 67%).

m/s [M+1]=398.10

¹H NMR (300 MHz, CDCl₃): δ 7.64 (s, 1H), 7.61-7.56 (m, 1H), 7.41-7.34 (m, 2H), 7.21-7.18 (m, 1H), 6.97 (s, 1H), 6.59 (s, 1H), 4.99 (s, 2H), 3.85 (s, 3H), 3.72 (s, 3H), 2.75-2.67 (q, 2H), 2.35 (s, 3H), 2.20 (s, 3H), 1.08-1.03 (t, 3H)

<Step 5>

To a solution of 0.12 g (0.3 mmol) of (E)-methyl 2-(2-((4-((E)-1-(hydroxyimino)propyl)-2,5-dimethylphenoxy)methyl)phenyl)-3-methoxyacrylate obtained in Step 4 and 0.2 g (0.61 mmol) of cesium carbonate in 10 mL of acetonitrile (CH₃CN) was added propyl bromide (0.05 mL, 0.55 mmol), followed by stirring at room temperature for 3 hours. After completion of the reaction, the solvent was removed under reduced pressure and the residue thus obtained was stirred in water (10 mL) and extracted twice with 10 mL of dichloromethane. The organic layer was dried over anhydrous magnesium sulfate and concentrated in a vacuum and the concentrate was purified by silica gel chromatography to afford 0.1 g of (E)-methyl 2-(2-((2,5-dimethyl-4-((E)-1-(propoxyimino)propyl)phenoxy)-methyl)phenyl)-3-methoxyacrylate as a white oil (yield: 77%).

m/s [M+1]=440.10

¹H NMR (300 MHz, CDCl₃): δ 7.63 (s, 1H), 7.59-7.57 (m, 1H), 7.38-7.31 (m, 2H), 7.20-7.18 (m, 1H), 6.96 (s, 1H), 6.58 (s, 1H), 4.96 (s, 2H), 4.11-4.06 (td, 2H), 3.85 (s, 3H), 3.72 (s, 3H), 2.69-2.61 (q, 4H), 2.26 (s, 3H), 2.24 (s, 3H), 1.76-1.62 (m, 2H), 1.08-0.90 (m, 6H)

Example 2

(E)-methyl 2-(2-((2,5-dimethyl-4-((E)-1-(propoxyimino)ethyl)phenoxy)-methyl)phenyl)-3-methoxyacrylate (compound 2)

<Step 1>

Methyl magnesium bromide (2.4 mL, 1.2 eq) was dropwise added at −78° C. to a solution of 2,5-dimethyl-4-methoxybenzaldehyde (1.0 g, 6.0 mmol) in 30 mL of tetrahydrofuran (THF) with stirring and the reaction mixture was allowed to react at that temperature while being stirred. After completion of the reaction, the reaction mixture was adjusted to pH 7 at 0° C. with 1N-HCl and concentrated in a vacuum. The residue thus obtained was stirred in water (20 mL) and extracted twice with 20 mL of dichloromethane. The organic layer was dried over anhydrous magnesium sulfate, filtrated and concentrated in a vacuum to remove the solvent. The concentrate was purified through silica gel chromatography to yield 1-(4-methoxy-2,5-dimethylphenyl)ethanol as a white oil (0.87 g, yield 74%).

m/s [M+1]=195.10

¹H NMR (300 MHz, CDCl₃): δ 7.54 (s, 1H), 6.61 (s, 1H), 4.57-4.51 (m, 1H), 3.88 (s, 3H), 2.58 (s, 3H), 2.56 (s, 3H), 1.74-1.60 (m, 2H), 1.00-0.95 (t, 3H)

<Step 2>

A solution of 0.8 g (4.1 mmol) of 1-(4-methoxy-2,5-dimethylphenyl)ethanol obtained in Step 1 in 30 mL of dichloromethane was reacted with 3.0 g (8.2 mmol) of pyridinium dichromate at room temperature for 2 hours with stirring, followed by filtration through celite. The organic layer was dried over anhydrous magnesium sulfate, filtered and concentrated in a vacuum to afford 1-(4-methoxy-2,5-dimethylphenyl)ethanone as a brown oil (0.54 g, yield: 69%).

m/s [M+1]=193.20

¹H NMR (300 MHz, CDCl₃): δ 7.33 (s, 1H), 6.54 (s, 1H), 3.85 (s, 3H), 2.57 (s, 3H), 2.55 (s, 3H), 2.91-2.86 (q, 2H), 1.18-1.13 (t, 3H)

<Step 3>

To a solution of 0.5 g (2.6 mmol) of 1-(4-methoxy-2,5-dimethylphenyl)ethanone obtained in Step 2 and 0.36 g (5.1 mmol) of hydroxylamine chloride in 15 mL of methanol was added 1.0 g of a molecular sieve for dehydration. The reaction mixture was stirred at room temperature for 3 hours and filtered through celite and the filtrate was concentrated in a vacuum. The concentrate was stirred in water (20 mL) and the aqueous layer was extracted twice with 20 mL of dichloromethane. The organic layer was dried over anhydrous magnesium sulfate, followed by vacuum concentration. The residue was purified through silica gel chromatography to produce (E)-1-(4-methoxy-2,5-dimethylphenyl)ethanone oxime as a white solid (0.45 g, yield: 83%).

m/s [M+1]=208.10

$^1$H NMR (300 MHz, CDCl$_3$): δ 7.35 (s, 1H), 6.53 (s, 1H), 3.86 (s, 3H), 2.56 (s, 3H), 2.54 (s, 3H), 2.71-2.64 (q, 2H), 1.11-1.06 (t, 3H)

<Step 4>

To a solution of 0.51 g (2.4 mmol) of (H)-1-(4-methoxy-2,5-dimethylphenyl)ethanone oxime, obtained in Step 3 and 1.2 g (3.6 mmol) of cesium carbonate in 15 mL of acetonitrile (CH$_3$CN) was added propyl bromide (0.22 g, 2.4 mmol), followed by stirring at room temperature for 3 hours. After completion of the reaction, the solvent was removed under reduced pressure and the residue thus obtained was stirred in water (20 mL) and extracted twice with 20 mL of dichloromethane. The organic layer was dried over anhydrous magnesium sulfate and concentrated in a vacuum and the concentrate was purified by silica gel chromatography to afford (E)-1-(4-methoxy-2,5-dimethylphenyl)ethanone-propyloxime as a while oil (0.53 g, yield: 88%).

m/s [M+1]=250.20

$^1$H NMR (300 MHz, CDCl$_3$): δ 7.33 (s, 1H), 6.54 (s, 1H), 4.11-4.06 (t, 2H), 3.85 (s, 3H), 2.64-2.60 (q, 2H), 2.52 (s, 3H), 2.50 (s, 3H), 1.66-1.62 (q, 2H), 1.08-0.99 (m 6H)

<Step 5>

To a solution of 0.5 g (2.0 mmol) of (E)-1-(4-methoxy-2,5-dimethylphenyl)ethanone-propyloxime obtained in Step 4 in 15 mL of dichloromethane was added boron tribromide (BBr$_3$) (0.28 mL, 2.9 mmol) and the reaction mixture was allowed to react at room temperature with stirring. After completion of the reaction, the residue was stirred in water (20 mL) and the aqueous layer was extracted twice with 20 mL of dichloromethane. The organic layer was dried over anhydrous magnesium sulfate and concentrated in a vacuum and the concentrate was purified by silica gel chromatography to afford 0.23 g of (E)-1-(4-hydroxy-2,5-dimethylphenyl)ethanone propyloxime as a white oil (yield: 49%).

m/s [M+1]=236.10

$^1$H NMR (300 MHz, CDCl$_3$): δ 7.57 (s, 1H), 6.64 (s, 1H), 4.12-4.09 (t, 2H), 2.71-2.68 (q, 2H), 2.57 (s, 3H), 2.55 (s, 3H), 1.73-1.67 (q, 2H), 1.18-1.13 (m 6H)

<Step 6>

To a solution of (E)-methyl 2-(2-(bromomethyl)phenyl)-3-methoxyacrylate (1.0 g, 3.5 mmol) and (E)-1-(4-hydroxy-2,5-dimethylphenyl)ethanone propyloxime (0.6 g, 4.2 mmol) obtained in Step 5 in 20 mL of acetonitrile (CH$_3$CN) was added cesium carbonate (1.7 g, 5.2 mmol), followed by stirring at room temperature for 3 hours. The reaction solvent was removed by concentration in a vacuum. The residue was stirred in water (20 mL) and the aqueous layer was extracted twice with 20 mL of dichloromethane. The organic layer was dried over anhydrous magnesium sulfate, filtered and concentrated in a vacuum to remove the solvent. The concentrate was purified through silica gel chromatography to afford (E)-methyl 2-(2-((2,5-dimethyl-4-((E)-1-(propoxyimino)ethyl)phenoxy)methyl)phenyl)-3-methoxyacrylate as a white oil (0.88 g, yield 71%).

m/s [M+1]=426.10

$^1$H NMR (300 MHz, CDCl$_3$): δ 7.62 (s, 1H), 7.58-7.56 (m, 1H), 7.38-7.32 (m, 2H), 7.20-7.18 (m, 1H), 7.01 (s, 1H), 6.57 (s, 1H), 4.97 (s, 2H), 4.13-4.08 (t, 2H), 3.85 (s, 3H), 3.72 (s, 3H), 2.28 (s, 3H), 2.24 (s, 3H), 1.79-1.70 (m, 2H), 1.00-0.95 (t, 3H)

Example 3

(E)-methyl 2-(2-((3-(benzyloxy)phenoxy)methyl)phenyl)-3-methoxyacrylate (compound 3)

<Step 1>

To a solution of (E)-methyl 2-(2-(bromomethyl)phenyl)-3-methoxyacrylate (0.5 g, 1.7 mmol) and 3-hydroxyphenol (0.2 g, 2.1 mmol) in 20 mL of acetonitrile (CH$_3$CN) was added potassium carbonate (0.35 g, 2.6 mmol). The reaction mixture was stirred under reflux and concentrated in a vacuum to remove the solvent. The residue was stirred in water (20 mL) and the aqueous layer was extracted twice with 20 mL of dichloromethane. The organic layer was dried over anhydrous magnesium sulfate and concentrated in a vacuum to remove the solvent. The concentrate was purified by silica gel chromatography to afford (E)-methyl 2-(2-((3-hydroxyphenoxy)methyl)phenyl)-3-methoxyacrylate as a white solid (0.4 g, yield 74%).

m/s [M+1]=315.10

$^1$H NMR (300 MHz, CDCl$_3$): δ 7.64 (s, 1H), 7.56-7.50 (m, 1H), 7.36-7.33 (m, 3H), 7.20-7.17 (m, 1H), 6.21-6.18 (m, 3H), 4.98 (s, 2H), 3.88 (s, 3H), 3.77 (s, 3H)

<Step 2>

A solution of (E)-methyl 2-(2-((3-hydroxyphenoxy)methyl)phenyl)-3-methoxyacrylate (0.2 g, 0.63 mmol) obtained in Step 1, benzyl bromide (0.1 mL, 0.84 mmol) and cesium carbonate (0.31 g, 0.95 mmol) in 20 mL of acetonitrile (CH$_3$CN) was stirred at room temperature for 3 hours after which the reaction solvent was removed by concentration in a vacuum. The residue was stirred in water (20 mL) and the aqueous layer was extracted twice with 20 mL of dichloromethane. The organic layer was dried over anhydrous magnesium sulfate, filtered and concentrated in a vacuum. The concentrate was purified by silica gel chromatography to afford (E)-methyl 2-(2-((3-(benzyloxy)phenoxy)methyl)phenyl)-3-methoxyacrylate as a white solid (0.18 g, yield 70%).

m/s [M+1]=405.10

$^1$H NMR (300 MHz, CDCl$_3$): δ 7.59 (s, 1H), 7.42-7.33 (m, 8H), 7.20-7.14 (m, 2H), 6.60-6.54 (m, 3H), 5.03 (s, 2H), 3.80 (s, 3H), 3.70 (s, 3H)

Example 4

(E)-methyl 2-(2-((3-((E)-(ethoxyimino)methyl)phenoxy)methyl)phenyl)-3-methoxyacrylate (compound 4)

<Step 1>

A solution of (E)-methyl 2-(2-(bromomethyl)phenyl)-3-methoxyacrylate (3.0 g, 10.52 mmol), 3-hydroxybenzaldehyde (1.41 g, 1.1 eq) and potassium carbonate (3.0 g, 3.0 eq) in a mixture of acetonitrile (CH$_3$CN, 30 mL)/H$_2$O (5 mL) was refluxed for 15 hours. After concentration in a vacuum to remove the reaction solvent, the residue was stirred in water (50 mL) and the aqueous layer was extracted twice with 50 mL of dichloromethane. The organic layer was dried over anhydrous magnesium sulfate, filtered and concentrated in a vacuum to remove the solvent. Purification by silica gel chromatography afforded (E)-methyl 2-(2((3-formylphenoxy)methyl)phenyl)-3-methoxyacrylate as a white solid (3.0 g, yield 87%).

m/s [M+1]=327.10

$^1$H NMR (300 MHz, CDCl$_3$): δ 9.60 (s, 1H), 8.05 (s, 1H), 7.54-7.51 (m, 2H), 7.42 (s, 1H), 7.33-7.29 (m, 2H), 7.24-7.21 (m, 1H), 7.18-7.16 (m, 1H), 6.73-6.72 (d, 1H), 4.99 (s, 2H)

<Step 2>

A solution of (E)-methyl 2-(2-((3-formylphenoxy)methyl)phenyl)-3-methoxyacrylate (0.10 g, 0.306 mmol) in Step 1 and ethylhydroxylamine hydrochloride (45 mg, 1.5 eq) in 7 mL of methanol was stirred at room temperature for 3 hours in the presence of a molecular sieve for dehydration and filtered through celite. After concentration of the filtrate in a vacuum, the residue was stirred in water (10 mL) and extracted twice with 15 mL of dichloromethane. The organic layer was dried over anhydrous magnesium sulfate and concentrated in a vacuum. Purification of the residue by silica gel chromatography afforded 80 mg of (E)-methyl 2-(2-((3-((E)-(ethoxyimino)methyl)phenoxy)methyl)phenyl)-3-methoxyacrylate as a white oil (yield: 71%).

m/s [M+1]=370.10

$^1$H NMR (300 MHz, CDCl$_3$): δ 8.12 (s, 1H), 7.60 (s, 1H), 7.56-7.53 (m, 2H), 7.44 (s, 1H), 7.36-7.32 (m, 2H), 7.26-7.23 (m, 1H), 7.20-7.18 (m, 1H), 6.76-6.75 (d, 1H), 5.01 (s, 2H), 4.12-4.08 (q, 2H), 3.84 (s, 3H), 3.72 (s, 3H), 1.30-1.27 (t, 3H)

Example 5

(E)-methyl 2-(2-((5-hydroxyphenoxy)methyl)phenyl)-3-methoxyacrylate (compound 5)

The same procedure as Step 1 of Example 3 was repeated to obtain the title compound as a white solid (0.4 g, yield 74%).

m/s [M+1]=315.10

$^1$H NMR (300 MHz, CDCl$_3$): δ 7.61 (s, 1H), 7.57-7.54 (m, 1H), 7.38-7.32 (m, 2H), 7.20-7.17 (m, 1H), 7.12-7.06 (t, 1H), 6.52-6.48 (ddd, 1H), 6.42-6.38 (m, 1H), 5.30 (s, 2H), 4.95 (s, 2H), 3.84 (s, 3H), 3.74 (s, 3H)

Example 6

(E)-methyl 2-(2-((5-formyl-2-methoxyphenoxy)methyl)phenyl)-3-methoxyacrylate (compound 6)

Potassium carbonate (0.35 g, 2.6 mmol) was added to a solution (E)-methyl 2-(2-(bromomethyl)phenyl)-3-methoxyacrylate (0.5 g, 1.7 mmol) and 3-hydroxy-4-methoxybenzaldehyde (0.32 g, 2.1 mmol) in 20 mL of acetonitrile (CH$_3$CN) which was then stirred for 6 hours under reflux. The reaction solvent was removed by vacuum concentration. The residue was stirred in water (20 mL), and the aqueous layer was extracted twice with 20 mL of dichloromethane. The organic was dried over anhydrous magnesium sulfate, filtered and concentrated in a vacuum to remove the solvent. Purification through silica gel chromatography afforded the title compound as a white oil (0.3 g, yield 49%).

m/s [M+1]=357.10

$^1$H NMR (300 MHz, CDCl$_3$): δ 9.79 (s, 1H), 7.65 (s, 1H), 7.59-7.56 (m, 1H), 7.48-7.44 (dd, 1H), 7.35-7.30 (m, 3H). 7.21-7.18 (m, 1H), 7.01-6.98 (d, 1H), 5.27 (s, 2H), 3.99 (s, 3H), 3.88 (s, 3H), 3.74 (s, 3H)

Example 7

(E)-methyl 2-(2-((3-((E)-1-(propoxyimino)propyl)phenoxy)methyl)-phenyl)-3-methoxyacrylate (compound 7)

The procedure of Example 1 was repeated with the exception that 3-hydroxy-benzaldehyde was used in Step 1 instead of 4-hydroxy-2,5-dimethylbenzaldehyde to obtain the title compound as white oil (0.06 g, yield 24%).

m/s [M+1]=412.10

$^1$H NMR (300 MHz, CDCl$_3$): δ 7.63 (s, 1H), 7.58-7.56 (m, 2H), 7.36-7.30 (m, 2H), 7.20-7.18 (m, 2H), 6.96-6.94 (dd, 2H), 4.95 (s, 2H), 4.11-4.06 (t, 2H), 3.85 (s, 3H), 3.72 (s, 3H), 2.69-2.61 (q, 3H), 1.76-1.62 (m, 2H), 1.08-0.90 (m, 6H)

Example 8

(E)-methyl 2-(2-((4-((E)-1-(propoxyimino)ethyl)phenoxy)methyl)phenyl)-3-methoxyacrylate (compound 8)

The procedure of Example 2 was repeated with the exception that 1-(4-hydroxyphenyl)ethanone was used in Step 1 instead of 2,5-dimethyl-4-methoxybenzaldehyde to obtain the title compound as a white solid (0.33 g, yield 71%).

m/s [M+1]=398.10

$^1$H NMR (300 MHz, CDCl$_3$): δ 7.60 (s, 1H), 7.57-7.52 (m, 3H), 7.35-7.32 (m, 2H), 7.20-7.17 (m, 1H), 6.90-6.87 (d, 2H), 4.99 (s, 2H), 4.15-4.11 (t, 2H), 3.84 (s, 3H), 3.72 (s, 3H), 2.21 (s, 3H), 1.78-1.71 (m, 3H), 1.01-0.96 (t, 3H)

Example 9

(E)-methyl 2-(2-((4-((E)-1-(2-(piperidin-1-yl)ethoxyimino)ethyl)phenoxy)-methyl)phenyl)-3-methoxyacrylate (compound 9)

The same procedure as Step 1 of Example 4 was repeated with the exception that 1-(4-hydroxyphenyl)ethanone was used instead of 3-hydroxybenzaldehyde, followed by conducting the same procedures as Steps 2 and 3 of Example 2. Subsequently, the same procedure as Step 4 of Example 2 except reaction with 1-(2-chloroethyl)piperidine instead of propyl bromide was repeated to afford the title compound as a white solid (0.2 g, yield 68%).

m/s [M+1]=467.10

$^1$H NMR (300 MHz, CDCl$_3$): δ 7.61 (s, 1H), 7.58-7.53 (m, 3H), 7.36-7.33 (m, 2H), 7.21-7.18 (m, 1H), 6.92-6.89 (dd, 2H), 4.98 (s, 2H), 3.85 (s, 3H), 3.74 (s, 3H), 3.68-3.65 (t, 2H), 2.48-2.46 (m, 4H), 2.25-2.23 (t, 2H), 2.20 (s, 3H), 1.74-1.70 (m, 4H), 1.58-1.54 (m, 2H)

Example 10

(E)-methyl 3-methoxy-2-(2-((3-((E)-(2-(piperidin-1-yl)ethoxyimino)methyl)phenoxy)methyl)phenyl)acrylate (compound 10)

<Step 1>

(E)-methyl 2-(2-(bromomethyl)phenyl)-3-methoxyacrylate (3.0 g, 10.52 mmol), 3-hydroxybenzaldehyde (1.41 g, 1.1 eq) and potassium carbonate (3.0 g, 3.0 eq) were together refluxed for 15 hours in acetonitrile (CH$_3$CN, 30 mL)/H$_2$O (5 mL). Concentration at a reduced pressure removed the reaction solvent. The residue was stirred in water (50 mL) and the aqueous layer was extracted twice with 50 mL of dichloromethane. The organic layer was dried over anhydrous magnesium sulfate, filtered and concentrated in a vacuum to remove the solvent. The concentrate was purified by silica gel chromatography to give (E)-methyl 2-(2((3-formylphenoxy)methyl)phenyl)-3-methoxyacrylate as a white solid (3.0 g, yield 87%).

m/s [M+1]=327.10

$^1$H NMR (300 MHz, CDCl$_3$): δ 9.60 (s, 1H), 7.64 (s, 1H), 7.58-7.55 (m, 1H), 7.47-7.43 (dd, 1H), 7.34-7.29 (m, 3H). 7.20-7.18 (m, 1H), 7.00-6.98 (d, 1H), 5.26 (s, 2H), 3.87 (s, 3H), 3.74 (s, 3H)

<Step 2>

(E)-methyl 2-(2((3-formylphenoxy)methyl)phenyl)-3-methoxyacrylate obtained in Step 1 (0.10 g, 0.306 mmol) and hydroxylamine hydrochloride (32 mg, 1.5 eq) were together stirred at room temperature for 3 hours in 7 mL of methanol in the presence of 0.5 g of a molecular sieve for dehydration. After filtration through celite, the filtrate was concentrated in a vacuum. The residue was stirred in water (10 mL) and extracted twice with 15 mL of dichloromethane. The organic layer was dried over anhydrous magnesium sulfate and concentrated in a vacuum. Purification by silica gel chromatography afforded (E)-methyl 2-(2-((3-((E)-(hydroxyamino)methyl)phenoxy)methyl)phenyl)-3-methoxyacrylate as a white oil (0.07 g, yield: 63%).

m/s [M+1]=342.10

$^1$H NMR (300 MHz, CDCl$_3$): δ 8.33 (s, 1H), 7.61 (s, 1H), 7.56-7.53 (m, 1H), 7.45-7.41 (dd, 1H), 7.30-7.28 (m, 3H). 7.21-7.17 (m, 1H), 7.01-6.99 (d, 1H), 5.25 (s, 2H), 3.88 (s, 3H), 3.73 (s, 3H)

<Step 3>

(E)-methyl 2-(2-((3-((E)-(hydroxyamino)methyl)phenoxy)methyl)phenyl)-3-methoxyacrylate obtained in Step 2 (0.22 g, 0.63 mmol) was stirred, together 1-(2-chloroethyl)piperidine (0.13 g, 1.5 eq) and cesium carbonate (0.31 g, 0.95 mmol), at room temperature for 3 hours in 20 mL of acetonitrile (CH$_3$CN), followed by concentration at a reduced pressure to remove the reaction solvent. The residue was stirred in water (20 mL) and the aqueous layer was extracted twice with 20 mL of dichloromethane. The organic layer was dried over anhydrous magnesium sulfate, filtered and concentrated in a vacuum. Purification by silica gel chromatography afforded (E)-methyl 3-methoxy-2-(2-((3-((E)-(2-(piperidin-1-yl)ethoxyimino)methyl)phenoxy)methyl)phenyl)acrylate as a white oil (0.26 g, yield 61%).

m/s [M+1]=453.10

$^1$H NMR (300 MHz, CDCl$_3$): δ 8.33 (s, 1H), 7.60 (s, 1H), 7.58-7.54 (m, 3H), 7.35-7.33 (m, 2H), 7.20-7.18 (m, 1H), 6.91-6.89 (dd, 2H), 4.99 (s, 2H), 3.83 (s, 3H), 3.72 (s, 3H), 3.67-3.65 (t, 2H), 2.46-2.44 (m, 4H), 2.24-2.22 (t, 2H), 1.73-1.70 (m, 4H), 1.56-1.53 (m, 2H)

Example 11

(E)-methyl 2-(2-((3-(2-(2-hydroxyethylamino)ethoxy)phenoxy)methyl)-phenyl)-3-methoxyacrylate (compound 11)

The procedure of Example 3 was repeated with the exception that 2-(2-hydroxyethyl)aminoethyl bromide was used in Step 2 instead of benzyl bromide to obtain the title compound as a white oil (0.39 g, yield 49%).

m/s [M+1]=402.10

$^1$H NMR (300 MHz, CDCl$_3$): δ 8.06 (s, 1H), 7.62 (s, 1H), 7.58-7.55 (m, 1H), 7.38-7.35 (m, 2H), 7.24-7.18 (m, 2H), 6.54-6.50 (m, 3H), 5.02 (s, 2H), 4.10-4.07 (t, 2H), 3.94-3.91 (t, 2H), 3.89 (s, 3H), 3.78 (s, 3H), 2.96-2.93 (t, 2H), 2.74-2.71 (t, 2H)

Example 12

(E)-methyl 2-(2-((3-(2-hydroxyethoxy)phenoxy)methyl)phenyl)-3-methoxyacrylate (compound 12)

The procedure of Example 3 was repeated with the exception that 2-bromoethanol was used in Step 2 instead of benzyl bromide to obtain the title compound as a white oil (1.3 g, yield 87%).

m/s [M+1]=359.10

$^1$H NMR (300 MHz, CDCl$_3$): δ 8.03 (s, 1H), 7.61 (s, 1H), 7.57-7.54 (m, 1H), 7.39-7.30 (m, 2H), 7.20-7.13 (m, 2H), 6.56-6.50 (m, 3H), 4.92 (s, 2H), 4.07-4.04 (t, 2H), 3.52-3.50 (t, 2H), 3.84 (s, 3H), 3.72 (s, 3H)

Example 13

(E)-4-(2-(3-(2-(1,3-dimethoxy-3-oxoprop-1-en-2-yl)benzyloxy)phenoxy)-ethyl)morpholine 4-oxide (compound 13)

The procedure of Example 3 was repeated with the exception that 4-(2-chloroethyl)morpholine 4-oxide was used in Step 2 instead of benzyl bromide to obtain the title compound as a white solid (0.6 g, yield 57%).

m/s [M+1]=444.10

$^1$H NMR (300 MHz, CDCl$_3$): δ 7.62 (s, 1H), 7.55-7.51 (m, 1H), 7.35-7.30 (m, 2H), 7.20-7.13 (m, 2H), 6.56-6.47 (m, 3H), 4.95 (s, 2H), 4.66-4.63 (t, 2H), 4.51-4.43 (t, 2H), 3.88 (s, 3H), 3.71 (s, 3H), 3.59-3.56 (t, 2H), 3.47-3.38 (t, 2H)

Example 14

(E)-methyl 3-methoxy-2-(2-((3-((E)-(propoxyimino)methyl)phenoxy)-methyl)phenyl)acrylate (compound 14)

The procedure of Example 10 was repeated with the exception that propyl bromide was used in Step 3 instead of 1-(2-chloroethyl)piperidine to obtain the title compound as a white oil (0.5 g, yield 71%).

m/s [M+1]=384.10

$^1$H NMR (300 MHz, CDCl$_3$): δ 8.35 (s, 1H), 7.61 (s, 1H), 7.56-7.51 (m, 3H), 7.36-7.30 (m, 2H), 7.21-7.19 (m, 2H), 6.89-6.87 (d, 1H), 4.98 (s, 2H), 4.12-4.09 (t, 2H), 3.85 (s, 3H), 3.73 (s, 3H), 1.70-1.66 (m, 2H), 1.00-0.97 (t, 3H)

Example 15

(E)-methyl 2-(2-((3-fluoro-5-hydroxyphenoxy)methyl)phenyl)-3-methoxyacrylate (compound 15)

The same procedure as Step 1 of Example 3 was repeated with the exception that 3-fluoro-5-hydroxyphenol was used instead of 3-hydroxyphenol to obtain the title compound as a brown solid (0.7 g, yield 77%).

m/s [M+1]=333.10

$^1$H NMR (300 MHz, CDCl$_3$): δ 7.64 (s, 1H), 7.52-7.50 (m, 1H), 7.35-7.32 (m, 2H), 7.19-7.16 (m, 1H), 6.22-6.15 (m, 3H), 4.93 (s, 2H), 3.85 (s, 3H), 3.74 (s, 3H)

Example 16

(E)-methyl 2-(2-((3-phenethoxyphenoxy)methyl)phenyl)-3-methoxyacrylate (compound 16)

The procedure of Example 3 was repeated with the exception that phenylethyl bromide was used in Step 2 instead of benzyl bromide to obtain the title compound as a white oil (0.3 g, yield 59%).

m/s [M+1]=419.10

$^1$H NMR (300 MHz, CDCl$_3$): δ 7.60 (s, 1H), 7.59-7.54 (m, 1H), 7.36-7.29 (m, 5H), 7.23-7.12 (m, 4H), 6.53-6.49 (m, 3H), 4.95 (s, 2H), 4.18-4.14 (t, 2H), 3.81 (s, 3H), 3.70 (s, 3H), 3.11-3.07 (t, 2H)

Example 17

(E)-methyl 2-(2-((4-((E)-1-(benzyloxyimino)ethyl) phenoxy)methyl)-phenyl)-3-methoxyacrylate (compound 17)

The same procedure as Step 1 of Example 4 with the exception that 1-(4-hydroxyphenyl)ethanone was used instead of 3-hydroxybenzaldehyde. Subsequently, the same procedure as Step 3 of Example 2 was conducted, followed by reaction with benzyl bromide to obtain the title compound as a white solid (0.4 g, yield 69%).

m/s [M+1]=446.10

$^1$H NMR (300 MHz, CDCl$_3$): δ 7.60 (s, 1H), 7.58-7.55 (m, 3H), 7.44-7.33 (m, 8H), 6.90-6.87 (d, 2H), 5.23 (s, 2H), 4.99 (s, 2H), 3.83 (s, 3H), 3.72 (s, 3H), 2.57 (s, 3H)

Example 18

(E)-methyl 2-(2-((4-((E)-1-(phenethoxyimino)ethyl) phenoxy)methyl)-phenyl)-3-methoxyacrylate (compound 18)

The same procedure as Step 1 of Example 4 with the exception that 1-(4-hydroxyphenyl)ethanone was used instead of 3-hydroxybenzaldehyde. Subsequently, the same procedure as Step 3 of Example 2, followed by reaction with phenylethyl bromide to obtain the title compound as a white oil (0.3 g, yield 57%).

m/s [M+1]=460.10

$^1$H NMR (300 MHz, CDCl$_3$): δ 7.60 (s, 1H), 7.57-7.52 (m, 3H), 7.36-7.29 (m, 4H), 7.25-7.18 (m, 4H), 6.92-6.89 (d, 2H), 5.00 (s, 2H), 4.41-4.36 (t, 2H), 3.84 (s, 3H), 3.72 (s, 3H), 3.08-3.03 (t, 2H)

Example 19

(E)-methyl 2-(2-((4-fluorophenoxy)methyl)phenyl)-3-methoxyacrylate (compound 19)

The same procedure as Step 1 of Example 3 was repeated with the exception that 4-fluorophenol was used instead of 3-hydroxyphenol to obtain the title compound as a yellow solid (0.6 g, yield 61%).

m/s [M+1]=317.10

$^1$H NMR (300 MHz, CDCl$_3$): δ 7.62 (s, 1H), 7.59-7.53 (m, 1H), 7.37-7.34 (m, 2H), 7.22-7.19 (m, 2H), 6.73-6.61 (m, 3H), 5.00 (s, 2H), 4.98 (t, 2H), 3.85 (s, 3H), 3.73 (s, 3H),

Example 20

(E)-methyl 2-(2-((3-hydroxy-5-(2-phenoxyethoxy) phenoxy)methyl)-phenyl)-3-methoxyacrylate (compound 20)

The procedure of Example 3 was repeated with the exception that benzene-1,2,5-triol was used in Step 1 instead of 3-hydroxyphenol and phenoxyethyl bromide was used in Step 2 instead of benzyl bromide to obtain the title compound as a white oil (0.4 g, yield 81%).

m/s [M+1]=465.10

$^1$H NMR (300 MHz, CDCl$_3$): δ 7.60 (s, 1H), 7.57-7.54 (m, 1H), 7.35-7.31 (m, 4H), 7.20-7.17 (m, 1H), 7.01-6.93 (m, 3H), 6.55 (s, 2H), 6.46-6.45 (t, 1H), 5.02 (s, 2H), 4.97 (s, 2H), 4.62-4.60 (d, 2H), 4.30 (s, 4H), 3.84 (s, 3H), 3.72 (s, 3H)

Example 21

(E)-methyl 2-(2-((3-(benzyloxy)-5-fluorophenoxy) methyl)phenyl)-3-methoxyacrylate (compound 21)

The procedure of Example 3 was repeated with the exception that 5-fluorobenzene-1,3-diol was used in Step 1 instead of 3-hydroxyphenol to obtain the title compound as a brown solid (0.2 g, yield 49%).

m/s [M+1]=423.10

$^1$H NMR (300 MHz, CDCl$_3$): δ 7.61 (s, 1H), 7.44-7.35 (m, 8H), 7.22-7.17 (m, 2H), 6.62-6.57 (m, 2H), 5.01 (s, 2H), 4.96 (s, 2H), 3.85 (s, 3H), 3.74 (s, 3H)

Example 22

(E)-methyl 2-(2-((3-fluoro-5-(2-phenoxyethoxy) phenoxy)methyl)phenyl)-3-methoxyacrylate (compound 22)

The procedure of Example 3 was repeated with the exception that 5-fluorobenzene-1,3-diol was used in Step 1 instead of 3-hydroxyphenol and phenoxyethyl bromide was used in Step 2 instead of benzyl bromide to obtain the title compound as a orange oil (0.1 g, yield 44%).

m/s [M+1]=453.10

$^1$H NMR (300 MHz, CDCl$_3$): δ 7.61 (s, 1H), 7.36-7.31 (m, 5H), 7.01-6.93 (m, 4H), 6.33-6.18 (m, 3H), 4.94 (t, 2H), 4.31-4.26 (m, 4H), 3.84 (s, 3H), 3.71 (s, 3H)

Example 23

(E)-methyl 2-(2-((3-fluoro-5-(pyridin-2-ylmethoxy) phenoxy)methyl)-phenyl)-3-methoxyacrylate (compound 23)

The procedure of Example 3 was repeated with the exception that 5-fluorobenzene-1,3-diol was used in Step 1 instead of 3-hydroxyphenol and 2-(bromomethyl)pyridine was used in Step 2 instead of benzyl bromide to obtain the title compound as a orange oil (0.05 g, yield 31%).

m/s [M+1]=424.10

$^1$H NMR (300 MHz, CDCl$_3$): δ 8.60-8.59 (d, 1H), 7.75-7.70 (td, 1H), 7.61 (s, 1H), 7.53-7.47 (m, 2H), 7.36-7.32 (m, 2H), 7.25-7.17 (m, 1H), 6.39-6.19 (s, 2H), 5.15 (s, 2H), 4.93 (s, 2H), 3.83 (s, 3H), 3.71 (s, 3H)

Example 24

(E)-methyl 2-(2-((3-fluoro-5-(4-nitrobenzyloxy)phenoxy)methyl)phenyl)-3-methoxyacrylate (compound 24)

The procedure of Example 3 was repeated with the exception that 5-fluorobenzene-1,3-diol was used in Step 1 instead of 3-hydroxyphenol and 4-nitrobenzyl bromide was used in Step 2 instead of benzyl bromide to obtain the title compound as a white solid (1.7 g, yield 89%).

m/s [M+1]=468.10

$^1$H NMR (300 MHz, CDCl$_3$): δ 7.63 (s, 1H), 7.42-7.31 (m, 5H), 7.20-7.16 (m, 2H), 6.58-6.52 (dd, 4H), 5.02 (s, 2H), 4.98 (s, 2H), 3.84 (s, 3H), 3.73 (s, 3H)

Example 25

(E)-methyl 3-methoxy-2-(2-((3-((E)-(morpholinoimino)methyl)phenoxy)-methyl)phenyl)acrylate (compound 25)

The procedure of Example 4 was repeated with the exception that N-aminomorpholine was used in Step 2 instead of (ethylhydroxy)amine hydrochloride to obtain the title compound as a white oil (0.2 g, yield 94%).

m/s [M+1]=411.10

$^1$H NMR (300 MHz, CDCl$_3$): δ 7.63-7.59 (d, 1H), 7.56 (s, 1H), 7.37-7.34 (m, 2H), 7.24-7.18 (m, 4H), 6.86-6.82 (m, 1H), 4.99 (s, 2H), 6.92-3.89 (m, 4H), 3.83 (s, 3H), 3.72 (s, 3H), 3.21-3.18 (m, 4H)

Example 26

(E)-methyl 2-(2-((3-(pyridin-2-ylmethoxy)phenoxy)methyl)phenyl)-3-methoxyacrylate (compound 26)

The procedure of Example 3 was repeated with the exception that 2-(bromomethyl)pyridine was used in Step 2 instead of benzyl bromide to obtain the title compound as a orange oil (0.1 g, yield 32%).

m/s [M+1]=406.10

$^1$H NMR (300 MHz, CDCl$_3$): δ 8.61-8.59 (dd, 1H), 7.75-7.69 (td, 1H), 7.61 (s, 1H), 7.59-7.50 (m, 2H), 7.36-7.30 (m, 2H), 7.24-7.13 (m, 3H), 6.60-6.53 (td, 3H), 5.18 (s, 2H), 4.94 (s, 2H), 3.82 (s, 3H), 3.70 (s, 3H)

Example 27

(E)-methyl 2-(2-((3-(pyridin-4-ylmethoxy)phenoxy)methyl)phenyl)-3-methoxyacrylate (compound 27)

The procedure of Example 3 was repeated with the exception that 4-(bromomethyl)pyridine was used in Step 2 instead of benzyl bromide to obtain the title compound as a orange oil (0.04 g, yield 29%).

m/s [M+1]=406.10

$^1$H NMR (300 MHz, CDCl$_3$): δ 8.62-8.60 (dd, 1H), 7.60 (s, 1H), 7.55-7.52 (m, 1H), 7.35-7.32 (m, 4H), 7.20-7.14 (m, 2H), 6.58-6.54 (m, 3H), 5.06 (s, 2H), 4.96 (s, 2H), 3.82 (s, 3H), 3.70 (s, 3H)

Example 28

(E)-methyl 2-(2-((3-hydroxy-5-(pyridin-2-ylmethoxy)phenoxy)methyl)-phenyl)-3-methoxyacrylate (compound 28)

The procedure of Example 3 was repeated with the exception that benzene-1,3,5-triol was used in Step 1 instead of 3-hydroxyphenol and 2-(bromomethyl)pyridine was used in Step 2 instead of benzyl bromide to obtain the title compound as a yellow oil (0.05 g, yield 26%).

m/s [M+1]=422.10

$^1$H NMR (300 MHz, CDCl$_3$): δ 8.60-8.58 (dd, 1H), 7.74-7.67 (td, 1H), 7.60 (s, 1H), 7.59-7.57 (m, 1H), 7.38-7.35 (m, 2H), 7.21-7.13 (m, 3H), 6.58-6.53 (td, 3H), 5.17 (s, 2H), 4.99 (s, 2H), 3.85 (s, 3H), 3.74 (s, 3H)

Example 29

(E)-methyl 2-(2-((3-hydroxy-5-(pyridin-4-ylmethoxy)phenoxy)methyl)-phenyl)-3-methoxyacrylate (compound 29)

The procedure of Example 3 was repeated with the exception that benzene-1,3,5-triol was used in Step 1 instead of 3-hydroxyphenol and 4-(bromomethyl)pyridine was used in Step 2 instead of benzyl bromide to obtain the title compound as a yellow oil (0.03 g, yield 17%).

m/s [M+1]=422.10

$^1$H NMR (300 MHz, CDCl$_3$): δ 8.61-8.59 (dd, 1H), 7.62 (s, 1H), 7.577.53 (m, 1H), 7.36-7.33 (m, 4H), 7.22-7.17 (m, 2H), 6.90-6.84 (m, 3H), 5.12 (s, 2H), 4.99 (s, 2H), 3.85 (s, 3H), 3.74 (s, 3H)

Example 30

(E)-methyl 2-(2-((2,5-dimethyl-4-((E)-1-(morpholinoimino)propyl)-phenoxy)methyl)phenyl)-3-methoxyacrylate (compound 30)

<Step 1>

(E)-methyl 2-(2-(bromomethyl)phenyl)-3-methoxyacrylate (1.0 g, 3.5 mmol) was reacted with 4-hydroxy-2,5-dimethylbenzaldehyde (0.6 g, 4.2 mmol) at room temperature for 3 hours in 20 mL of acetonitrile (CH$_3$CN) in the presence of cesium carbonate (1.7 g, 5.2 mmol) with stirring. After concentration in a vacuum to remove the reaction solvent, the residue was stirred in water (20 mL) and the aqueous layer was extracted twice with 20 mL of dichloromethane. The organic layer was dried over anhydrous magnesium sulfate, filtered and concentrated in a vacuum. The residue was purified by silica gel chromatography to afford (E)-methyl 2-(2-((4-formyl-2,5-dimethylphenoxy)methyl)phenyl)-3-methoxyacrylate as a white solid (0.88 g, yield 71%).

m/s [M+1]=355.20

$^1$H NMR (300 MHz, CDCl$_3$): δ 7.64 (s, 1H), 7.63-7.59 (m, 1H), 7.40-7.30 (m, 2H), 7.22-7.18 (m, 2H), 6.54 (s, 1H), 4.96 (s, 2H), 4.81-4.76 (m, 1H), 3.85 (s, 3H), 3.72 (s, 3H), 2.28 (s, 3H), 2.27 (s, 3H), 1.82-1.68 (m, 2H), 0.99-0.94 (t, 3H)

<Step 2>

A solution of 0.2 g (0.56 mmol) of (E)-methyl 2-(2-((4-formyl-2,5-dimethylphenoxy)methyl)phenyl)-3-methoxyacrylate obtained in Step 1 in 15 mL of tetrahydrofuran (THF) was cooled to −78° C. and reacted with ethyl magnesium bromide (0.22 mL, 1.2 eq) at −78° C. for 2 hours. After completion of the reaction, the reaction mixture was adjusted to pH 7 with 1N-HCl at 0° C. and concentrated in a vacuum. The residue was stirred in water (10 mL) and extracted twice with 10 mL of dichloromethane. The organic layer was dried over anhydrous magnesium sulfate, filtered and concentrated in a vacuum. The concentrate was purified using silica gel chromatography to afford (E)-methyl 2-(2-((4-(1-hydroxypropyl)-2,5-dimethylphenoxy)methyl)phenyl)-3-methoxyacrylate as a white oil (0.17 g, yield 79%).

m/s [M+1]=385.10

$^1$H NMR (300 MHz, CDCl$_3$): δ 7.64 (s, 1H), 7.63-7.59 (m, 1H), 7.40-7.30 (m, 2H), 7.22-7.17 (m, 2H), 6.54 (s, 1H), 4.96 (s, 2H), 4.81-4.76 (m, 1H), 3.85 (s, 3H), 3.72 (s, 3H), 2.28 (s, 3H), 2.27 (s, 3H), 1.82-1.68 (m, 2H), 0.99-0.94 (t, 3H)

<Step 3>

In 10 mL of dichloromethane, 0.15 g (0.39 mmol) of (E)-methyl 2-(2-((4-(1-hydroxypropyl)-2,5-dimethylphenoxy)methyl)phenyl)-3-methoxyacrylate obtained in Step 2 was reacted with 0.29 g (0.78 mmol) of pyridinium dichromate at room temperature for 2 hours with stirring, followed by filtration through celite. The organic layer was dried over anhydrous magnesium sulfate and filtered after which the solvent was removed by concentration in a vacuum. (E)-methyl 2-(2-((2,5-dimethyl-4-propionylphenoxy)methyl)phenyl)-3-methoxyacrylate was obtained as a brown oil (0.11 g, yield: 71%).

m/s [M+1]=383.10

$^1$H NMR (300 MHz, CDCl$_3$): δ 7.64 (s, 1H), 7.56-7.54 (m, 2H), 7.40-7.31 (m, 2H), 7.22-7.19 (m, 1H), 6.59 (s, 1H), 5.03 (s, 2H), 3.86 (s, 3H), 3.72 (s, 3H), 2.95-2.88 (q, 2H), 2.49 (s, 3H), 2.28 (s, 3H), 1.21-1.16 (t, 3H)

<Step 4>

In 10 mL of methanol, 0.17 g (0.44 mmol) of (E)-methyl 2-(2-((2,5-dimethyl-4-propionylphenoxy)methyl)phenyl)-3-methoxyacrylate obtained in Step 3 was reacted with 0.09 g (0.88 mmol) of morpholinyl-4-amine in the presence of 0.8 g of a molecular sieve for dehydration at room temperature for 3 hours with stirring and the reaction mixture was filtered through celite. After the concentration of the filtrate in a vacuum, the residue was stirred in water (10 mL) and extracted twice with 10 mL of dichloromethane. The organic layer was dried over anhydrous magnesium sulfate and concentrated in a vacuum. Purification of the concentration by silica gel chromatography afforded (E)-methyl 2-(2-((2,5-dimethyl-4-((E)-1-(morpholinoimino)propyl)phenoxy)methyl)phenyl)-3-methoxyacrylate as a white oil (0.1 g, yield 50%)

m/s [M+1]=467.10

$^1$H NMR (300 MHz, CDCl$_3$): δ 7.61 (s, 1H), 7.56 (s, 1H), 7.38-7.40 (m, 2H), 7.43-7.28 (m, 2H), 6.65-6.63 (m, 1H), 4.99 (s, 2H), 4.12-4.09 (m, 4H), 4.07-4.03 (q, 2H), 3.84 (s, 3H), 3.74 (s, 3H), 3.34-3.30 (m, 4H), 1.68-1.64 (t, 3H)

Example 31

(E)-methyl 2-(2-((4-((E)-(hydroxyimino)methyl)-2-methylphenoxy)-methyl)phenyl)-3-methoxyacrylate (compound 31)

The procedure of Example 4 was repeated with the exception that 4-hydroxy-3-methylbenzaldehyde was used in Step 1 instead of 3-hydroxybenzaldehyde and hydroxyamine hydrochloride was used in Step 2 instead of (ethylhydroxy)amine hydrochloride to obtain the title compound as a white solid (0.6 g, yield 84%).

m/s [M+1]=356.10

$^1$H NMR (300 MHz, CDCl$_3$): δ 8.04 (s, 1H), 7.60 (s, 1H), 7.56-7.53 (m, 2H), 7.41-7.40 (m, 1H), 7.35-7.31 (m, 2H), 7.28-7.24 (m, 2H), 7.19-7.16 (m, 1H), 6.76-6.73 (d, 1H), 5.00 (s, 2H), 3.82 (s, 3H), 3.70 (s, 3H), 2.27 (s, 3H)

Example 32

(E)-methyl 2-(2-((2-methyl-4-((E)-(propoxyimino) methyl)phenoxy)-methyl)phenyl)-3-methoxyacrylate (compound 32)

The procedure of Example 10 was repeated with the exception that 4-hydroxy-3-methylbenzaldehyde was used in Step 1 instead of 3-hydroxybenzaldehyde and propyl bromide was used in Step 3 instead of 1-(2-chloroethyl)piperidine to obtain the title compound as a white solid (0.2 g, yield 88%).

m/s [M+1]=398.10

$^1$H NMR (300 MHz, CDCl$_3$): δ 8.60-8.59 (dd, 1H), 7.61 (s, 1H), 7.57-7.54 (m, 1H), 7.46-7.45 (d, 1H), 7.37-7.33 (m, 2H), 7.25-7.17 (m, 4H), 6.76-6.73 (d, 1H), 5.01 (s, 2H), 4.13-4.08 (t, 2H), 3.84 (s, 3H), 3.72 (s, 3H), 2.29 (s, 3H), 1.17-1.70 (m, 2H), 1.01-0.96 (t, 3H)

Example 33

(E)-methyl 2-(2-((4-((E)-(benzyloxyimino)methyl)-2-methylphenoxy)-methyl)phenyl)-3-methoxyacrylate (compound 33)

The procedure of Example 10 was repeated with the exception that 4-hydroxy-3-methylbenzaldehyde was used in Step 1 instead of 3-hydroxybenzaldehyde and benzyl bromide was used in Step 3 instead of 1-(2-chloroethyl)piperidine to obtain the title compound as a white solid (0.1 g, yield 64%).

m/s [M+1]=446.10

$^1$H NMR (300 MHz, CDCl$_3$): δ 8.10 (s, 1H), 7.61 (s, 1H), 7.57-7.54 (m, 1H), 7.45-7.18 (m, 9H), 7.21-7.18 (m, 1H), 6.76-6.74 (d, 1H), 5.20 (s, 2H), 5.02 (s, 2H), 3.84 (s, 3H), 3.72 (s, 3H), 2.29 (s, 3H)

Example 34

(E)-methyl 2-(2-((4-((E)-1-(hydroxyimino)ethyl)-2-methoxyphenoxy)-methyl)phenyl)-3-methoxyacrylate (compound 34)

The procedure of Example 2 was repeated with the exception that 4-hydroxy-3-methoxybenzaldehyde was used in Step 1 instead of 2,5-dimethyl-4-methoxybenzaldehyde and Step 4 was not conducted to obtain the title compound as a white solid (0.6 g, yield 74%).

m/s [M+1]=386.10

$^1$H NMR (300 MHz, CDCl$_3$): δ 7.61 (s, 1H), 7.54-7.51 (m, 1H), 7.31-7.28 (m, 2H), 7.25 (s, 1H), 7.17-7.14 (m, 1H), 7.01-6.98 (dd, 1H), 6.72-6.70 (d, 1H), 5.09 (s, 2H), 3.92 (s, 3H), 3.84 (s, 3H), 3.71 (s, 3H), 2.22 (s, 3H)

Example 35

(E)-methyl 2-(2-((4-((E)-1-(propoxyimino)ethyl)-2-methoxyphenoxy)-methyl)phenyl)-3-methoxyacrylate (compound 35)

The procedure of Example 2 was repeated with the exception that 3-hydroxy-4-methoxybenzaldehyde was used in Step 1 instead of 2,5-dimethyl-4-methoxybenzaldehyde to obtain the title compound as a white solid (0.3 g, yield 94%).

m/s [M+1]=428.10

$^1$H NMR (300 MHz, CDCl$_3$): δ 7.62 (s, 1H), 7.55-7.52 (m, 1H), 7.32-7.30 (m, 3H), 7.18-7.15 (m, 1H), 7.03-6.99 (dd, 1H), 6.73-6.70 (dd, 1H), 5.10 (s, 2H), 4.16-4.12 (t, 2H), 3.95 (s, 2H), 3.85 (s, 3H), 3.73 (s, 3H), 1.80-1.68 (m, 2H), 1.01-0.96 (t, 3H)

Example 36

(E)-methyl 2-(2-((4-((E)-1-(benzyloxyimino)ethyl)-2-methoxyphenoxy)-methyl)phenyl)-3-methoxyacrylate (compound 36)

The procedure of Example 2 was repeated with the exception that 4-hydroxy-3-methoxybenzaldehyde was used in Step 1 instead of 2,5-dimethyl-4-methoxybenzaldehyde and benzyl bromide was used in Step 4 instead of propyl bromide to obtain the title compound as a white solid (0.1 g, yield 73%).

m/s [M+1]=476.10
$^1$H NMR (300 MHz, CDCl$_3$): δ 7.62 (s, 1H), 7.55-7.52 (m, 1H), 7.45-7.43 (m, 8H), 7.19-7.16 (m, 1H), 7.03-7.00 (dd, 1H), 6.73-6.70 (d, 1H), 5.24 (s, 2H), 5.01 (s, 2H), 3.94 (s, 3H), 3.85 (s, 3H), 3.73 (s, 3H)

Example 37

(E)-methyl 2-(2-((5-((E)-1-(hydroxyimino)ethyl)-2-methoxyphenoxy)-methyl)phenyl)-3-methoxyacrylate (compound 37)

The procedure of Example 2 was repeated with the exception that 3-hydroxy-4-methoxybenzaldehyde was used in Step 1 instead of 2,5-dimethyl-4-methoxybenzaldehyde to obtain the title compound as a white solid (0.5 g, yield 66%).

m/s [M+1]=386.10
$^1$H NMR (300 MHz, CDCl$_3$): δ 7.60-7.56 (m, 2H), 7.33-7.29 (m, 2H), 7.18-7.12 (m, 3H), 6.87-6.84 (d, 1H), 5.06 (s, 2H), 3.90 (s, 3H), 3.81 (s, 3H), 3.68 (s, 3H), 2.16 (s, 3H)

Example 38

(E)-methyl 2-(2-((5-((E)-1-(benzyloxyimino)ethyl)-2-methoxyphenoxy)-methyl)phenyl)-3-methoxyacrylate (compound 38)

The procedure of Example 2 was repeated with the exception that 3-hydroxy-4-methoxybenzaldehyde was used in Step 1 instead of 2,5-dimethyl-4-methoxybenzaldehyde and benzyl bromide was used in Step 4 instead of propyl bromide to obtain the title compound as a yellow solid (0.07 g, yield 61%).

m/s [M+1]=476.10
$^1$H NMR (300 MHz, CDCl$_3$): δ 7.56 (s, H), 7.38-7.23 (m, 8H), 7.15-7.12 (m, 3H), 6.83-6.80 (d, 1H), 5.16 (s, 3H), 5.03 (s, 2H), 3.85 (s, 3H), 3.72 (s, 3H), 3.64 (s, 3H), 2.12 (s, 3H)

Example 39

(E)-methyl 2-(2-((5-((E)-(benzyloxyimino)methyl)-2-methoxyphenoxy)-methyl)phenyl)-3-methoxyacrylate (compound 39)

The procedure of Example 10 was repeated with the exception that 3-hydroxy-4-methoxybenzaldehyde was used in Step 1 instead of 3-hydroxybenzaldehyde and benzyl bromide was used in Step 3 instead of 1-(2-chloroethyl)piperidine to obtain the title compound as a white solid (0.07 g, yield 60%).

m/s [M+1]=462.10
$^1$H NMR (300 MHz, CDCl$_3$): δ 8.00 (s, 1H), 7.59-7.56 (m, 2H), 7.41-7.28 (m, 7H), 7.19-7.16 (m, 1H), 7.10-7.08 (m, 2H), 6.86-6.83 (d, 1H), 5.17 (s, 2H), 5.06 (s, 2H), 3.89 (s, 3H), 3.79 (s, 3H), 3.69 (s, 3H)

Example 40

(E)-methyl 2-(2-((2,5-dimethyl-3-propoxyphenoxy)methyl)phenyl)-3-methoxyacrylate (compound 40)

The procedure of Example 3 was repeated with the exception that 2,5-dimethylbenzene-1,3-diol was used in Step 1 instead of 3-hydroxyphenol and propyl bromide was used in Step 2 instead of benzyl bromide to obtain the title compound as a white solid (0.1 g, yield 84%).

m/s [M+1]=385.10
$^1$H NMR (300 MHz, CDCl$_3$): δ 7.61 (s, 1H), 7.40-7.30 (m, 2H), 7.20-7.17 (dd, 1H), 6.35-6.30 (d, 2H), 4.95 (s, 2H), 3.94-3.72 (t, 2H), 3.84 (s, 3H), 3.72 (s, 3H), 2.29 (s, 3H), 2.14 (s, 3H) 1.88-1.77 (m, 2H), 1.09-1.04 (t, 3H)

Example 41

(E)-methyl 2-(2-((3-(benzyloxy)-2,5-dimethylphenoxy)methyl)phenyl)-3-methoxyacrylate (compound 41)

The procedure of Example 3 was repeated with the exception that 2,5-dimethylbenzene-1,3-diol was used in Step 1 instead of 3-hydroxyphenol to obtain the title compound as a white solid (0.1 g, yield 68%).

m/s [M+1]=433.10
$^1$H NMR (300 MHz, CDCl$_3$): δ 7.60 (s, 1H), 7.42-7.31 (m, 5H), 7.20-7.18 (m, 3H), 6.37-6.33 (m, 3H), 5.02 (s, 2H), 4.96 (s, 2H), 3.85 (s, 3H), 3.74 (s, 3H), 2.26 (s, 3H), 2.23 (s, 3H)

Example 42

(E)-methyl 2-(2-((2-methoxy-5-((E)-1-(propoxyimino)ethyl)phenoxy)-methyl)phenyl)-3-methoxyacrylate (compound 42)

The procedure of Example 2 was repeated with the exception that 3-hydroxy-4-methoxybenzaldehyde was used in Step 1 instead of 2,5-dimethyl-4-methoxybenzaldehyde to obtain the title compound as a white oil (0.05 g, yield 46%).

m/s [M+1]=428.10
$^1$H NMR (300 MHz, CDCl$_3$): δ 7.58-7.56 (m, 2H), 7.35-7.28 (m, 2H), 7.17-7.15 (d, 3H), 6.86-6.83 (d, 1H), 5.06 (s, 2H), 4.12-4.07 (t, 2H), 3.88 (s, 3H), 3.80 (s, 3H), 3.68 (s, 3H), 2.12 (s, 3H), 1.76-1.67 (m, 2H), 0.98-0.93 (t, 3H)

Example 43

(E)-methyl 2-(2-((2-methoxy-5-((E)-(propoxyimino)methyl)phenoxy)-methyl)phenyl)-3-methoxyacrylate (compound 43)

The procedure of Example 10 was repeated with the exception that 3-hydroxy-4-methoxybenzaldehyde was used in Step 1 instead of 3-hydroxybenzaldehyde and propyl bromide was used in Step 3 instead of 1-(2-chloroethyl)piperidine to obtain the title compound as a white solid (0.05 g, yield 46%).

m/s [M+1]=414.10
$^1$H NMR (300 MHz, CDCl$_3$): δ 7.92 (s, 1H), 7.60-7.56 (m, 2H), 7.35-7.26 (m, 2H), 7.17-7.14 (m, 1H), 7.10-7.07 (m, 2H), 6.86-6.83 (d, 1H), 5.05 (s, 2H), 4.09-4.05 (t, 2H), 3.89 (s, 3H), 3.83 (s, 3H), 3.70 (s, 3H), 1.76-1.63 (m, 2H), 0.98-0.93 (t, 3H)

Example 44

(E)-methyl 2-(2-((2-methoxy-5-((E)-1-(phenylethoxyimino)ethyl)-phenoxy)methyl)phenyl)-3-methoxyacrylate (compound 44)

The procedure of Example 2 was repeated with the exception that 3-hydroxy-4-methoxybenzaldehyde was used in Step 1 instead of 2,5-dimethyl-4-methoxybenzaldehyde and phenylethyl bromide was used in Step 4 instead of propyl bromide to obtain the title compound as a white solid (0.02 g, yield 16%).

m/s [M+1]=490.10

1H NMR (300 MHz, CDCl$_3$): δ 7.59-7.56 (m, 2H), 7.35-7.26 (m, 7H), 7.19-7.15 (m, 3H), 6.87-6.84 (d, 1H), 5.07 (s, 2H), 4.37-4.33 (t, 2H), 3.89 (s, 3H), 3.78 (s, 3H), 3.66 (s, 3H), 3.03-2.99 (t, 2H), 2.09 (s, 3H)

Example 45

(E)-methyl 2-(2-((2-methoxy-5-((E)-1-(phenylethoxyimino)methyl)-phenoxy)methyl)phenyl)-3-methoxyacrylate (compound 45)

The procedure of Example 10 was repeated with the exception that 3-hydroxy-4-methoxybenzaldehyde was used in Step 1 instead of 3-hydroxybenzaldehyde and phenylethyl bromide was used in Step 3 instead of 1-(2-chloroethyl)piperidine to obtain the title compound as a brown solid (0.02 g, yield 20%).

m/s [M+1]=476.10

$^1$H NMR (300 MHz, CDCl$_3$): δ 7.91 (s, 1H), 7.57-7.55 (m, 2H), 7.33-7.05 (m, 10H), 6.85-6.82 (d, 1H), 5.04 (s, 2H), 4.33-4.29 (t, 2H), 3.87 (s, H), 3.78 (s, 3H), 3.67 (s, 3H), 3.01-2.96 (t, 2H)

Example 46

(E)-methyl 2-(2-((2-methoxy-5-((E)-1-(phenoxyimino)methyl)phenoxy)-methyl)phenyl)-3-methoxyacrylate (compound 46)

The procedure of Example 10 was repeated with the exception that 3-hydroxy-4-methoxybenzaldehyde was used in Step 1 instead of 3-hydroxybenzaldehyde and phenylhydroxyamine hydrochloride was used in Step 2 instead of hydroxyamine hydrochloride to obtain the title compound as a white solid (0.2 g, yield 42%).

m/s [M+1]=448.10

$^1$H NMR (300 MHz, CDCl$_3$): δ 7.90 (s, 1H), 7.56-7.53 (m, 2H), 7.35-7.06 (m, 10H), 6.83-6.81 (d, 1H), 5.02 (s, 2H), 3.85 (s, H), 3.74 (s, 3H), 3.69 (s, 3H)

Example 47

(E)-methyl 2-(2-((3-((E)-1-(phenoxyimino)methyl)phenoxy)methyl)-phenyl)-3-methoxyacrylate (compound 47)

The procedure of Example 10 was repeated with the exception that 4-hydroxybenzaldehyde was used in Step 1 instead of 3-hydroxybenzaldehyde and phenylhydroxyamine hydrochloride was used in Step 2 instead of hydroxyamine hydrochloride to obtain the title compound as a white solid (0.05 g, yield 31%).

m/s [M+1]=418.10

$^1$H NMR (300 MHz, CDCl$_3$): δ 7.90 (s, 1H), 7.54-7.51 (m, 2H), 7.34-7.08 (m, 10H), 6.81-6.80 (d, 2H), 5.01 (s, 2H), 3.83 (s, H), 3.72 (s, 3H)

Example 48

(E)-methyl 2-(2-((2-methoxy-5-((E)-1-(phenylhydrazono)ethyl)phenoxy)-methyl)phenyl)-3-methoxyacrylate (compound 48)

The procedure of Example 2 was repeated with the exception that 3-hydroxy-4-methoxybenzaldehyde was used in Step 1 instead of 2,5-dimethyl-4-methoxybenzaldehyde and phenylhydrazine was used in Step 3 instead of hydroxyamine hydrochloride to obtain the title compound as a yellow solid (0.07 g, yield 19%).

m/s [M+1]=461.10

$^1$H NMR (300 MHz, CDCl$_3$): δ 7.92 (s, 1H), 7.59-7.55 (m, 2H), 7.41-7.17 (m, 10H), 6.85-6.83 (d, 1H), 5.05 (s, 2H), 3.86 (s, H), 3.77 (s, 3H), 3.71 (s, 3H), 2.35 (s, 3H)

Example 49

(E)-methyl 2-(2-((2,5-dimethyl-4-((E)-(propoxyimino)methyl)phenoxy)-methyl)phenyl)-3-methoxyacrylate (compound 49)

The procedure of Example 10 was repeated with the exception that 4-hydroxy-2,5-dimethylbenzaldehyde was used in Step 1 instead of 3-hydroxybenzaldehyde and propyl bromide was used in Step 3 instead of 1-(2-chloroethyl)piperidine to obtain the title compound as a white solid (0.1 g, yield 93%).

m/s [M+1]=412.10

$^1$H NMR (300 MHz, CDCl$_3$): δ 8.28 (s, 1H), 7.62 (s, 1H), 7.58-7.53 (m, 2H), 7.39-7.31 (m, 2H), 7.21-7.18 (m, 1H), 6.54 (s, 1H), 4.99 (s, 2H), 4.14-4.10 (t, 2H), 3.85 (s, 3H), 3.72 (s, 3H), 2.33 (s, 3H), 2.25 (s, 3H) 1.79-1.72 (m, 2H), 1.02-0.97 (t, 3H)

Example 50

(E)-methyl 2-(2-((4-((E)-(benzyloxyimino)methyl)-2,5-dimethylphenoxy)-methyl)phenyl)-3-methoxyacrylate (compound 50)

The procedure of Example 10 was repeated with the exception that 4-hydroxy-2,5-dimethylbenzaldehyde was used in Step 1 instead of 3-hydroxybenzaldehyde and benzyl bromide was used in Step 3 instead of 1-(2-chloroethyl)piperidine to obtain the title compound as a white solid (0.1 g, yield 72%).

m/s [M+1]=460.10

$^1$H NMR (300 MHz, CDCl$_3$): δ 8.26 (s, 1H), 7.61 (s, 1H), 7.58-7.53 (m, 2H), 7.47-7.33 (m, 7H), 7.21-7.18 (m, 1H), 6.54 (s, 1H), 5.21 (s, 2H), 4.94 (s, 2H), 3.85 (s, 3H), 3.72 (s, 3H), 2.32 (s, 3H), 2.25 (s, 3H)

Example 51

(E)-methyl 2-(2-((2,5-dimethyl-4-((E)-(2-phenoxyethoxyimino)methyl)-phenoxy)methyl)phenyl)-3-methoxyacrylate (compound 51)

The procedure of Example 10 was repeated with the exception that 4-hydroxy-2,5-dimethylbenzaldehyde was used in Step 1 instead of 3-hydroxybenzaldehyde and phenoxyethyl bromide was used in Step 3 instead of 1-(2-chloroethyl)piperidine to obtain the title compound as a white solid (0.05 g, yield 47%).

m/s [M+1]=490.10

$^1$H NMR (300 MHz, CDCl$_3$): δ 8.34 (s, 1H), 7.63 (s, 1H), 7.58-7.55 (dd, 1H), 7.52 (s, 1H), 7.37-7.29 (m, 4H), 7.21-7.18

(dd, 1H), 6.99-6.96 (m, 3H), 6.54 (s, 1H), 4.99 (s, 2H), 4.53-4.50 (t, 2H), 4.31-4.28 (t, 2H), 3.85 (s, 3H), 3.72 (s, 3H), 2.33 (s, 3H), 2.25 (s, 3H)

Example 52

(E)-methyl 2-(2-((2,5-dimethyl-4-((E)-(oxirane-2-ylmethoxyimino)-methyl)phenoxy)methyl)phenyl)-3-methoxyacrylate (compound 52)

The procedure of Example 10 was repeated with the exception that 4-hydroxy-2,5-dimethylbenzaldehyde was used in Step 1 instead of 3-hydroxybenzaldehyde and 2-(chloromethyl)oxirane was used in Step 3 instead of 1-(2-chloroethyl)piperidine to obtain the title compound as a white oil (0.1 g, yield 65%).

m/s [M+1]=426.10

$^1$H NMR (300 MHz, CDCl$_3$): δ 8.33 (s, 1H), 7.63 (s, 1H), 7.58-7.55 (dd, 1H), 7.51 (s, 1H), 7.40-7.31 (m, 2H), 7.21-7.18 (m, 1H), 4.99 (s, 2H), 4.40-4.35 (dd, 1H), 4.14-4.08 (dd, 1H), 3.85 (s, 3H), 3.72 (s, 3H), 3.36-3.31 (m, 1H), 2.91-2.88 (t, 1H), 2.73-2.72 (dd, 1H), 2.34 (s, 3H), 2.25 (s, 3H)

Example 53

(E)-methyl 2-(2-((2,5-dimethyl-4-((E)-(2-(pyrrolidin-1-yl)ethoxyimino)-methyl)phenoxy)methyl)phenyl)-3-methoxyacrylate (compound 53)

The procedure of Example 10 was repeated with the exception that 4-hydroxy-2,5-dimethylbenzaldehyde was used in Step 1 instead of 3-hydroxybenzaldehyde and 1-(2-chloroethyl)pyrrolidine was used in Step 3 instead of 1-(2-chloroethyl)piperidine to obtain the title compound as a white oil (0.07 g, yield 44%).

m/s [M+1]=467.10

$^1$H NMR (300 MHz, CDCl$_3$): δ 7.61 (s, 1H), 7.60-7.59 (m, 1H), 7.40-7.30 (m, 2H), 7.19-7.16 (dd, 1H), 6.36-6.31 (d, 2H), 4.94 (s, 2H), 4.13-4.09 (t, 2H), 3.82 (s, 3H), 3.72 (s, 3H), 2.95-2.91 (t, 2H), 2.68-2.64 (m, 4H), 2.28 (s, 3H), 2.13 (s, 3H), 1.84-1.79 (m, 4H)

Example 54

(E)-methyl 2-(2-((2,5-dimethyl-4-((E)-(2-(piperidin-1-yl)ethoxyimino)-methyl)phenoxy)methyl)phenyl)-3-methoxyacrylate (compound 54)

The procedure of Example 10 was repeated with the exception that 4-hydroxy-2,5-dimethylbenzaldehyde was used in Step 1 instead of 3-hydroxybenzaldehyde and 1-(2-chloroethyl)piperidine was used in Step 3 instead of 1-(2-chloroethyl)piperidine to obtain the title compound as a yellow oil (0.06 g, yield 41%).

m/s [M+1]=481.10

$^1$H NMR (300 MHz, CDCl$_3$): δ 7.61 (s, 1H), 7.39-7.29 (m, 2H), 7.19-7.16 (dd, 1H), 6.36-6.30 (dd, 3H), 4.94 (s, 2H), 4.12-4.08 (m, 2H), 3.83 (s, 3H), 3.71 (s, 3H), 2.84-2.80 (m, 2H), 2.57-2.44 (m, 4H), 2.31 (s, 3H), 2.28 (s, 3H), 1.64-1.59 (m, 4H), 1.47-1.45 (m, 2H)

Example 55

(E)-methyl 2-(2-((3-hydroxy-2,5-dimethylphenoxy)methyl)phenyl)-3-methoxyacrylate (compound 55)

The same procedure as Step 1 of Example 3 was repeated with the exception that 2,5-dimethylbenzene-1,3-diol was used instead of 3-hydroxyphenol to obtain the title compound as a white solid (0.3 g, yield 38%).

m/s [M+1]=343.10

$^1$H NMR (300 MHz, CDCl$_3$): δ 7.62 (s, 1H), 7.60-7.59 (m, 1H), 7.40-7.30 (m, 2H), 7.20-7.17 (dd, 1H), 6.29-6.25 (d, 2H), 4.94 (s, 2H), 3.84 (s, 3H), 3.72 (s, 3H), 2.24 (s, 3H), 2.14 (s, 3H)

Example 56

(E)-methyl 2-(2-((2,5-dimethyl-3-(2-phenoxyethoxy)phenoxy)methyl)-phenyl)-3-methoxyacrylate (compound 56)

The procedure of Example 3 was repeated with the exception that 2,5-dimethylbenzene-1,3-diol was used in Step 1 instead of 3-hydroxyphenol and phenoxyethyl bromide was used in Step 2 instead of benzyl bromide to obtain the title compound as a white oil (0.06 g, yield 33%).

m/s [M+1]=463.10

$^1$H NMR (300 MHz, CDCl$_3$): δ 7.62 (s, 1H), 7.60-7.59 (m, 1H), 7.37-7.29 (m, 5H), 7.20-7.17 (m, 1H), 7.01-6.97 (m, 2H) 6.41-6.33 (d, 2H), 4.95 (s, 2H), 4.36-4.31 (m, 4H), 3.84 (s, 3H), 3.72 (s, 3H), 2.30 (s, 3H), 2.13 (s, 3H)

Example 57

(E)-methyl 2-(2-((2-methoxy-5-((E)-1-(4-methylbenzyloxyimino)ethyl)-phenoxy)methyl)phenyl)-3-methoxyacrylate (compound 57)

The procedure of Example 2 was repeated with the exception that 3-hydroxy-4-methoxybenzaldehyde was used in Step 1 instead of 2,5-dimethyl-4-methoxybenzaldehyde and 1-(bromomethyl)-4-methylbenzene was used in Step 4 instead of propyl bromide to obtain the title compound as a yellow oil (0.05 g, yield 26%).

m/s [M+1]=474.10

$^1$H NMR (300 MHz, CDCl$_3$): δ 7.60-7.57 (m, 2H), 7.35-7.20 (m, 4H), 7.16-7.14 (m, 5H), 6.85-6.83 (d, 1H), 5.15 (s, 2H), 5.07 (s, 2H), 3.87 (s, 3H), 3.76 (s, 3H), 3.68 (s, 3H), 2.34 (s, 3H), 2.15 (s, 3H)

Example 58

(E)-methyl 2-(2-((2-methoxy-5-((E)-1-(4-methylbenzyloxyimino)methyl)-phenoxy)methyl)phenyl)-3-methoxyacrylate (compound 58)

The procedure of Example 10 was repeated with the exception that 3-hydroxy-4-methoxybenzaldehyde was used in Step 1 instead of 3-hydroxybenzaldehyde and 1-(bromomethyl)-4-methylbenzene was used in Step 3 instead of 1-(2-chloroethyl)piperidine to obtain the title compound as a brown oil (0.1 g, yield 82%).

m/s [M+1]=460.10

$^1$H NMR (300 MHz, CDCl$_3$): δ 7.97 (s, 1H), 7.58-7.55 (d, 2H), 7.34-7.26 (m, 3H), 7.18-7.13 (m, 3H), 7.08-7.05 (m, 2H), 6.84-6.81 (d, 1H), 5.11 (s, 2H), 5.05 (s, 2H), 3.87 (s, 3H), 3.77 (s, 3H), 3.68 (s, 3H), 2.33 (s, 3H)

Example 59

(E)-methyl 2-(2-((2-methyl-4-((E)-(phenylethoxyimino)methyl)phenoxy)-methyl)phenyl)-3-methoxyacrylate (compound 59)

The procedure of Example 10 was repeated with the exception that 4-hydroxy-3-methylbenzaldehyde was used in Step 1 instead of 3-hydroxybenzaldehyde and phenylethyl bromide was used in Step 3 instead of 1-(2-chloroethyl)piperidine to obtain the title compound as a white solid (0.02 g, yield 21%).

m/s [M+1]=460.10

$^1$H NMR (300 MHz, CDCl$_3$): δ 7.89 (s, 1H), 7.49 (s, 1H), 7.45-7.42 (m, 1H), 7.34-7.05 (m, 10H), 6.64-6.62 (d, 1H), 4.89 (s, 2H), 4.26-4.21 (t, 2H), 3.71 (s, 3H), 3.566 (s, 3H), 2.95-2.90 (t, 2H), 2.19 (s, 3H)

Example 60

(E)-methyl 2-(2-((2-methyl-4-((E)-(4-methylbenzyloxyimino)methyl)-phenoxy)methyl)phenyl)-3-methoxyacrylate (compound 60)

The procedure of Example 10 was repeated with the exception that 4-hydroxy-3-methylbenzaldehyde was used in Step 1 instead of 3-hydroxybenzaldehyde and 1-(bromomethyl)-4-methylbenzene was used in Step 3 instead of 1-(2-chloroethyl)piperidine to obtain the title compound as a white solid (0.1 g, yield 87%).

m/s [M+1]=460.10

$^1$H NMR (300 MHz, CDCl$_3$): δ 8.03 (s, 1H), 7.59 (s, 1H) 7.55-7.52 (m, 1H), 7.43-7.43 (d, 1H), 7.34-7.29 (m, 4H), 7.26-7.23 (m, 1H), 7.19-7.16 (m, 3H), 6.74-6.71 (d, 1H), 5.13 (s, 2H), 5.00 (s, 2H), 3.80 (s, 3H), 3.69 (s, 3H), 2.34 (s, 3H), 2.27 (s, 3H)

Example 61

(E)-methyl 2-(2-((4-((E)-(benzyloxyimino)methyl)-2-fluoro-6-methoxyphenoxy)methyl)phenyl)-3-methoxyacrylate (compound 61)

The procedure of Example 10 was repeated with the exception that 4-fluoro-3-hydroxy-2-methoxybenzaldehyde was used in Step 1 instead of 3-hydroxybenzaldehyde and benzyl bromide was used in Step 3 instead of 1-(2-chloroethyl)piperidine to obtain the title compound as a yellow solid (0.08 g, yield 67%).

m/s [M+1]=480.10

$^1$H NMR (300 MHz, CDCl$_3$): δ 7.29-7.15 (m, 8H), 7.02-6.99 (m, 1H), 6.81-6.73 (m, 2H), 5.07 (s, 2H), 4.88 (s, 2H), 3.71 (s, 3H), 3.62 (s, 3H), 3.52 (s, 3H)

Example 62

(E)-methyl 2-(2-((3-(benzyloxy)-2,4-difluorophenoxy)methyl)phenyl)-3-methoxyacrylate (compound 62)

The procedure of Example 3 was repeated with the exception that 2,5-difluorobenzene-1,3-diol was used in Step 1 instead of 3-hydroxyphenol to obtain the title compound as a white solid (0.06 g, yield 77%).

m/s [M+1]=441.10

$^1$H NMR (300 MHz, CDCl$_3$): δ 7.75-7.72 (m, 1H), 7.62 (s, 1H), 7.46-7.33 (m, 7H), 7.20-7.17 (m, 1H), 6.80-6.60 (m, 2H), 5.10 (s, 2H), 3.81 (s, 3H), 3.70 (s, 3H)

Example 63

(E)-methyl 2-(2-((2,5-dimethyl-4-((E)-(phenoxyimino)methyl)phenoxy)-methyl)phenyl)-3-methoxyacrylate (compound 63)

The procedure of Example 10 was repeated with the exception that 4-hydroxy-2,5-dimethylbenzaldehyde was used in Step 1 instead of 3-hydroxybenzaldehyde and phenylhydroxyamine hydrochloride was used in Step 2 instead of hydroxyamine hydrochloride to obtain the title compound as a yellow solid as a white oil (0.07 g, yield 45%).

m/s [M+1]=446.10

$^1$H NMR (300 MHz, CDCl$_3$): δ 8.60 (s, 1H), 7.62 (s, 1H), 7.59-7.56 (m, 1H), 7.39-7.31 (m, 4H), 7.25-7.16 (m, 3H), 7.07-6.98 (m, 2H) 6.60 (s, 1H), 5.02 (s, 2H), 3.86 (s, 3H), 3.74 (s, 3H), 2.44 (s, 3H), 2.29 (s, 3H)

Example 64

(E)-methyl 2-(2-((2-fluoro-6-methoxy-4-((E)-(propoxyimino)methyl)-phenoxy)methyl)phenyl)-3-methoxyacrylate (compound 64)

The procedure of Example 10 was repeated with the exception that 4-fluoro-3-hydroxy-2-methoxybenzaldehyde was used in Step 1 instead of 3-hydroxybenzaldehyde and propyl bromide was used in Step 3 instead of 1-(2-chloroethyl)piperidine to obtain the title compound as a white solid (0.06 g, yield 60%).

m/s [M+1]=432.10

$^1$H NMR (300 MHz, CDCl$_3$): δ 7.91 (s, 1H), 7.74-7.71 (d, 1H), 7.54 (s, 1H), 7.37-7.29 (m, 2H), 7.12-7.09 (dd, 1H), 6.92-6.92 (s, 1H), 6.87-6.83 (dd, 1H), 4.97 (s, 2H), 4.11-4.06 (t, 2H), 3.84 (s, 3H), 3.75 (s, 3H), 3.63 (s, 3H), 1.76-1.64 (m, 2H), 0.97-0.93 (t, 3H)

Example 65

(E)-methyl 2-(2-((2,4-difluoro-3-propoxyphenoxy) methyl)phenyl)-3-methoxyacrylate (compound 65)

The procedure of Example 3 was repeated with the exception that 2,5-difluorobenzene-1,3-diol was used in Step 1 instead of 3-hydroxyphenol and propyl bromide was used in Step 2 instead of benzyl bromide to obtain the title compound as a white oil (0.05 g, yield 58%).

m/s [M+1]=393.10

$^1$H NMR (300 MHz, CDCl$_3$): δ 7.71-7.68 (dd, 1H), 7.38-7.28 (m, 2H), 7.15-7.12 (dd, 1H), 6.77-6.69 (m, 1H), 6.59-6.51 (m, 1H), 5.05 (s, 2H), 3.93-3.88 (t, 2H), 3.77 (s, 3H), 3.65 (s, 3H), 1.85-1.73 (m, 2H), 1.04-0.99 (t, 3H)

Example 66

(E)-methyl 2-(2-((2-fluoro-6-methoxy-4-((E)-(phenethoxyimino)methyl)-phenoxy)methyl)phenyl)-3-methoxyacrylate (compound 66)

The procedure of Example 10 was repeated with the exception that 4-fluoro-3-hydroxy-2-methoxybenzaldehyde was used in Step 1 instead of 3-hydroxybenzaldehyde and phenylethyl bromide was used in Step 3 instead of 1-(2-chloroethyl)piperidine to obtain the title compound as a white solid (0.01 g, yield 12%).

m/s [M+1]=494.10

$^1$H NMR (300 MHz, CDCl$_3$): δ 7.82 (s, 1H), 7.65-7.62 (dd, 1H), 7.45 (s, 1H), 7.27-7.10 (m, 7H), 7.03-7.01 (dd, 1H), 6.83-6.74 (m, 2H), 4.89 (s, 2H), 4.27-4.23 (t, 2H), 3.75 (s, 3H), 3.65 (s, 3H), 3.54 (s, 3H), 2.93-2.88 (t, 2H)

Example 67

(E)-methyl 2-(2-((4-((E)-(cyclopropylmethoxyimino) methyl)-2-methylphenoxy)methyl)phenyl)-3-methoxyacrylate (compound 67)

The procedure of Example 10 was repeated with the exception that 4-hydroxy-3-methylbenzaldehyde was used in Step 1 instead of 3-hydroxybenzaldehyde and (bromomethyl)cyclopropane was used in Step 3 instead of 1-(2-chloroethyl)piperidine to obtain the title compound as a yellow solid (0.07 g, yield 67%).

m/s [M+1]=410.10

$^1$H NMR (300 MHz, CDCl$_3$): δ 8.04 (s, 1H), 7.61 (s, 1H), 7.58-7.55 (m, 1H), 7.45 (s, 1H), 7.37-7.33 (m, 2H), 7.28-7.25 (m, 1H), 7.21-7.19 (m, 1H), 6.77-6.74 (d, 1H), 5.02 (s, 2H), 3.99-3.97 (d, 2H), 3.84 (s, 3H), 3.72 (s, 3H), 2.30 (s, 3H), 1.26-1.19 (m, 1H), 0.63-0.57 (m, 2H), 0.36-0.33 (m, 2H)

Example 68

(E)-methyl 2-(2-((4-((E)-(cyclopropylmethoxyimino) methyl)-2,5-dimethylphenoxy)methyl)phenyl)-3-methoxyacrylate (compound 68)

The procedure of Example 10 was repeated with the exception that 4-hydroxy-2,5-dimethylbenzaldehyde was used in Step 1 instead of 3-hydroxybenzaldehyde and (bromomethyl)cyclopropane was used in Step 3 instead of 1-(2-chloroethyl)piperidine to obtain the title compound as a white solid (0.08 g, yield 77%).

m/s [M+1]=424.10

$^1$H NMR (300 MHz, CDCl$_3$): δ 8.32 (s, 1H), 7.63 (s, 1H), 7.58-7.55 (m, 1H), 7.52 (s, 1H), 7.40-7.30 (m, 2H), 7.21-7.18 (m, 1H), 6.54 (s, 1H), 4.99 (s, 2H), 4.00-3.98 (d, 2H), 3.85 (s, 3H), 3.72 (s, 3H), 2.34 (s, 3H), 2.25 (s, 3H), 1.28-1.19 (m, 1H), 0.64-0.57 (m, 2H), 0.37-0.32 (m, 2H)

Example 69

(E)-methyl 2-(2-((4-((E)-(cyclopentyloxyimino)methyl)-2,5-dimethylphenoxy)methyl)phenyl)-3-methoxyacrylate (compound 69)

The procedure of Example 10 was repeated with the exception that 4-hydroxy-2,5-dimethylbenzaldehyde was used in Step 1 instead of 3-hydroxybenzaldehyde and bromocyclopentane was used in Step 3 instead of 1-(2-chloroethyl)piperidine to obtain the title compound as a white oil (0.06 g, yield 52%).

m/s [M+1]=438.10

$^1$H NMR (300 MHz, CDCl$_3$): δ 8.20 (s, 1H), 7.59 (s, 1H), 7.55-7.52 (m, 1H), 7.49 (s, 1H), 7.36-7.27 (m, 2H), 7.17-7.14 (m, 1H), 6.50 (s, 1H), 4.95 (s, 2H), 4.77-4.73 (m, 1H), 3.81 (s, 3H), 3.68 (s, 3H), 2.29 (s, 3H), 2.21 (s, 3H), 1.83-1.68 (m, 4H), 1.62-1.52 (m, 4H)

Example 70

(E)-methyl 2-(2-((4-((E)-(cyclopentyloxyimino)methyl)-2-methylphenoxy)methyl)phenyl)-3-methoxyacrylate (compound 70)

The procedure of Example 10 was repeated with the exception that 4-hydroxy-3-methylbenzaldehyde was used in Step 1 instead of 3-hydroxybenzaldehyde and bromocyclopentane was used in Step 3 instead of 1-(2-chloroethyl)piperidine to obtain the title compound as a white solid (0.04 g, yield 35%).

m/s [M+1]=424.10

$^1$H NMR (300 MHz, CDCl$_3$): δ 7.97 (s, 1H), 7.61 (s, 1H), 7.57-7.54 (m, 1H), 7.46-7.45 (m, 1H), 7.39-7.30 (m, 2H), 7.24-7.17 (m, 2H), 6.76-6.73 (d, 1H), 5.01 (s, 2H), 4.80-4.74 (m, 1H), 3.84 (s, 3H), 3.72 (s, 3H), 2.29 (s, 3H), 1.85-1.82 (m, 4H), 1.72-1.71 (m, 4H)

Example 71

(E)-methyl 2-(2-((2,5-dimethyl-4-((E)-(3-phenoxypropyloxyimino)-methyl)phenoxy)methyl)phenyl)-3-methoxyacrylate (compound 71)

The procedure of Example 10 was repeated with the exception that 4-hydroxy-2,5-dimethylbenzaldehyde was used in Step 1 instead of 3-hydroxybenzaldehyde and phenoxypropyl bromide was used in Step 3 instead of 1-(2-chloroethyl)piperidine to obtain the title compound as a white solid (0.08 g, yield 51%).

m/s [M+1]=504.10

$^1$H NMR (300 MHz, CDCl$_3$): δ 8.28 (s, 1H), 7.63 (s, 1H), 7.59-7.52 (m, 2H), 7.40-7.30 (m, 4H), 7.21-7.18 (m, 1H), 6.98-6.92 (m, 2H) 6.54 (s, 1H), 4.99 (s, 2H), 4.38-4.34 (t, 2H), 4.17-4.11 (t, 2H), 3.85 (s, 3H), 3.72 (s, 3H), 2.34 (s, 3H), 2.25 (s, 3H)

Example 72

(E)-methyl 2-(2-((4-((E)-(3-methoxybenzyloxyimino)methyl)-2,5-dimethylphenoxy)methyl)phenyl)-3-methoxyacrylate (compound 72)

The procedure of Example 10 was repeated with the exception that 4-hydroxy-2,5-dimethylbenzaldehyde was used in Step 1 instead of 3-hydroxybenzaldehyde and 1-(bromomethyl)-3-methoxybenzene was used in Step 3 instead of 1-(2-chloroethyl)piperidine to obtain the title compound as a yellow oil (0.1 g, yield 75%).

m/s [M+1]=490.10

$^1$H NMR (300 MHz, CDCl$_3$): δ 8.34 (s, 1H), 7.63 (s, 1H), 7.58-7.53 (m, 2H), 7.40-7.30 (m, 3H), 7.21-7.18 (dd, 1H), 7.04-7.00 (m, 2H), 6.89-6.86 (dd, 1H) 6.54 (s, 1H), 5.18 (s, 2H), 4.99 (s, 2H), 3.85 (s, 3H), 3.72 (s, 3H), 2.33 (s, 3H), 2.25 (s, 3H)

Example 73

(E)-methyl 2-(2-((4-((E)-(pyridin-2-ylmethoxyimino)methyl)-2,5-dimethylphenoxy)methyl)phenyl)-3-methoxyacrylate (compound 73)

The procedure of Example 10 was repeated with the exception that 4-hydroxy-2,5-dimethylbenzaldehyde was used in Step 1 instead of 3-hydroxybenzaldehyde and 2-(bromomethyl)pyridine was used in Step 3 instead of 1-(2-chloroethyl)piperidine to obtain the title compound as a white (0.04 g, yield 27%).

m/s [M+1]=461.10

$^1$H NMR (300 MHz, CDCl$_3$): δ 8.63-8.61 (td, 1H), 8.42 (s, 1H), 7.74-7.68 (dt, 1H), 7.62 (s, 1H), 7.57-7.53 (m, 2H), 7.40-7.30 (m, 3H), 7.21-7.18 (dd, 1H), 7.04-7.00 (m, 2H), 6.89-6.86 (dd, 1H) 6.54 (s, 1H), 5.18 (s, 2H), 4.99 (s, 2H), 3.85 (s, 3H), 3.72 (s, 3H), 2.33 (s, 3H), 2.25 (s, 3H)

Example 74

(E)-methyl 2-(2-((4-((E)-(pyridin-4-ylmethoxy-imino)methyl)-2,5-dimethylphenoxy)methyl)phenyl)-3-methoxyacrylate (compound 74)

The procedure of Example 10 was repeated with the exception that 4-hydroxy-2,5-dimethylbenzaldehyde was used in Step 1 instead of 3-hydroxybenzaldehyde and 4-(bromomethyl)pyridine was used in Step 3 instead of 1-(2-chloroethyl) piperidine to obtain the title compound as a white oil (0.07 g, yield 46%).

m/s [M+1]=461.10

$^1$H NMR (300 MHz, CDCl$_3$): δ 8.62-8.60 (td, 1H), 8.38 (s, 1H), 7.63 (s, 1H), 7.57-7.54 (m, 1H), 7.47 (m, 3H), 7.21-7.18 (s, 1H), 7.39-7.31 (m, 4H), 7.21-7.18 (m, 2H) 6.54 (s, 1H), 5.21 (s, 2H), 4.99 (s, 2H), 3.85 (s, 3H), 3.72 (s, 3H), 2.33 (s, 3H), 2.24 (s, 3H)

Example 75

(E)-methyl 2-(2-((3-((E)-(2-phenoxyethoxyimino) methyl)phenoxy)-methyl)phenyl)-3-methoxyacrylate (compound 75)

The procedure of Example 10 was repeated with the exception that phenoxyethyl bromide was used in Step 3 instead of 1-(2-chloroethyl)piperidine to obtain the title compound as a yellow oil (4.00 g, yield 70%).

m/s [M+1]=462.10

$^1$H NMR (300 MHz, CDCl$_3$): δ 8.05 (s, 1H), 7.55 (s, 1H), 7.53-7.50 (m, 8H), 7.31-7.10 (m, 8H), 6.93-6.87 (m, 4H), 5.18 (s, 2H), 4.96 (s, 2H), 4.49-4.46 (t, 2H), 4.23-4.20 (t, 2H), 3.73 (s, 3H), 3.66 (s, 3H)

Example 76

(E)-methyl 2-(2-((3-(2-morpholinoethoxy)phenoxy) methyl)phenyl)-3-methoxyacrylate (compound 76)

The procedure of Example 3 was repeated with the exception that 4-(2-chloroethyl)morpholine hydrochloride was used in Step 2 instead of benzyl bromide to obtain the title compound as a white solid (2.00 g, yield 67%).

m/s [M+1]=448.3

$^1$H NMR (300 MHz, CDCl$_3$): δ 7.60 (s, 1H), 7.60-7.12 (m, 5H), 6.52-6.46 (m, 3H), 4.95 (s, 2H), 4.12 (t, 2H), 3.80 (s, 3H), 3.78 (m, 4H), 3.75 (s, 3H), 2.78 (t, 2H), 2.60 (m, 4H),

Example 77

(E)-methyl 2-(2-((2,5-dimethyl-4-((E)-1-(methoxy-imino)ethyl)phenoxy)-methyl)phenyl)-3-methoxy-acrylate (compound 77)

<Step 1>

(E)-methyl 2-(2-(bromomethyl)phenyl)-3-methoxyacrylate (20 g, 70.1 mmol) was reacted with 2,5-dimethylphenol (8.56 g, 1.0 eq) in 400 mL of acetonitrile (CH$_3$CN) in the presence of potassium hydroxide (4.65 g, 1.1 eq) at room temperature for 4 hours, followed by removing the reaction solvent by concentration in a vacuum. The residue was stirred in water (200 mL) and the aqueous layer was extracted twice with 200 mL of dichloromethane. The organic layer thus obtained was dried over anhydrous magnesium sulfate, filtered and concentrated in a vacuum to remove the solvent. The residue was purified using silica gel chromatography to give (E)-methyl 2-(2-((2,5-dimethylphenoxy)methyl)phenyl)-3-methoxyacrylate as a white solid (18.5 g, yield 81%).

$^1$H NMR (300 MHz, CDCl$_3$): δ 7.64 (s, 1H), 7.62 (s, 1H), 7.36 (m, 2H), 7.19 (d, 1H), 7.03 (d, 1H), 6.68 (d, 1H), 6.62 (s, 1H), 4.98 (s, 2H), 3.85 (s, 3H), 3.73 (s, 3H), 2.31 (s, 3H), 2.27 (s, 3H)

<Step 2>

Acetic anhydride (26 mL, 5 eq) was stirred together with methane sulfonyl (18 mL, 5 eq) at room temperature for 30 min and then combined with 18.0 g (55.16 mmol) of (E)-methyl 2-(2-((2,5-dimethylphenoxy)methyl)phenyl)-3-methoxyacrylate obtained in step 1 at room temperature for an additional one hour. After completion of the reaction, the reaction mixture was dropwise added to water (500 mL), adjusted to pH 7 with 25%-NaOH and extracted twice with 250 mL of dichloromethane. The organic layer was dried over anhydrous magnesium sulfate and filtered after which the solvent was removed by concentration in a vacuum. Crystallization in 100 mL of isopropyl ether (IPE) afforded 16.5 g of (E)-methyl 2-(2-((4-acetyl-2,5-dimethylphenoxy)methyl) phenyl)-3-methoxyacrylate in 81% yield as an ivory solid.

$^1$H-NMR (CDCl$_3$): 7.64 (s, 1H), 7.59~7.54 (m, 2H), 7.36 (m, 2H), 7.20 (d, 1H), 6.60 (s, 1H), 5.04 (s, 2H), 3.86 (s, 3H), 3.73 (s, 3H), 2.55 (s, 3H), 2.51 (s, 3H), 2.29 (s, 3H)

<Step 3>

A solution of 10.0 g (27.14 mmol) of (E)-methyl 2-(2-((4-acetyl-2,5-dimethylphenoxy)methyl)phenyl)-3-methoxy-acrylate obtained in Step 2 and 4.53 g (2 eq) of methoxyamine hydrochloride in 200 mL of methanol was stirred at room temperature for 4 hours and concentrated in a vacuum. The residue was stirred in water (150 mL) and extracted twice with 200 mL of dichloromethane. The organic layer was dried over anhydrous magnesium sulfate and concentrated in a vacuum, followed by purification using silica gel chromatography to afford (E)-methyl 2-(2-((2,5-dimethyl-4-((E)-1-(methoxyimino)ethyl)phenoxy)methyl)phenyl)-3-methoxy-acrylate (compound 77) as a white solid (8.0 g, yield: 72.4%).

$^1$H-NMR (CDCl$_3$): 7.63 (s, 1H), 7.58 (d, 1H), 7.35 (m, 2H), 7.19 (d, 1H), 7.02 (s, 1H), 6.58 (s, 1H), 4.98 (s, 2H), 3.97 (s, 3H), 3.86 (s, 3H), 3.73 (s, 3H), 2.29 (s, 3H), 2.25 (s, 3H), 2.15 (s, 3H)

Example 78

(E)-methyl 2-(2-((2,5-dimethyl-4-((E)-1-(ethoxy-imino)ethyl)phenoxy)-methyl)phenyl)-3-methoxy-acrylate (compound 78)

A solution of 1.00 g (2.7 mmol) of the compound obtained in Step 2 of Example 77 and 0.53 g (2 eq) of ethoxyamine in 30 mL of methanol was stirred at room temperature for 4 hours and concentrated in a vacuum. The residue was stirred in water (30 mL) and extracted twice with 30 mL of dichloromethane. The organic layer was dried over anhydrous magnesium sulfate and concentrated in a vacuum, followed by purification using silica gel chromatography to afford (E)-methyl 2-(2-((2,5-dimethyl-4-((E)-1-(ethoxyimino)ethyl) phenoxy)methyl)phenyl)-3-methoxyacrylate (compound 78) as a white solid (0.90 g, yield: 81.1%).

$^1$H NMR (300 MHz, CDCl$_3$): δ 7.62 (s, 1H), 7.58-7.56 (m, 1H), 7.38-7.32 (m, 2H), 7.20-7.18 (m, 1H), 7.01 (s, 1H), 6.57

(s, 1H), 4.98 (s, 2H), 4.20-4.18 (q, 2H), 3.85 (s, 3H), 3.73 (s, 3H), 2.29 (s, 3H), 2.25 (s, 3H), 2.16 (s, 3H), 1.33 (t, 3H)

Example 79

(E)-methyl 2-(2-((2,5-dimethyl-4-((E)-1-(pyridin-2-ylmethoxyimino)-ethyl)phenoxy)methyl)phenyl)-3-methoxyacrylate (compound 79)

<Step 1>

In 30 mL of methanol, 2.0 g (5.43 mmol) of the compound obtained in Step 2 was reacted with 0.75 g (2 eq) of hydroxylamine hydrochloride in the presence of a molecular sieve for dehydration at room temperature for 5 hours with stirring, followed by filtration through celite. The filtrate was concentrated at a reduced pressure and the residue was stirred in water (20 mL). The aqueous layer was extracted twice with 30 mL of dichloromethane. The organic layer was dried over anhydrous magnesium sulfate. Purification by chromatography afforded (E)-methyl 2-(2-((hydroxyimino)ethyl-2,5-dimethylphenoxy)methyl)phenyl)-3-methoxyacrylate as a white solid (1.8 g, yield: 85%).

$^1$H NMR (300 MHz, CDCl$_3$): δ 7.63 (s, 1H), 7.61 (d, 1H), 7.57 (m, 2H), 7.18 (d, 1H), 7.02 (s, 1H), 6.59 (s, 1H), 4.97 (s, 2H), 3.85 (s, 3H), 3.73 (s, 3H), 2.28 (s, 3H), 2.25 (s, 3H), 2.20 (s, 3H)

<Step 2>

To a solution of 1.50 g (3.5 mmol) of (E)-methyl 2-(2-((hydroxyimino)ethyl-2,5-dimethylphenoxy)methyl)phenyl)-3-methoxyacrylate obtained in Step 1 and cesium carbonate 2.8 g (2.2 eq) of cesium carbonate in 30 mL of acetonitrile (CH$_3$CN) was added 2-bromomethylpyridine hydrochloride (1.18 g, 1.2 eq), followed by stirring at room temperature for 2 hours. After completion of the reaction, the solvent was removed at a reduced pressure, and the residue was stirred in water (30 mL) and extracted twice with 30 mL of dichloromethane. The organic layer was dried over anhydrous magnesium sulfate and concentrated in a vacuum, followed by purification by silica gel chromatography to afford 1.4 g of (E)-methyl 2-(2-((2,5-dimethyl-4-((E)-1-(pyridin-2-ylmethoxyimino)ethyl)phenoxy)methyl)phenyl)-3-methoxyacrylate as a white solid (yield: 76%).

$^1$H NMR (300 MHz, CDCl$_3$): δ 8.60 (d, 1H), 7.71 (s, 1H), 7.65-7.18 (m, 7H), 7.02 (s, 1H), 6.58 (s, 1H), 5.34 (s, 2H), 4.97 (s, 2H), 3.85 (s, 3H), 3.72 (s, 3H), 3.51 (s, 3H), 2.27 (s, 3H), 2.24 (s, 3H), 2.23 (s, 3H)

Example 80

(E)-methyl 3-methoxy-2-(2-((4-((Z)-2-methoxy-1-(methoxyimino)ethyl)-2,5-dimethylphenoxy)methyl)phenyl)acrylate (compound 80)

<Step 1>

In 30 mL of methanol, 0.4 g (2.0 mmol) 2-chloro-1-(4-hydroxy-2,5-dimethylphenyl)ethanone was reacted with 0.40 g (7.55 mmol) sodium methoxide at room temperature for 5 hours with stirring, and the solvent was removed at a reduced pressure. To the residue was added 20 mL of water, followed by adjusting the pH to 7 with conc. HCl. The aqueous layer was extracted twice with 3 mL of dichloromethane and the organic layer was dried over anhydrous magnesium sulfate and concentrated at a reduced pressure to afford a yellowish solid compound 1-(4-hydroxy-2,5-dimethylphenyl)-2-methoxyethanone (0.30 g, yield: 78%).

$^1$H NMR (300 MHz, CDCl$_3$): δ 7.48 (s, 1H), 6.67 (s, 1H), 5.12 (s, 1H), 4.57 (s, 2H), 3.50 (s, 3H), 2.52 (s, 3H), 2.27 (s, 3H)

<Step 2>

In 30 mL of acetonitrile (CH$_3$CN), 0.3 g (1.55 mmol) of 1-(4-hydroxy-2,5-dimethylphenyl)-2-methoxyethanone obtained in Step 1 was reacted for 4 hours with 0.44 g (1.55 mmol) of (E)-methyl 2-(2-(bromomethyl)phenyl)-3-methoxyacrylate in the presence of 20.45 g (2.1 eq) of potassium carbonate under reflux. After completion of the reaction, the solvent was removed at a reduced pressure and the residue was stirred in water (30 mL) and extracted twice with 30 mL of dichloromethane. The organic layer was dried over anhydrous magnesium sulfate and concentrated in a vacuum, followed by purification with silica gel to afford 0.47 g of (E)-methyl 3-methoxy-2-(2-((4-(2-methoxyacetyl)-2,5-dimethylphenoxy)methyl)phenyl)acrylate as a white solid (yield: 76%).

$^1$H NMR (300 MHz, CDCl$_3$): δ 7.64 (s, 1H), 7.56~7.53 (m, 1H), 7.47 (s, 1H), 7.38~7.34 (m, 2H), 7.22~7.19 (1H), 6.62 (s, 1H), 5.04 (s, 2H), 4.57 (s, 2H), 3.86 (s, 3H), 3.73 (s, 3H), 3.50 (s, 3H), 2.51 (s, 3H), 2.28 (s, 3H)

<Step 3>

In 30 mL of methanol, 0.2 g (0.50 mmol) of (E)-methyl 3-methoxy-2-(2-((4-(2-methoxyacetyl)-2,5-dimethylphenoxy)methyl)phenyl)acrylate obtained in Step 2 was reacted with 0.21 g (5 eq) of methoxyamine hydrochloride at room temperature for 15 hours with stirring. After completion of the reaction, the solvent was removed in a vacuum, and the residue was stirred in water (30 mL) and extracted twice with 30 mL of dichloromethane. The organic layer was dried over anhydrous magnesium sulfate and concentrated in a vacuum. Purification by silica gel chromatography afforded 0.1 g of (E)-methyl 3-methoxy-2-(2-((4-((Z)-2-methoxy-1-(methoxyimino)ethyl)2,5-dimethylphenoxy)methyl)phenyl)acrylate as a white solid (yield: 50%).

$^1$H NMR (300 MHz, CDCl$_3$): δ 7.62 (s, 1H), 7.60~7.57 (m, 1H), 7.39~7.30 (m, 2H), 7.20~7.17 (m, 1H), 7.06 (s, 1H), 6.59 (s, 1H), 4.97 (s, 2H), 4.51 (s, 2H), 3.96 (s, 3H), 3.85 (s, 3H), 3.73 (s, 3H), 3.28 (s, 3H), 2.29 (s, 3H), 2.24 (s, 3H)

Example 81

(E)-methyl 3-methoxy-2-(2-((2,5-dimethyl-4-(oxazol-5-yl)phenoxy)-methyl)phenyl)acrylate (compound 81)

(E)-methyl 2-(2-((4-formyl-2,5-dimethylphenoxy)methyl)phenyl)-3-methoxyacrylate (0.2 g, 0.56 mmol), which was prepared by repeating the same procedure as in Step 1 of Example 10 with the exception that 4-hydroxy-2,5-dimethylbenzaldehyde was used instead of 3-hydroxybenzaldehyde, was reacted for 2 hours with toluenesulfonylmethyl isocyanide (TOSMIC) (0.13 g, 1.2 eq) in the presence of potassium carbonate (0.12 g, 1.5 eq) in 30 mL of methanol under reflux. The reaction solvent was removed by concentration in a vacuum and the residue was stirred in water (30 mL). The aqueous layer was extracted twice with 30 mL of dichloromethane. Then, the organic layer was dried over anhydrous magnesium sulfate, filtered and concentrated in a vacuum to remove the solvent. Purification by silica gel chromatography afforded (E)-methyl 3-methoxy-2-(2-((2,5-dimethyl-4-(oxazol-5-yl)phenoxy)methyl)phenyl)acrylate as a white solid (0.14 g, yield 66%).

m/s [M+1]=394.40

$^1$H NMR (300 MHz, CDCl$_3$): δ 8.29~8.28 (d, 1H), 7.65~7.64 (d, 1H), 7.59~7.53 (m, 2H), 7.38~7.35 (m, 2H), 7.22~7.20 (m, 1H), 6.67 (s, 1H), 6.31 (s 1H), 5.04 (s, 2H), 3.86 (s, 3H), 3.73 (s, 3H), 2.44 (s, 3H), 2.30 (s, 3H)

Example 82

(E)-methyl 3-methoxy-2-(2-((2,5-dimethyl-4-(1-methyl-1H-pyrazol-3-yl)phenoxy)methyl)phenyl)acrylate (compound 82)

<Step 1>

The compound (0.5 g, 1.36 mmol) synthesized in Step 2 of Example 77 was reacted with N,N-dimethylformamide dimethyl acetal (12 mL) for 10 hours under reflux. After the reaction solvent was removed by concentration in a vacuum, silica gel chromatography afforded (E)-methyl 3-methoxy-2-(2-((4-((E)-3-(dimethylamino)acryloyl)-2,5-dimethylphenoxy)methyl)phenyl)acrylate as a yellowish solid (0.18 g, yield 31.5%).

$^1$H NMR (300 MHz, CDCl$_3$): δ 7.68 (s, 1H), 7.57 (d, 1H), 7.54~7.16 (m, 4H), 6.65 (s, 1H), 5.63 (s, 1H), 5.37 (d, 1H), 5.07 (s, 2H), 3.91 (s, 3H), 3.67 (s, 3H), 2.30 (s, 3H), 2.21 (s, 3H), 2.10 (s, 3H), 2.07 (s, 3H)

<Step 2>

(E)-methyl 3-methoxy-2-(2-((4-((E)-3-(dimethylamino)acryloyl)-2,5-dimethylphenoxy)-methyl)phenyl)acrylate (0.11 g, 0.25 mmol) obtained in Step 1 was reacted with 17 mg (1.5 eq) of methylhydroxyamine in 10 mL of methanol at room temperature for 3 hours with stirring, and then the reaction solvent was removed at a reduced pressure. The residue was stirred in water (20 mL), and the aqueous layer was extracted twice with 30 mL of dichloromethane. The organic layer was dried over anhydrous magnesium sulfate and concentrated in a vacuum. Purification by chromatography afforded (E)-methyl 3-methoxy-2-(2-((2,5-dimethyl-4-(1-methyl-1H-pyrazol-3-yl)phenoxy)methyl)phenyl)acrylate as a white solid (75 mg, yield: 74%).

$^1$H NMR (300 MHz, CDCl$_3$): δ 7.68~7.61 (m, 2H), 7.53~7.52 (m, 1H), 7.42~7.33 (m, 2H), 7.22~7.20 (m, 1H), 6.99 (s, 1H), 6.68 (s, 1H), 6.16 (s, 1H), 5.02 (2, 2H), 3.87 (s, 3H), 3.74 (s, 3H), 3.66 (s, 3H), 2.27 (s, 3H), 2.09 (s, 3H)

The substituents of the compounds in accordance with the present invention are summarized in Table 1.

TABLE 1

| Example | R$_1$ | R$_2$ | R$_3$ |
|---|---|---|---|
| 1 | Me | H | —C(=N-O-CH$_2$CH$_2$-CH$_3$)(CH$_3$) |
| 2 | Me | H | —C(=N-O-CH$_2$-CH$_3$)(CH$_3$) |
| 3 | H | —CH$_2$-O-Ph | H |
| 4 | H | —CH=N-O-CH$_2$-CH$_3$ | H |
| 5 | H | OH | H |
| 6 | OMe | H | H |
| 7 | H | —C(=N-O-CH$_2$CH$_2$-CH$_3$)(CH$_3$) | H |
| 8 | H | H | —C(=N-O-CH$_2$-CH$_3$)(CH$_3$) |
| 9 | H | H | —C(=N-O-CH$_2$CH$_2$-piperidinyl)(CH$_3$) |

TABLE 1-continued
| | | | |
|---|---|---|---|
| 10 | H | 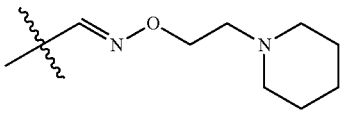 [SMILES: */C=N/OCCN1CCCCC1] | H |
| 11 | H | 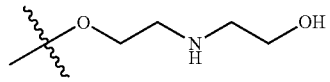 [SMILES: *OCCNCCO] | H |
| 12 | H | 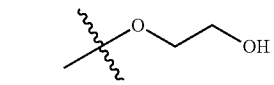 | H |
| 13 | H | 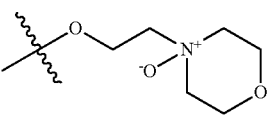 | H |
| 14 | H | 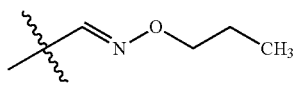 [SMILES: */C=N/OCCC] | H |
| 15 | H | OH | H |
| 16 | H | 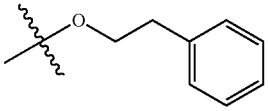 [SMILES: *OCCc1ccccc1] | H |
| 17 | H | H | 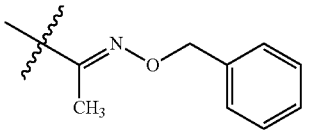 [SMILES: */C(C)=N/OCc1ccccc1] |
| 18 | H | H | 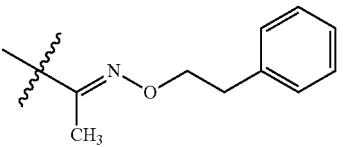 [SMILES: */C(C)=N/OCCc1ccccc1] |
| 19 | H | H | F |
| 20 | H | OH | H |
| 21 | H | 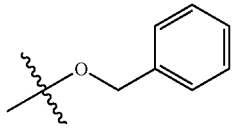 [SMILES: *OCc1ccccc1] | H |
| 22 | H | 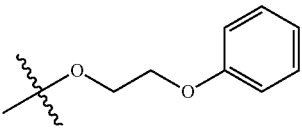 [SMILES: *OCCOc1ccccc1] | H |
| 23 | H | 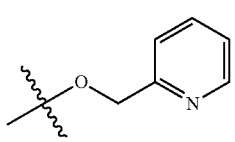 [SMILES: *OCc1ccccn1] | H |

TABLE 1-continued
| | | | |
|---|---|---|---|
| 24 | H | 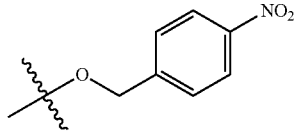 [SMILES: *OCc1ccc([N+](=O)[O-])cc1] | H |
| 25 | H | 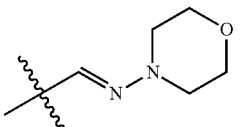 [SMILES: */C=N/N1CCOCC1] | H |
| 26 | H | 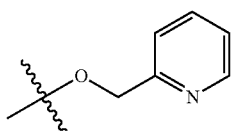 [SMILES: *OCc1ccccn1] | H |
| 27 | H | 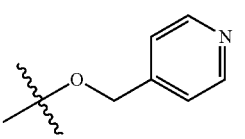 [SMILES: *OCc1ccncc1] | H |
| 28 | H | 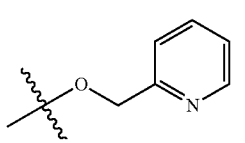 [SMILES: *OCc1ccccn1] | H |
| 29 | H | 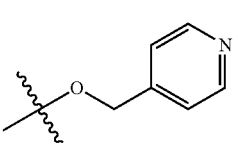 [SMILES: *OCc1ccncc1] | H |
| 30 | Me | H | 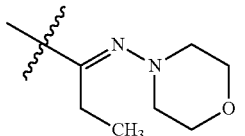 |
| 31 | Me | H | 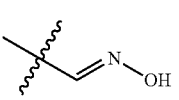 [SMILES: */C=N/O] |
| 32 | Me | H | 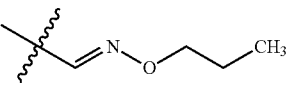 [SMILES: */C=N/OCCC] |
| 33 | Me | H | 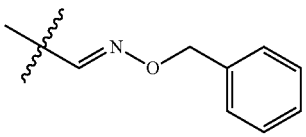 [SMILES: */C=N/OCc1ccccc1] |
| 34 | OMe | H | 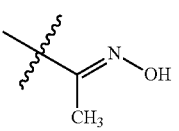 |
| 35 | OMe | H | 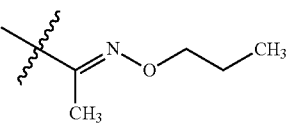 |

TABLE 1-continued

| # | R1 | R2 | R3 |
|---|----|----|----|
| 36 | OMe | H | ![structure: C(CH3)=N-O-CH2-phenyl] |
| 37 | OMe | H | H |
| 38 | OMe | H | H |
| 39 | OMe | H | H |
| 40 | Me | ![structure: -O-CH2CH2CH3] | H |
| 41 | Me | ![structure: -O-CH2-phenyl] | |
| 42 | OMe | H | H |
| 43 | OMe | H | H |
| 44 | OMe | H | H |
| 45 | OMe | H | H |
| 46 | OMe | H | H |
| 47 | H | H | H |
| 48 | OMe | H | H |
| 49 | Me | H | ![structure: CH=N-O-CH2CH2CH3] |
| 50 | Me | H | ![structure: CH=N-O-CH2-phenyl] |
| 51 | Me | H | ![structure: CH=N-O-CH2CH2-O-phenyl] |
| 52 | Me | H | ![structure: CH=N-O-CH2-epoxide] |
| 53 | Me | H | ![structure: CH=N-O-CH2CH2-pyrrolidine] |
| 54 | Me | H | ![structure: CH=N-O-CH2CH2-piperidine] |
| 55 | Me | OH | H |
| 56 | Me | ![structure: -O-CH2CH2-O-phenyl] | H |
| 57 | OMe | H | H |
| 58 | OMe | H | H |

TABLE 1-continued

| | | | |
|---|---|---|---|
| 59 | Me | H | (structure: =N-O-CH2CH2-phenyl) |
| 60 | Me | H | (structure: =N-O-CH2-(4-methylphenyl)) |
| 61 | OMe | H | (structure: =N-O-CH2-phenyl) |
| 62 | F | (structure: -O-CH2-phenyl) | F |
| 63 | Me | H | (structure: =N-O-phenyl) |
| 64 | OMe | H | (structure: =N-O-CH2CH2CH3) |
| 65 | F | (structure: -O-CH2CH2CH3) | F |
| 66 | OMe | H | (structure: =N-O-CH2CH2-phenyl) |
| 67 | Me | H | (structure: =N-O-CH2-cyclopropyl) |
| 68 | Me | H | (structure: =N-O-CH2-cyclopropyl) |
| 69 | Me | H | (structure: =N-O-cyclopentyl) |
| 70 | Me | H | (structure: =N-O-cyclopentyl) |
| 71 | Me | H | (structure: =N-O-CH2CH2CH2-O-phenyl) |

TABLE 1-continued
| | | | |
|---|---|---|---|
| 72 | Me | H | 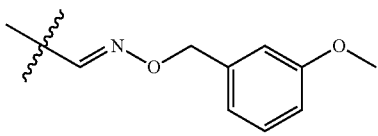 [SMILES: */C=N/OCc1cccc(OC)c1] |
| 73 | Me | H | 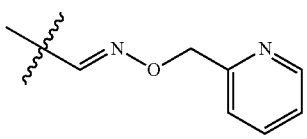 [SMILES: */C=N/OCc1ccccn1] |
| 74 | Me | H | 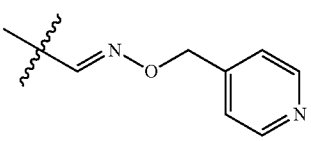 [SMILES: */C=N/OCc1ccncc1] |
| 75 | H | 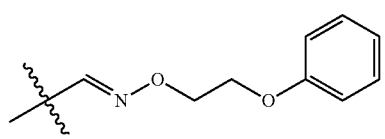 [SMILES: */C=N/OCCOc1ccccc1] | H |
| 76 | H | 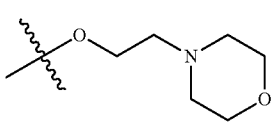 | H |
| 77 | Me | H | 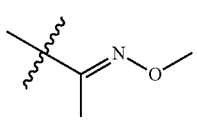 |
| 78 | Me | H | 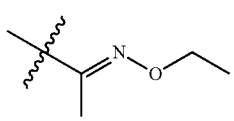 [SMILES: */C(C)=N/OCC] |
| 79 | Me | H | 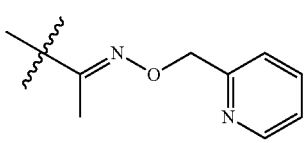 [SMILES: */C(C)=N/OCc1ccccn1] |
| 80 | Me | H | 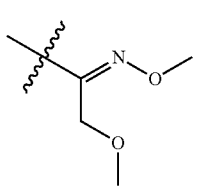 [SMILES: */C(COC)=N/OC] |
| 81 | Me | H | 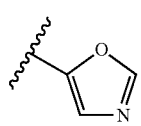 [SMILES: *c1cnco1] |
| 82 | Me | H | 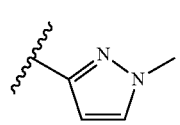 |
| Example | $R_4$ | $R_5$ |
|---|---|---|
| 1 | Me | H |
| 2 | Me | H |

TABLE 1-continued

| # | R | R' |
|---|---|---|
| 3 | H | H |
| 4 | H | H |
| 5 | H | H |
| 6 | -C(CH₃)(H)-CHO group | H |
| 7 | H | H |
| 8 | H | H |
| 9 | H | H |
| 10 | H | H |
| 11 | H | H |
| 12 | H | H |
| 13 | H | H |
| 14 | H | H |
| 15 | F | H |
| 16 | H | H |
| 17 | H | H |
| 18 | H | H |
| 19 | H | H |
| 20 | -C(CH₃)₂-O-CH₂CH₂-O-C₆H₅ group | H |
| 21 | F | H |
| 22 | F | H |
| 23 | F | H |
| 24 | F | H |
| 25 | H | H |
| 26 | H | H |
| 27 | H | H |
| 28 | OH | H |
| 29 | OH | H |
| 30 | Me | H |
| 31 | H | H |
| 32 | H | H |
| 33 | H | H |
| 34 | H | H |
| 35 | H | H |
| 36 | H | H |
| 37 | -C(CH₃)=N-OH group | H |
| 38 | -C(CH₃)=N-O-CH₂-C₆H₅ group | H |
| 39 | -CH=N-O-CH₂-C₆H₅ group | H |
| 40 | Me | H |
| 41 | Me | H |
| 42 | -C(CH₃)=N-O-CH₂CH₂CH₃ group | H |

TABLE 1-continued
| | | |
|---|---|---|
| 43 | 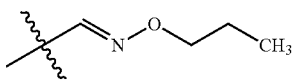 [SMILES: */C=N/OCCC] | H |
| 44 | 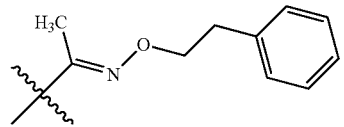 [SMILES: */C(C)=N/OCCc1ccccc1] | H |
| 45 | 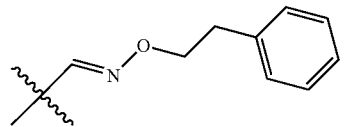 [SMILES: */C=N/OCCc1ccccc1] | H |
| 46 | 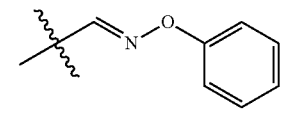 [SMILES: */C=N/Oc1ccccc1] | H |
| 47 | 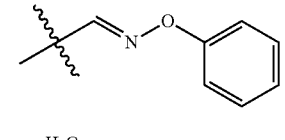 | H |
| 48 | 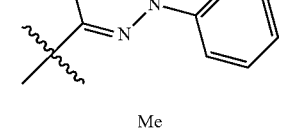 | H |
| 49 | Me | H |
| 50 | Me | H |
| 51 | Me | H |
| 52 | Me | H |
| 53 | Me | H |
| 54 | Me | H |
| 55 | Me | H |
| 56 | Me | H |
| 57 | 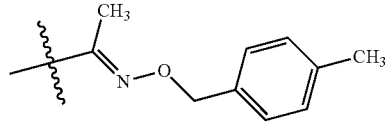 [SMILES: */C(C)=N/OCc1ccc(C)cc1] | H |
| 58 | 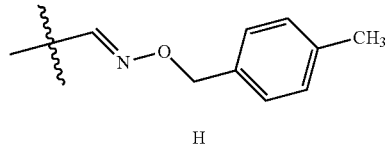 | H |
| 59 | H | H |
| 60 | H | H |
| 61 | H | F |
| 62 | H | H |
| 63 | Me | H |
| 64 | H | F |
| 65 | H | H |
| 66 | H | F |
| 67 | H | H |
| 68 | Me | H |
| 69 | Me | H |
| 70 | H | H |
| 71 | Me | H |
| 72 | Me | H |
| 73 | Me | H |
| 74 | Me | H |
| 75 | H | H |
| 76 | H | H |
| 77 | Me | H |
| 78 | Me | H |

TABLE 1-continued

| | | |
|---|---|---|
| 79 | Me | H |
| 80 | Me | H |
| 81 | Me | H |
| 82 | Me | H |

The compounds obtained in the examples were evaluated as below.

Test 1: Assay for Inhibitory Activity Against HIF Activity

Figure 1B:
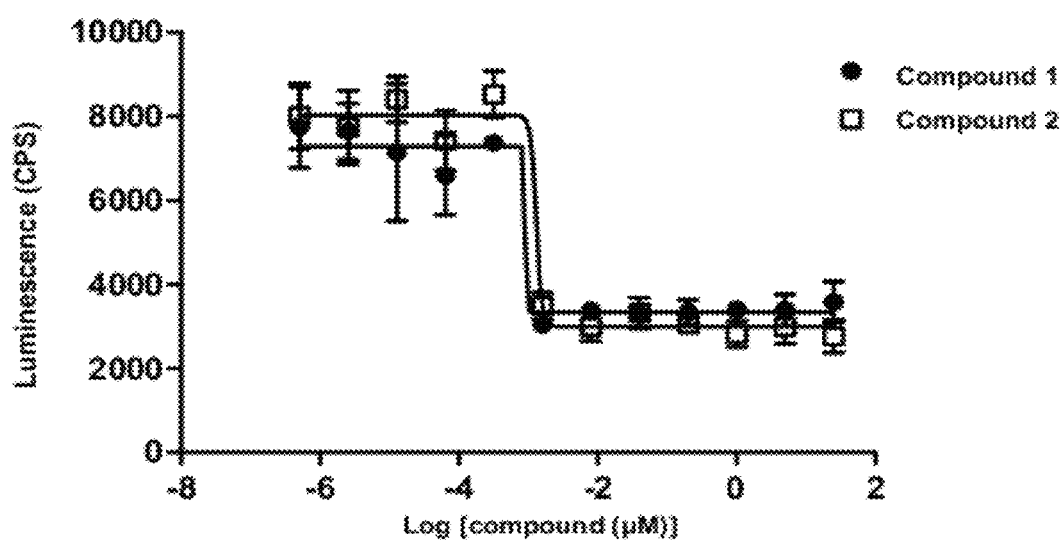
Figure 1C:
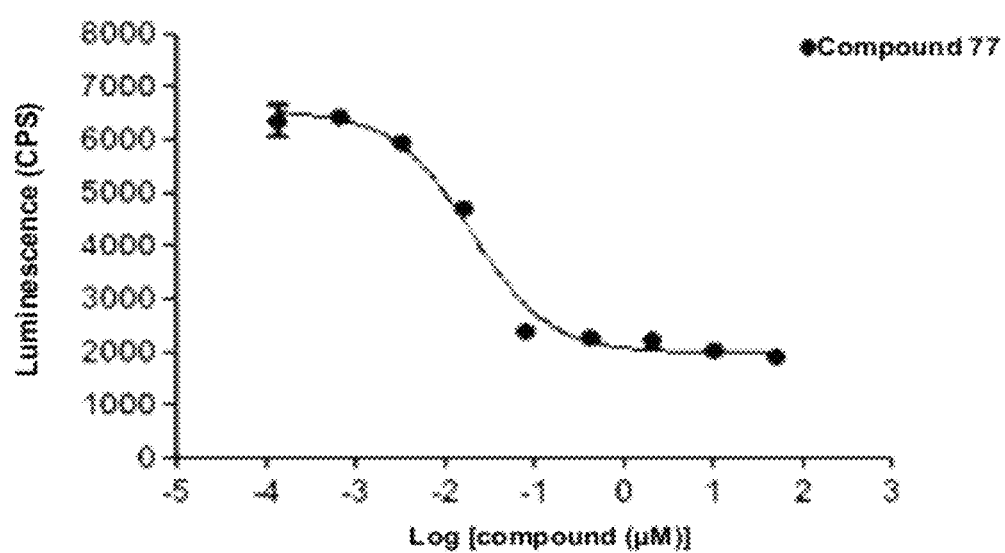

In order to assay the compounds of the present invention for inhibitory activity against HIF activity, the HIF1 reporter plasmid (Panomics) that is designed to control the expression of luciferase by HIF was employed. The HIF1 reporter plasmid and the pTK-Hyg plasmid (Clontech), which carries a hygromycin resistant gene, were co-transfected into the HEK293 cell line (the Korean Cell Line Bank, KCLB No. 21573), derived from the human kidney, with the aid of Effectene transfection reagent (Qiagen). Then, the cells were cultured for 3 weeks on a medium containing 200 μg/mL hygromycin to select transformants resistant to hygromycin. The cell colonies derived from single cells were transferred to 24-well plates to secure a reporter cell line. The cells were seeded at a density of $4 \times 10^4$ cells/well into 96-well plates containing DMEM and incubated for 24 hours before treatment with the compounds of the present invention at a concentration of 25 μM, 5 μM, 1 μM, 200 nM, 40 nM, 8 nM, 1.6 nM, 320 pM, 64 pM, 12.8 pM, 2.56 pM, 512 fM, 102 fM, 20.4 fM, or an amount between any two concentrations above as shown in FIGS. 1A to 1C. Under 1% oxygen condition, the cells were incubated for 6 hours and then, the medium was removed. The cells were lyzed by incubation for 5 min with 100 μL of the mixture of Bright-Glo™ luciferase assay buffer and Bright-Glo™ luciferase assay substrate (Promega). The whole cell lysate was transferred to 96-well, white plates (PerkinElmer) and measured for luminescence using Victor™ 3 (PerkinElmer). From the luminescence measurements, $IC_{50}$ (a concentration of the compound at which luciferase activity was 50% inhibited) was calculated using the GraphPad Prism™ 4 program. The results are summarized in Table 2 and illustrated in FIGS. 1A to 1C.

TABLE 2

| Compound | $IC_{50}$ (μM) |
|---|---|
| 1 | 0.001 |
| 2 | 0.001 |
| 3 | 0.05 |
| 4 | 0.29 |
| 5 | 1.99 |
| 6 | 14.65 |
| 7 | 5.07 |
| 8 | 1.11 |
| 9 | 6.41 |
| 10 | 7.07 |
| 11 | 0.64 |
| 12 | 5.99 |
| 13 | 10.03 |
| 14 | 19.86 |
| 15 | 3.72 |
| 16 | 0.34 |
| 17 | 0.37 |
| 18 | 0.40 |
| 19 | 0.92 |
| 20 | 6.06 |
| 21 | 0.49 |
| 22 | 0.26 |
| 23 | 0.23 |
| 24 | 0.64 |
| 25 | 0.44 |
| 26 | 0.51 |
| 27 | 0.34 |
| 28 | 0.71 |
| 29 | 10.97 |
| 30 | 4.14 |
| 31 | 1.73 |
| 32 | 0.02 |
| 33 | 0.21 |
| 34 | 4.48 |
| 35 | 1.92 |
| 36 | 0.88 |
| 37 | 7.22 |
| 38 | 1.67 |
| 39 | 1.41 |
| 40 | 12.59 |
| 41 | 6.12 |
| 42 | 5.07 |
| 43 | 0.96 |
| 44 | 2.18 |
| 45 | 0.11 |
| 46 | 0.17 |
| 47 | 0.03 |
| 48 | 8.58 |
| 49 | 0.01 |
| 50 | 0.07 |
| 51 | 0.02 |
| 52 | 2.25 |
| 53 | 6.64 |
| 54 | 6.63 |
| 55 | 3.69 |
| 56 | 2.14 |
| 57 | 3.94 |
| 58 | 1.26 |
| 59 | 0.261 |
| 60 | 0.11 |
| 61 | 5.54 |
| 62 | 0.2 |
| 63 | 0.04 |
| 64 | 2.62 |
| 65 | 1 |
| 66 | 0.9 |
| 67 | 0.06 |
| 68 | 0.007 |
| 69 | 0.03 |
| 70 | 0.18 |
| 71 | 0.02 |
| 72 | 0.18 |
| 73 | 0.03 |
| 74 | 0.06 |
| 75 | 0.15 |
| 76 | 1.50 |
| 77 | 0.020 |
| 78 | 0.020 |
| 79 | 0.061 |
| 80 | 0.009 |
| 81 | 0.037 |
| 82 | 0.002 |

As can be seen in FIGS. 1A to 1C, the compounds of the present invention inhibited HIF transcription activity in a dose-dependent manner.

Test 2: Assay for Inhibitory Activity Against HIF at Protein Level

Figure 2A:
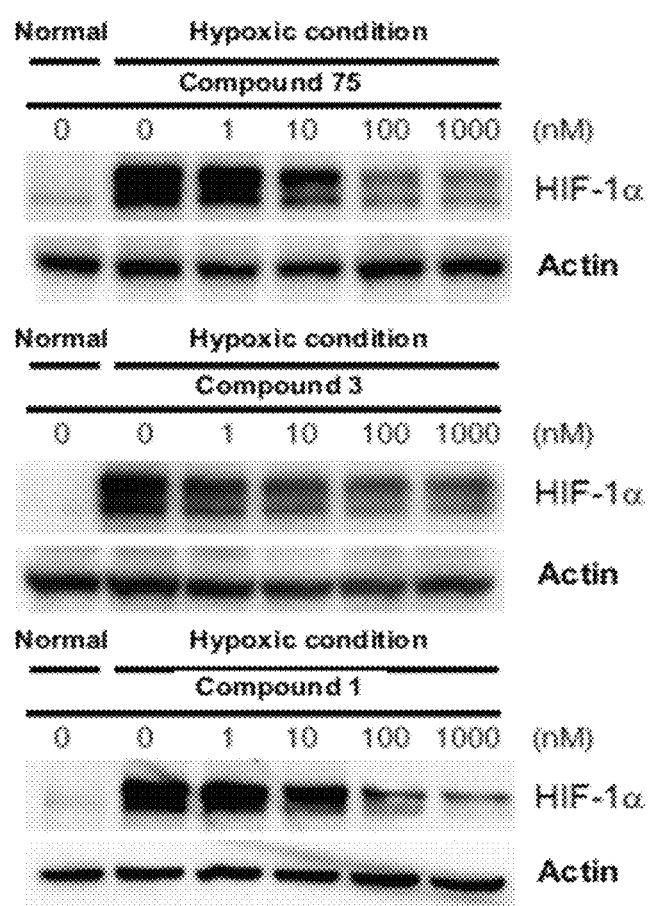
FIGS. 2A to 2C: intracellular HIF-1α and β-actin protein levels in the human cancer cells which have been incubated with the compound of the present invention for 4 hours under a 1% oxygen condition as analyzed by Western blotting.
Figure 2B:
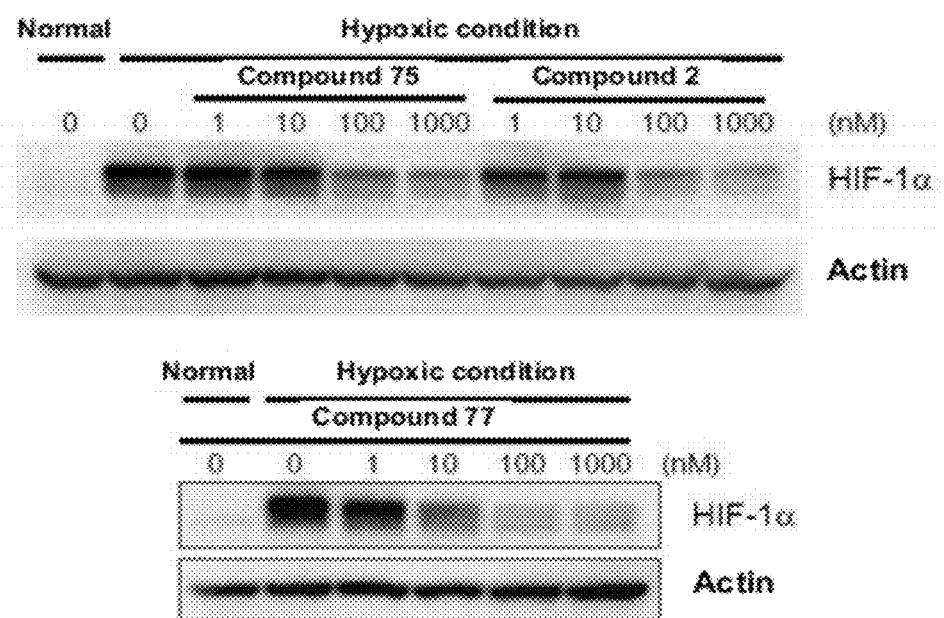
Figure 2C:
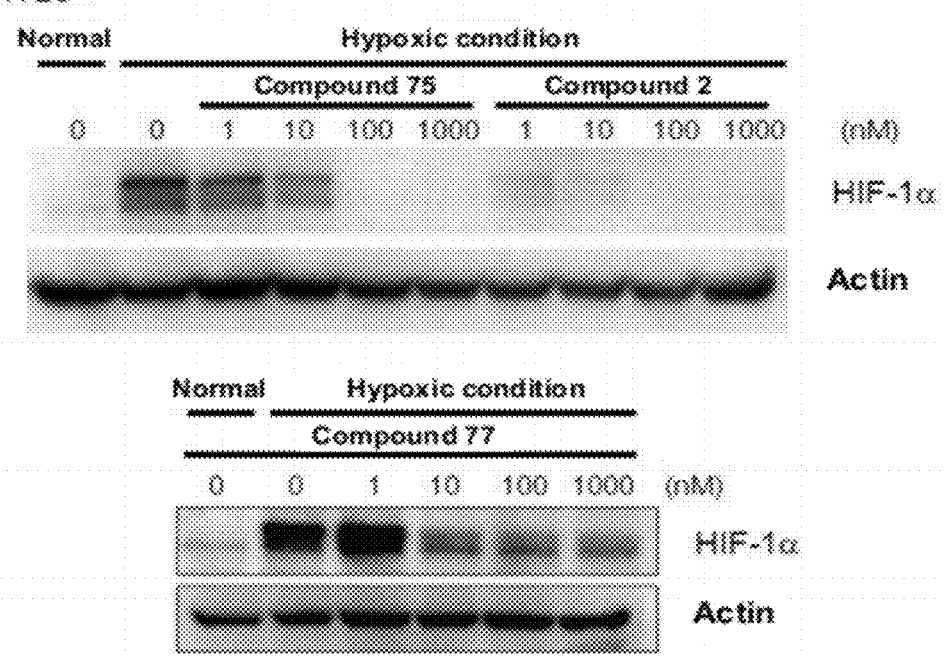

In order to quantitatively analyze the ability of the compounds of the present invention to suppress intracellular HIF- 1α levels, Western blotting was performed. In this regard, H460, a human lung cancer cell line, and HCT116 and HT29, both derived from human colorectal cancer cells (the Korean Cell Line Bank, KCLB Nos. 10247 and 30038) were employed. The cells were inoculated at a population of $3\times10^6$ cells/dish into 60 mm dishes and incubated for 24 hours. After treatment with the compounds of the present invention at a concentration of 1, 10, 100, and 1000 nM, the cells were incubated for 4 hours under a 1% oxygen condition. They were washed with phosphate buffered saline (PBS), lyzed with RIPA buffer (25 mM Tris HCl pH 7.6, 150 mM NaCl, 1% NP-40, 1% sodium deoxycholate, 0.1% SDS), and centrifuged at 4° C. and 10,000 g for 15 min. Protein levels in the supernatants were determined using a Dc protein assay kit (BioRad), and 30 μg of the proteins was run on 8% SDS-PAGE by electrophoresis. The proteins thus separated were transferred onto a PVDF membrane (Millipore, IPVH00010) and reacted with an anti-HIF-1α antibody (BD, 610958) and an HRP (horseradish peroxidase)-conjugated anti-IgG antibody, sequentially. Luminescence was developed using the ECL west pico substrate (Pierce) and analyzed using LAS-100 Plus™ (Fuji). After the removal of the anti-HIF-1α antibody therefrom by strip buffer (Thermo Scientific, part No. 21059), the membrane was reacted with an anti-actin antibody and luminescence images were obtained in the same manner. Western blot results were shown in FIGS. 2A to 2C. As can be seen in FIGS. 2A to 2C, the compounds of the present invention inhibited the intracellular levels of HIF proteins in a dose-dependent manner.

Test 3: Assay for Inhibitory Activity Against HIF-Regulated Genes VEGF and GLUT-1 at mRNA Level To examine the inhibitory activity of the compounds of the present invention against genes the expression of which is induced by HIF, VEGF and GLUT-1 were quantitatively determined at the mRNA level by RT-PCR. The human lung cancer cell line H460 or the human colon cancer cell line HCT116 was inoculated at a density of $3\times10^6$ cells/dish into 60 mm cell culture dishes and incubated for 24 hours. Then, they were treated for 4 hours with 1, 10, 100, and 1000 nM of the compounds of the present invention under a 1% oxygen condition. RNA was isolated from the cells using TRIzol™ (Invitrogen) according to the standard protocol. In the presence of a reverse transcriptase (SuperScript™ III, InVitrogen), 5 μg of the RNA was reverse transcribed, followed by PCR with primers selective for VEGF, GLUT-1 and β-actin.

The primers used in the PCR were 5'-AGACCCTGGTG-GACATCTTC-3' (SEQ ID NO: 1) and 5'-TGCATTCA-CATTTGTTGTGC-3' (SEQ ID NO: 2) for VEGF, 5'-AGAC-CCTGGTGGACATCTTC-3' (SEQ ID NO: 3) and 5'-TGCATTCACATTTGTTGTGC-3' (SEQ ID NO: 4) for GLUT-1, and 5'-AGACCCTGGTGGACATCTTC-3' (SEQ ID NO: 5) and 5'-TGCATTCACATTTGTTGTGC-3' (SEQ ID NO: 6) for β-actin. PCR started denaturation at 95° C. for 5 min, proceeded with 35 cycles of denaturation at 95° C. for 30 sec, annealing at 52° C. for 30 sec and extension at 72° C. for 60 sec, followed by further extension at 72° C. for 5 min.

Figure 3:
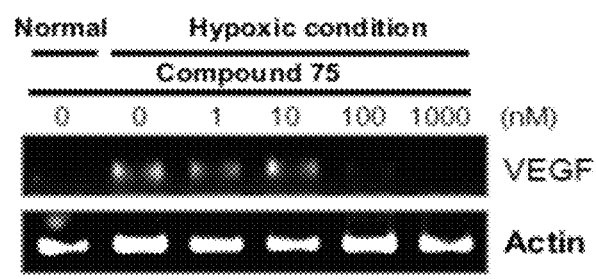
FIG. 3: intracellular VEGF and β-actin mRNA levels in the human lung cancer cell line H460 and the colon cancer cell line HCT-116 which have been incubated with the compound of the present invention for 18 hours under a 1% oxygen condition, as measured by RT-PCR.
Figure 3:
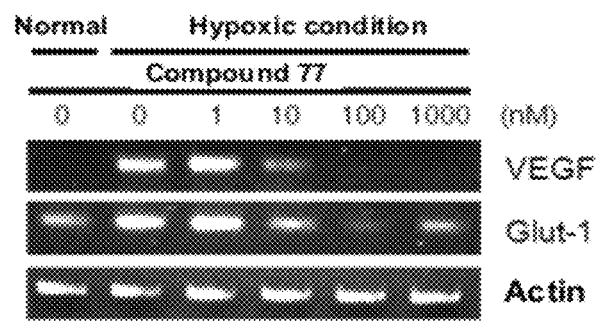
Figure 4A:
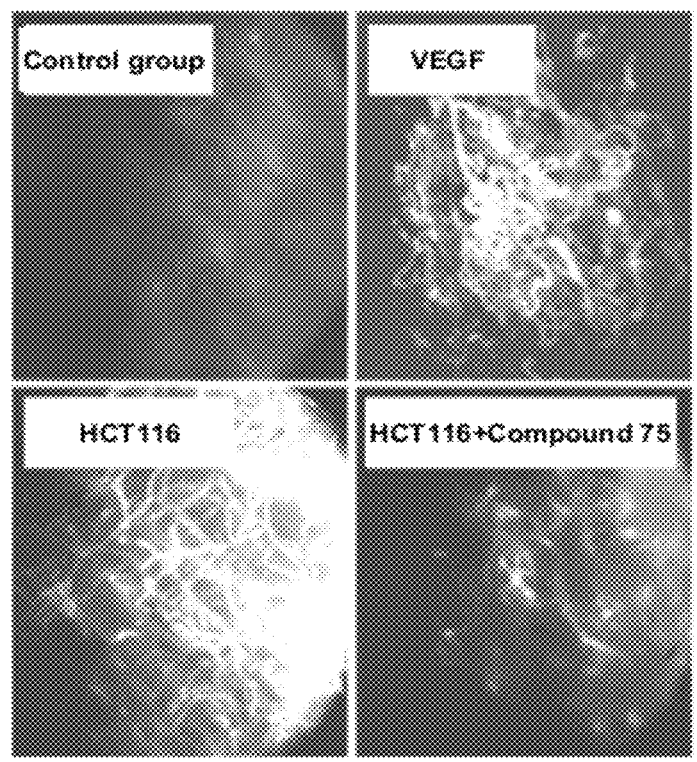
FIG. 4A: a graph showing the suppression of the compound of the present invention against the angiogenesis of tumor in mice
Figure 4B:
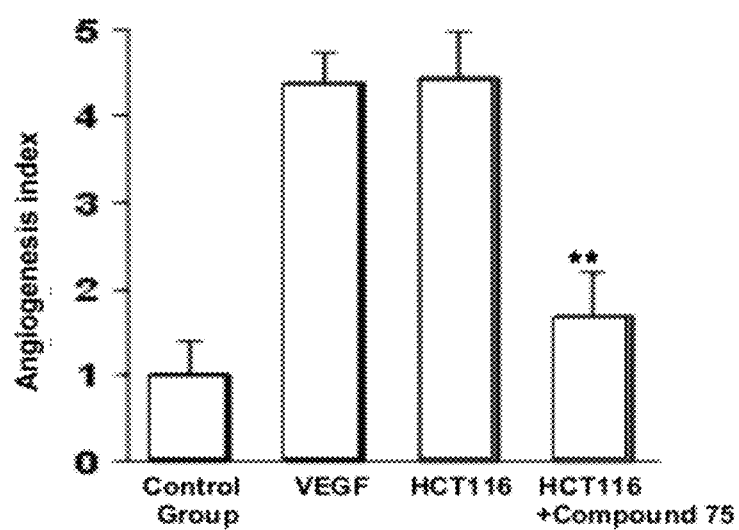
FIG. 4B is a graph quantitatively showing the suppressive activity against angiogenesis (** p<0.01, t-test)

RT-PCR results are shown in FIG. 3. As can be seen in FIG. 3, the compounds of the present invention inhibited the expression of the HIF-upregulated genes in a dose-dependent manner Test 4: Assay for Inhibitory Activity Against In Vivo Tumor-Induced Angiogenesis The inhibitory activity of the compounds of the present invention against angiogenesis was examined in vivo using intravital microscopy. Titanium windows (diameter 19 mm, inner diameter 14 mm, thickness 0.7 mm) were implanted in the abdominal walls male BALB/c mice, 6-8 weeks old, which had been anesthetized. A mixture of 100 μL Matrigel™ 20 ng VEGF, $1\times10^5$ HCT116 or HCT116 cells, and 1 μmol compound 75 was inserted into the tissues inside the window which was then covered with a cover slip and fixed with a snap ring. Four days later, 50 μL of 25 mg/mL fluorescein isothiocyanate-labeled dextran (Mw 250,000 Sigma) was injected via the tail vein to examine angiogenesis. Mice were then placed on a Zeiss Axiovert™ 200M microscope with a filter set (440-475 nm, excitation wavelength; 530-550 nm, emission wavelength). Fluorescence images were recorded in each window by an electron-multiplying CCD camera (Photon Max™ 521, Princeton Instruments) and digitized for subsequent off-line analysis using the MetaMorph™ program (Universal Imaging). The angiogenesis was scored from 0 (least positive) to 5 (most positive). Observations and degree of angiogenesis are shown in FIGS. 4A and 4B, respectively. As shown in these figures, a significant difference was detected between the HCT-116 group and the HCT-116+ compound 75 group as analyzed by t-test (p<0.01). Accordingly, the compound of the present invention was identified to inhibit angiogenesis in vivo.

Test 5: Assay for Suppressive Activity Against Human Pancreatic Cancer Growth in Nude Mice In order to examine the suppressive activity of the compounds of the present invention against tumor growth, male nude mice were implanted with human pancreatic cancer cells and injected with the compounds while the tumor volumes were monitored. The human pancreatic cancer cell line BxPC-3 was implanted on the back of each of 96 male BALB/c nude mice by subcutaneous injection at a density of $5\times10^6$ cells/mouse. When the mean volume of the tumors reached 130 $mm^2$, 72 mice were selected and divided into nine groups of eight in such a manner that volume differences between groups were minimal. A solution of compound 77 in a mixture of Transcutol™ P/Cremophor™ EL/propylene glycol/2.65% trisodium citrate (volume ratio 5:5:40:50) or a solution of erlotinib in a mixture of 0.5% methylcellulose/0.2% Tween™ 80 was injected at a dose of 10 mL/kg into the mice. All test groups were injected twice a day with compound 77 or once a day with erlotinib for 28 days. Compound 77 (3 or 1 mg/kg) and erlotinib (50 mg/kg) were administered alone or in combination.

Long and short axes of the tumors were measured twice a week, and tumor volume was calculated according to the following formula: [Tumor volume (V)=(Length of long axis)×(Length of short axis)$^2$/2].

The tumor volume is expressed as mean±standard error in FIG. 5. The measurements from vehicle groups and test groups were assayed using a t-test (p<0.05 expressed as *, p<0.01 as **). Taken together, the data obtained above demonstrate that the compound of the present invention alone or in combination with another anticancer agent can effectively suppress the growth of tumor in vivo.

While the invention has been described with respect to the above specific embodiments, it should be recognized that various modifications and changes may be made to the invention by those skilled in the art which also fall within the scope of the invention as defined by the appended claims.

What is claimed is:

1. A method for treating pancreatic cancer, psoriasis, diabetic retinopathy, or macular degeneration in a subject in need thereof, comprising administering to the subject an alpha-arylmethoxyacrylate of the following formula 1, or a pharmaceutically acceptable salt, a hydrate, or a solvate thereof:

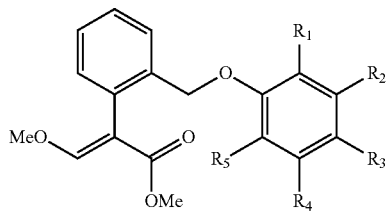

(1)

wherein $R_1$ and $R_5$ are each independently H, hydroxy, halogen, $C_{1-6}$alkyl, or $C_{1-6}$alkoxy;

$R_2$, $R_3$ and $R_4$ are each independently H, hydroxy, halogen, formyl, $C_{1-6}$alkyl, $C_{1-6}$alkoxy, $C_{3-6}$ heteroaryl, or any one of formulae A to C:

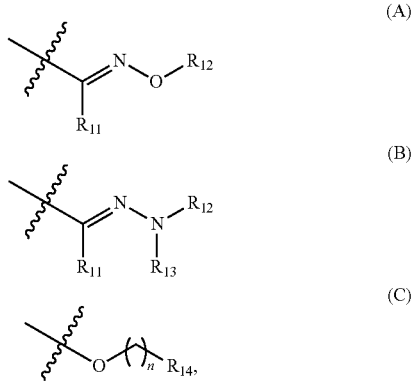

(A)

(B)

(C)

wherein n is an integer of 0 to 4;

$R_{11}$ is H, hydroxy, cyano, $C_{1-4}$alkyl, $C_{2-6}$alkenyl, $C_{1-6}$alkoxy, $C_{1-4}$alkoxy$C_{1-4}$alkyl, $C_{3-8}$cycloalkyl $C_{1-4}$alkyl, or $C_{2-7}$heterocycloalkyl$C_{1-4}$alkyl, $C_{1-4}$alkylamino, or di$C_{1-4}$alkylamino;

$R_{12}$ and $R_{13}$ are each independently H, halogen, $C_{1-6}$alkyl, $C_{2-6}$alkenyl, $C_{2-6}$alkynyl, $C_{3-8}$cycloalkyl, $C_{3-8}$cycloalkyl$C_{1-4}$alkyl, $C_{2-7}$heterocycloalkyl$C_{1-4}$alkyl, $C_{6-12}$aryl, $C_{6-12}$aryl$C_{1-4}$alkyl, $C_{6-12}$aryloxy$C_{1-4}$alkyl, or $C_{3-6}$heteroaryl$C_{1-4}$alkyl, or combine together to form $C_{2-7}$heterocycloalkyl; and $R_{14}$ is H, hydroxy, $C_{3-8}$cycloalkyl, $C_{2-7}$heterocycloalkyl, $C_{6-12}$aryl, $C_{6-12}$ aryl$C_{1-4}$alkyl, $C_{6-12}$aryloxy, $C_{3-6}$heteroaryl, $C_{1-4}$alkylamino, di$C_{1-4}$alkylamino, or

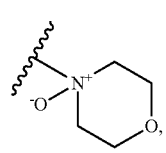

said alkyl, alkenyl and alkoxy each independently being optionally substituted with one or more substituents selected from the group consisting of hydroxy, halogen, nitro and cyano;

said cycloalkyl, heterocycloalkyl, aryl and heteroaryl each independently being optionally substituted with one or more substituents selected from the group consisting of halogen, nitro, cyano, $C_{1-4}$alkyl and $C_{1-4}$alkoxy; and said heterocycloalkyl and heteroaryl each independently comprising at least one atom of N or O.

2. The method of claim 1, wherein at least one of $R_2$, $R_3$ and $R_4$ is selected from formulae A to C.

3. The method of claim 1, wherein $R_{12}$ and $R_{13}$ are each independently H, methyl, ethyl, propyl, cyclopropylmethyl, cyclopentyl, oxirane-2-ylmethyl, pyrrolidinylethyl, piperidinylethyl, phenyl, benzyl, 4-methylbenzyl, 3-methoxybenzyl, phenoxyethyl, phenethyl, pyridin-2-ylmethyl or pyridin-4-ylmethyl, or combine together to form morpholino.

4. The method of claim 1, wherein n is 1 or 2; and $R_{14}$ is hydroxy, morpholino, phenyl, phenoxy, pyridin-2-yl, pyridin-4-yl, 4-nitrophenyl,

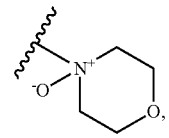

or hydroxyethylamino.

5. The method of claim 1, wherein $R_1$ and $R_5$ are each independently H, methyl, methoxy, or fluoro.

6. The method of claim 1, wherein the alpha-arylmethoxyacrylate of formula 1 is selected from the group consisting of the following compounds 1) to 82):

1) (E)-methyl 2-(2-((2,5-dimethyl-4-((E)-1-(propoxyimino)propyl)phenoxy)methyl)-phenyl)-3-methoxyacrylate;
2) (E)-methyl 2-(2-((2,5-dimethyl-4-((E)-1-(propoxyimino)ethyl)phenoxy)methyl)-phenyl)-3-methoxyacrylate;
3) (E)-methyl 2-(2-((3-(benzyloxy)phenoxy)methyl)phenyl)-3-methoxyacrylate;
4) (E)-methyl 2-(2((3-((E)-(ethoxyimino)methyl)phenoxy)methyl)phenyl)-3-methoxyacrylate;
5) (E)-methyl 2-(2-((5-hydroxyphenoxy)methyl)phenyl)-3-methoxyacrylate;
6) (E)-methyl 2-(2-((5-formyl-2-methoxyphenoxy)methyl)phenyl)-3-methoxyacrylate;
7) (E)-methyl 2-(2-((3-((E)-1-(propoxyimino)propyl)phenoxy)methyl)phenyl)-3-methoxyacrylate;
8) (E)-methyl 2-(2-((4-((E)-1-(propoxyimino)ethyl)phenoxy)methyl)phenyl)-3-methoxyacrylate;
9) (E)-methyl 2-(2-((4-((E)-1-(2-(piperidin-1-yl)ethoxyimino)ethyl)phenoxy)methyl)-phenyl)-3-methoxyacrylate;
10) (E)-methyl 2-(2-((3-((E)-2-(piperidin-1-yl)ethoxyimino)methyl)-phenoxy)methyl)phenyl)-3-methoxyacrylate;
11) (E)-methyl 2-(2-((3-(2-(2-hydroxyethylamino)ethoxy)phenoxy)methyl)phenyl)-3-methoxyacrylate;
12) (E)-methyl 2-(2-((3-(2-hydroxyethoxy)phenoxy)methyl)phenyl)-3-methoxyacrylate;
13) (E)-4-(2-(3-(2-(1,3-dimethoxy-3-oxoprop-1-en-2-yl)benzyloxy)phenoxy)ethyl)-morpholine 4-oxide;

14) (E)-methyl 2-(2-((3-((E)-(propoxyimino)methyl)phenoxy)methyl)phenyl)-3-methoxyacrylate;
15) (E)-methyl 2-(2-((3-fluoro-5-hydroxyphenoxy)methyl)phenyl)-3-methoxyacrylate;
16) (E)-methyl 2-(2-((3-phenethoxyphenoxy)methyl)phenyl)-3-methoxyacrylate;
17) (E)-methyl 2-(2-((4-((E)-1-(benzyloxyimino)ethyl)phenoxy)methyl)phenyl)-3-methoxyacrylate;
18) (E)-methyl 2-(2-((4-((E)-1-(phenethoxyimino)ethyl)phenoxy)methyl)phenyl)-3-methoxyacrylate;
19) (E)-methyl 2-(2-((4-fluorophenoxy)methyl)phenyl)-3-methoxyacrylate;
20) (E)-methyl 2-(2-((3-hydroxy-5-(2-phenoxyethoxy)phenoxy)methyl)phenyl)-3-methoxyacrylate;
21) (E)-methyl 2-(2-((3-(benzyloxy)-5-fluorophenoxy)methyl)phenyl)-3-methoxyacrylate;
22) (E)-methyl 2-(2-((3-fluoro-5-(2-phenoxyethoxy)phenoxy)methyl)phenyl)-3-methoxyacrylate;
23) (E)-methyl 2-(2-((3-fluoro-5-(pyridin-2-ylmethoxy)phenoxy)methyl)phenyl)-3-methoxyacrylate;
24) (E)-methyl 2-(2-((3-fluoro-5-(4-nitrobenzyloxy)phenoxy)methyl)phenyl)-3-methoxyacrylate;
25) (E)-methyl 2-(2-((3-((E)-(morpholinoimino)methyl)phenoxy)methyl)phenyl)-3-methoxyacrylate;
26) (E)-methyl 2-(2-((3-(pyridin-2-ylmethoxy)phenoxy)methyl)phenyl)-3-methoxyacrylate;
27) (E)-methyl 2-(2-((3-(pyridin-4-ylmethoxy)phenoxy)methyl)phenyl)-3-methoxyacrylate;
28) (E)-methyl 2-(2-((3-hydroxy-5-(pyridin-2-ylmethoxy)phenoxy)methyl)phenyl)-3-methoxyacrylate;
29) (E)-methyl 2-(2-((3-hydroxy-5-(pyridin-4-ylmethoxy)phenoxy)methyl)phenyl)-3-methoxyacrylate;
30) (E)-methyl 2-(2-((2,5-dimethyl-4-((E)-1-(morpholinoimino)propyl)phenoxy)-methyl)phenyl)-3-methoxyacrylate;
31) (E)-methyl 2-(2-((4-((E)-(hydroxyimino)methyl)-2-methylphenoxy)methyl)phenyl)-3-methoxyacrylate;
32) (E)-methyl 2-(2-((2-methyl-4-((E)-(propoxyimino)methyl)phenoxy)methyl)phenyl)-3-methoxyacrylate;
33) (E)-methyl 2-(2-((4-((E)-(benzyloxyimino)methyl)-2-methylphenoxy)methyl)-phenyl)-3-methoxyacrylate;
34) (E)-methyl 2-(2-((4-((E)-1-(hydroxyimino)ethyl)-2-methoxyphenoxy)methyl)-phenyl)-3-methoxyacrylate;
35) (E)-methyl 2-(2-((4-((E)-1-(propoxyimino)ethyl)-2-methoxyphenoxy)methyl)-phenyl)-3-methoxyacrylate;
36) (E)-methyl 2-(2-((4-((E)-1-benzyloxyimino)ethyl)-2-methoxyphenoxy)methyl)-phenyl)-3-methoxyacrylate;
37) (E)-methyl 2-(2-((5-((E)-1-(hydroxyimino)ethyl)-2-methoxyphenoxy)methyl)-phenyl)-3-methoxyacrylate;
38) (E)-methyl 2-(2-((5-((E)-1-(benzyloxyimino)ethyl)-2-methoxyphenoxy)methyl)-phenyl)-3-methoxyacrylate;
39) (E)-methyl 2-(2-((5-((E)-(benzyloxyimino)methyl)-2-methoxyphenoxy)methyl)-phenyl)-3-methoxyacrylate;
40) (E)-methyl 2-(2-((2,5-dimethyl-3-propoxyphenoxy)methyl)phenyl)-3-methoxyacrylate;
41) (E)-methyl 2-(2-((3-(benzyloxy)-2,5-dimethylphenoxy)methyl)phenyl)-3-methoxyacrylate;
42) (E)-methyl 2-(2-((2-methoxy-5-((E)-1-(propoxyimino)ethyl)phenoxy)methyl)-phenyl)-3-methoxyacrylate;
43) (E)-methyl 2-(2-((2-methoxy-5-((E)-(propoxyimino)methyl)phenoxy)methyl)-phenyl)-3-methoxyacrylate;
44) (E)-methyl 2-(2-((2-methoxy-5-((E)-1-(phenylethoxyimino)ethyl)phenoxy)methyl)-phenyl)-3-methoxyacrylate;
45) (E)-methyl 2-(2-((2-methoxy-5-((E)-1-(phenylethoxyimino)methyl)phenoxy)-methyl)phenyl)-3-methoxyacrylate;
46) (E)-methyl 2-(2-((2-methoxy-5-((E)-1-(phenoxyimino)methyl)phenoxy)methyl)-phenyl)-3-methoxyacrylate;
47) (E)-methyl 2-(2-((3-((E)-1-(phenoxyimino)methyl)phenoxy)methyl)phenyl)-3-methoxyacrylate;
48) (E)-methyl 2-(2-((2-methoxy-5-((E)-1-(phenylhydrazono)ethyl)phenoxy)methyl)-phenyl)-3-methoxyacrylate;
49) (E)-methyl 2-(2-((2,5-dimethyl-4-((E)-(propoxyimino)methyl)phenoxy)methyl)-phenyl)-3-methoxyacrylate;
50) (E)-methyl 2-(2-((4-((E)-(benzyloxyimino)methyl)-2,5-dimethylphenoxy)methyl)-phenyl)-3-methoxyacrylate;
51) (E)-methyl 2-(2-((2,5-dimethyl-4-((E)-(2-phenoxyethoxyimino)methyl)phenoxy)-methyl)phenyl)-3-methoxyacrylate;
52) (E)-methyl 2-(2-((2,5-dimethyl-4-((E)-(oxirane-2-yl-methoxyimino)methyl)-phenoxy)methyl)phenyl)-3-methoxyacrylate;
53) (E)-methyl 2-(2-((2,5-dimethyl-4-((E)-(2-(pyrrolidin-1-yl)ethoxyimino)methyl)-phenoxy)methyl)phenyl)-3-methoxyacrylate;
54) (E)-methyl 2-(2-((2,5-dimethyl-4-((E)-(2-(piperidin-1-yl)ethoxyimino)methyl)-phenoxy)methyl)phenyl)-3-methoxyacrylate;
55) (E)-methyl 2-(2-((3-hydroxy-2,5-dimethylphenoxy)methyl)phenyl)-3-methoxyacrylate;
56) (E)-methyl 2-(2-((2,5-dimethyl-3-(2-phenoxyethoxy)phenoxy)methyl)phenyl)-3-methoxyacrylate;
57) (E)-methyl 2-(2-((2-methoxy-5-((E)-1-(4-methylbenzyloxyimino)ethyl)phenoxy)-methyl)phenyl)-3-methoxyacrylate;
58) (E)-methyl 2-(2-((2-methoxy-5-((E)-1-(4-methylbenzyloxyimino)methyl)phenoxy)-methyl)phenyl)-3-methoxyacrylate;
59) (E)-methyl 2-(2-((2-methyl-4-((E)-(phenylethoxyimino)methyl)phenoxy)methyl)-phenyl)-3-methoxyacrylate;
60) (E)-methyl 2-(2-((2-methyl-4-((E)-(4-methylbenzyloxyimino)methyl)phenoxy)-methyl)phenyl)-3-methoxyacrylate;
61) (E)-methyl 2-(2-((4-((E)-(benzyloxyimino)methyl)-2-fluoro-6-methoxyphenoxy)-methyl)phenyl)-3-methoxyacrylate;
62) (E)-methyl 2-(2-((3-(benzyloxy)-2,4-difluorophenoxy)methyl)phenyl)-3-methoxyacrylate;
63) (E)-methyl 2-(2-((2,5-dimethyl-4-((E)-(phenoxyimino)methyl)phenoxy)methyl)-phenyl)-3-methoxyacrylate;
64) (E)-methyl 2-(2-((2-fluoro-6-methoxy-4-((E)-(propoxyimino)methyl)phenoxy)-methyl)phenyl)-3-methoxyacrylate;
65) (E)-methyl 2-(2-((2,4-difluoro-3-propoxyphenoxy)methyl)phenyl)-3-methoxyacrylate;
66) (E)-methyl 2-(2-((2-fluoro-6-methoxy-4-((E)-(phenethoxyimino)methyl)phenoxy)methyl)phenyl)-3-methoxyacrylate;
67) (E)-methyl 2-(2-((4-((E)-(cyclopropylmethoxyimino)methyl)-2-methylphenoxy)-methyl)phenyl)-3-methoxyacrylate;
68) (E)-methyl 2-(2-((4-((E)-(cyclopropylmethoxyimino)methyl)-2,5-dimethylphenoxy)-methyl)phenyl)-3-methoxyacrylate;

69) (E)-methyl 2-(2-((4-((E)-(cyclopentyloxyimino)methyl)-2,5-dimethylphenoxy)-methyl)phenyl)-3-methoxyacrylate;

70) (E)-methyl 2-(2-((4-((E)-(cyclopentyloxyimino)methyl)-2-methylphenoxy)methyl)-phenyl)-3-methoxyacrylate;

71) (E)-methyl 2-(2-((2,5-dimethyl-4-((E)-(3-phenoxypropyloxyimino)methyl)phenoxy)-methyl)phenyl)-3-methoxyacrylate;

72) (E)-methyl 2-(2-((4-((E)-(3-methoxybenzyloxyimino)methyl)-2,5-dimethylphenoxy)methyl)phenyl)-3-methoxyacrylate;

73) (E)-methyl 2-(2-((4-((E)-(pyridin-2-ylmethoxyimino)methyl)-2,5-dimethylphenoxy)-methyl)phenyl)-3-methoxyacrylate;

74) (E)-methyl 2-(2-((4-((E)-(pyridin-4-ylmethoxyimino)methyl)-2,5-dimethylphenoxy)-methyl)phenyl)-3-methoxyacrylate;

75) (E)-methyl 2-(2-((3-((E)-(2-phenoxyethoxyimino)methyl)phenoxy)methyl)phenyl)-3-methoxyacrylate;

76) (E)-methyl 2-(2-((3-(2-morpholinoethoxy)phenoxy)methyl)phenyl)-3-methoxyacrylate;

77) (E)-methyl 2-(2-((2,5-dimethyl-4-((E)-1-(methoxyimino)ethyl)phenoxy)methyl)-phenyl)-3-methoxyacrylate;

78) (E)-methyl 2-(2-((2,5-dimethyl-4-((E)-1-(ethoxyimino)ethyl)phenoxy)methyl)-phenyl)-3-methoxyacrylate;

79) (E)-methyl 2-(2-((2,5-dimethyl-4-((E)-1-(pyridin-2-ylmethoxyimino)ethyl)phenoxy)-methyl)phenyl)-3-methoxyacrylate;

80) (E)-methyl 2-(2-((4-((Z)-2-methoxy-1-(methoxyimino)ethyl)2,5-dimethylphenoxy)methyl)phenyl)-3-methoxyacrylate;

81) (E)-methyl 2-(2-((2,5-dimethyl-4-(oxazol-5-yl)phenoxy)methyl)phenyl)-3-methoxyacrylate; and 82) (E)-methyl 2-(2-((2,5-dimethyl-4-(1-methyl-1H-pyrazol-3-yl)phenoxy)-methyl)phenyl)-3-methoxyacrylate.

7. The method of claim 1, wherein the alpha-arylmethoxyacrylate of formula 1 is selected from the following 1) to 14):

1) (E)-methyl 2-(2-((2,5-dimethyl-4-((E)-1-(propoxyimino)propyl)phenoxy)methyl)-phenyl)-3-methoxyacrylate;

2) (E)-methyl 2-(2-((2,5-dimethyl-4-((E)-1-(propoxyimino)ethyl)phenoxy)methyl)-phenyl)-3-methoxyacrylate;

3) (E)-methyl 2-(2-((3-(benzyloxy)phenoxy)methyl)phenyl)-3-methoxyacrylate (compound 3);

4) (E)-methyl 2-(2-((4-((E)-(cyclopropylmethoxyimino)methyl)-2,5-dimethylphenoxy)-methyl)phenyl)-3-methoxyacrylate;

5) (E)-methyl 2-(2-((4-((E)-(cyclopentyloxyimino)methyl)-2,5-dimethylphenoxy)-methyl)phenyl)-3-methoxyacrylate;

6) (E)-methyl 2-(2-((4-((E)-(pyridin-2-ylmethoxyimino)methyl)-2,5-dimethylphenoxy)-methyl)phenyl)-3-methoxyacrylate;

7) (E)-methyl 2-(2-((3-((E)-(2-phenoxyethoxyimino)methyl)phenoxy)methyl)phenyl)-3-methoxyacrylate;

8) (E)-methyl 2-(2-((3-(2-morpholinoethoxy)phenoxy)methyl)phenyl)-3-methoxyacrylate;

9) (E)-methyl 2-(2-((2,5-dimethyl-4-((E)-1-(methoxyimino)ethyl)phenoxy)methyl)-phenyl)-3-methoxyacrylate;

10) (E)-methyl 2-(2-((2,5-dimethyl-4-((E)-1-(ethoxyimino)ethyl)phenoxy)methyl)-phenyl)-3-methoxyacrylate;

11) (E)-methyl 2-(2-((2,5-dimethyl-4-((E)-1-(pyridin-2-ylmethoxyimino)ethyl)phenoxy)-methyl)phenyl)-3-methoxyacrylate;

12) (E)-methyl 2-(2-((4-((Z)-2-methoxy-1-(methoxyimino)ethyl)2,5-dimethylphenoxy)methyl)phenyl)-3-methoxyacrylate;

13) (E)-methyl 2-(2-((2,5-dimethyl-4-(oxazol-5-yl)phenoxy)methyl)phenyl)-3-methoxyacrylate; and 14) (E)-methyl 2-(2-((2,5-dimethyl-4-(1-methyl-1H-pyrazol-3-yl)phenoxy)-methyl)phenyl)-3-methoxyacrylate.

8. The method of claim 1, wherein the alpha-arylmethoxyacrylate derivative of formula 1, or a pharmaceutically acceptable salt, a hydrate, or a solvate thereof is administered in a pharmaceutical composition formulation, said pharmaceutical composition formulation comprising the alpha-arylmethoxyacrylate derivative of formula 1, or a pharmaceutically acceptable salt, a hydrate, or a solvate thereof and a pharmaceutically acceptable carrier.

\* \* \* \* \*

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: PCR primer for VEGF

<400> SEQUENCE: 1
agaccctggt ggacatcttc                                              20

<210> SEQ ID NO 2
<211> LENGTH: 20
<212> TYPE: DNA
<213> ORGANISM: Artificial Sequence
<220> FEATURE:
<223> OTHER INFORMATION: PCR primer for VEGF

<400> SEQUENCE: 2
tgcattcaca tttgttgtgc                                              20

<210> SEQ ID NO 3
<211> LENGTH: 20
<212> TYPE: DNA
<213> ORGANISM: Artificial Sequence
<220> FEATURE:
<223> OTHER INFORMATION: PCR primer for GLUT-1

<400> SEQUENCE: 3
agaccctggt ggacatcttc                                              20

<210> SEQ ID NO 4
<211> LENGTH: 20
<212> TYPE: DNA
<213> ORGANISM: Artificial Sequence
<220> FEATURE:
<223> OTHER INFORMATION: PCR primer for GLUT-1

<400> SEQUENCE: 4
tgcattcaca tttgttgtgc                                              20

<210> SEQ ID NO 5
<211> LENGTH: 20
<212> TYPE: DNA
<213> ORGANISM: Artificial Sequence
<220> FEATURE:
<223> OTHER INFORMATION: PCR primer for beta-actin

<400> SEQUENCE: 5
agaccctggt ggacatcttc                                              20

<210> SEQ ID NO 6
<211> LENGTH: 20
<212> TYPE: DNA
<213> ORGANISM: Artificial Sequence
<220> FEATURE:
<223> OTHER INFORMATION: PCR primer for beta-actin

<400> SEQUENCE: 6
tgcattcaca tttgttgtgc                                              20